United States Patent
Feng et al.

(10) Patent No.: US 8,222,411 B2
(45) Date of Patent: Jul. 17, 2012

(54) DIPEPTIDYL PEPTIDASE INHIBITORS

(75) Inventors: Jun Feng, San Diego, CA (US); Stephen L. Gwaltney, Escondido, CA (US); Jeffrey A. Stafford, San Diego, CA (US); Zhiyuan Zhang, San Diego, CA (US); Paul R. Brodfuahrer, Albany, NY (US); Bruce Elder, Wynantskill, NY (US); Paul Isbester, Castleton-on-Hudson, NY (US); Richard S. Fornicola, Liverpool, NY (US); Philip B. Kisanga, Cicero, NY (US); Bingidimi I. Mobele, Altamont, NY (US); Grant J. Palmer, Clifton Park, NY (US); Maxwell M. Reeve, Guilford, CT (US); Jonathon S. Salsbury, Middleton, WI (US); Luckner Ulysse, Albany, NY (US); Sripathy Venkatraman, Guilderland, NY (US)

(73) Assignee: Takeda Pharmaceutical Company Limited, Osaka (JP)

( * ) Notice: Subject to any disclaimer, the term of this patent is extended or adjusted under 35 U.S.C. 154(b) by 616 days.

(21) Appl. No.: 12/066,769

(22) PCT Filed: Sep. 15, 2006

(86) PCT No.: PCT/US2006/036276
§ 371 (c)(1),
(2), (4) Date: Mar. 4, 2009

(87) PCT Pub. No.: WO2007/035629
PCT Pub. Date: Mar. 29, 2007

(65) Prior Publication Data
US 2009/0275750 A1    Nov. 5, 2009

(51) Int. Cl.
C07D 239/02    (2006.01)
(52) U.S. Cl. .................................................. 544/314
(58) Field of Classification Search .................. 544/314
See application file for complete search history.

(56) References Cited

U.S. PATENT DOCUMENTS

| | | | |
|---|---|---|---|
| 3,322,756 A | 5/1967 | Hilmer et al. |
| 3,544,570 A | 12/1970 | Timmler et al. |
| 3,823,135 A | 7/1974 | Pilgram et al. |
| 3,960,949 A | 6/1976 | Ahrens et al. |
| 4,494,978 A | 1/1985 | Chan |
| 4,687,777 A | 8/1987 | Meguro et al. |
| 4,935,493 A | 6/1990 | Bachovchin et al. |
| 5,002,953 A | 3/1991 | Hindley |
| 5,366,862 A | 11/1994 | Venton et al. |
| 5,387,512 A | 2/1995 | Balani et al. |
| 5,433,955 A | 7/1995 | Bredehorst et al. |
| 5,462,928 A | 10/1995 | Bachovchin et al. |
| 5,512,549 A | 4/1996 | Chen et al. |
| 5,543,396 A | 8/1996 | Powers et al. |
| 5,580,979 A | 12/1996 | Bachovchin |
| 5,601,986 A | 2/1997 | Takacs |
| 5,614,379 A | 3/1997 | MacKellar |
| 5,614,492 A | 3/1997 | Habener |
| 5,624,894 A | 4/1997 | Bodor |
| 5,798,344 A | 8/1998 | Kuroki et al. |
| 5,811,278 A | 9/1998 | Okamura et al. |
| 5,811,281 A | 9/1998 | Quaroni et al. |
| 5,814,460 A | 9/1998 | Venton et al. |
| 5,885,997 A | 3/1999 | Lohray et al. |
| 5,939,560 A | 8/1999 | Jenkins et al. |
| 5,965,532 A | 10/1999 | Bachovchin |
| 5,985,884 A | 11/1999 | Lohray et al. |
| 6,006,753 A | 12/1999 | Efendic |
| 6,011,155 A | 1/2000 | Villhauer |
| 6,090,786 A | 7/2000 | Augustyns et al. |
| 6,107,317 A | 8/2000 | Villhauer |
| 6,110,949 A | 8/2000 | Villhauer |
| 6,124,305 A | 9/2000 | Villhauer |
| 6,129,911 A | 10/2000 | Faris |
| 6,156,739 A | 12/2000 | Griffin et al. |
| 6,166,063 A | 12/2000 | Villhauer |
| 6,172,081 B1 | 1/2001 | Damon |
| 6,184,020 B1 | 2/2001 | Blinkovsky et al. |
| 6,201,132 B1 | 3/2001 | Jenkins et al. |
| 6,214,340 B1 | 4/2001 | Takeuchi et al. |
| 6,235,493 B1 | 5/2001 | Bissell et al. |
| 6,251,391 B1 | 6/2001 | Wilkinson et al. |

(Continued)

FOREIGN PATENT DOCUMENTS

DE    2150686 A1    4/1973

(Continued)

OTHER PUBLICATIONS

Kotani et al, J'nal Med. Chem. vol. 40., No. 5, 1997, pp. 684-694.*
Mukkerjee, Sucharita "[2+2] versus [4+2] cycloaddition reactions of 1,3-diaza-1,3-butadienes with various mono and disubtituted ketenes and supporting mechanistic considerations" Heter0cycles, vol. 47, No. 2, 1998 XP001539476.
Noguchi, Michihiko "Generation of NH-azomethine imine intermediates through the 1,2-hydrogen shift of hydrazones and their intermolecular cycloaddition reaction with olefinic dipolarophiles" Tetrahedron vol. 59 (2003), p. 4123-3.
U.S. Appl. No. 12/046,997, filed Dec. 10, 2010, Christopher, Ronald J.

(Continued)

*Primary Examiner* — Paul V. Ward
(74) *Attorney, Agent, or Firm* — Mitchell R. Brustein; David M. Stemerick

(57) ABSTRACT

Methods of making compounds of the formula (I) wherein the variables are as defined herein. Also, methods of making compounds that may be used to inhibit dipeptidyl peptidase.

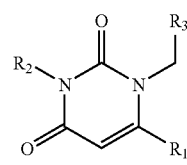

5 Claims, No Drawings

U.S. PATENT DOCUMENTS

| | | |
|---|---|---|
| 6,258,597 B1 | 7/2001 | Bachovchin et al. |
| 6,261,794 B1 | 7/2001 | Chang |
| 6,265,551 B1 | 7/2001 | Duke-Cohan et al. |
| 6,303,661 B1 | 10/2001 | Demuth et al. |
| 6,309,868 B1 | 10/2001 | Monod |
| 6,310,069 B1 | 10/2001 | Lohray et al. |
| 6,319,893 B1 | 11/2001 | Demuth et al. |
| 6,325,989 B1 | 12/2001 | Duke-Cohan et al. |
| 6,335,429 B1 | 1/2002 | Cai et al. |
| 6,337,069 B1 | 1/2002 | Grouzmann et al. |
| 6,342,611 B1 | 1/2002 | Weber et al. |
| 6,355,614 B1 | 3/2002 | Wallner |
| 6,380,398 B2 | 4/2002 | Kanstrup et al. |
| 6,395,767 B2 | 5/2002 | Robl et al. |
| 6,432,969 B1 | 8/2002 | Villhauer |
| 6,447,772 B1 | 9/2002 | Houston |
| 6,448,045 B1 | 9/2002 | Levine et al. |
| 6,458,924 B2 | 10/2002 | Knudsen et al. |
| 6,485,955 B1 | 11/2002 | Huber et al. |
| 6,495,544 B2 | 12/2002 | Hansen, Jr. et al. |
| 6,500,804 B2 | 12/2002 | Demuth et al. |
| 6,518,277 B1 | 2/2003 | Sadhu et al. |
| 6,521,644 B1 | 2/2003 | Broqua |
| 6,528,486 B1 | 3/2003 | Larsen et al. |
| 6,545,170 B2 | 4/2003 | Pitzele et al. |
| 6,548,481 B1 | 4/2003 | Demuth et al. |
| 6,548,529 B1 | 4/2003 | Robl et al. |
| 6,555,519 B2 | 4/2003 | Washburn |
| 6,555,521 B2 | 4/2003 | Hermeling et al. |
| 6,559,188 B1 | 5/2003 | Gatlin et al. |
| 6,573,096 B1 | 6/2003 | Chen |
| 6,573,287 B2 | 6/2003 | Sulsky et al. |
| 6,586,198 B2 | 7/2003 | Brown |
| 6,608,038 B2 | 8/2003 | Caplan et al. |
| 6,617,340 B1 | 9/2003 | Villhauer |
| 6,620,821 B2 | 9/2003 | Robl |
| 6,620,910 B1 | 9/2003 | Calas et al. |
| 6,627,636 B2 | 9/2003 | Robl |
| 6,645,995 B2 | 11/2003 | Kanstrup et al. |
| 6,664,273 B2 | 12/2003 | Burnett et al. |
| 6,673,815 B2 | 1/2004 | Devasthale et al. |
| 6,673,829 B2 | 1/2004 | Dorwald et al. |
| 6,686,337 B2 | 2/2004 | Connor |
| 6,699,871 B2 | 3/2004 | Edmondson et al. |
| 6,703,238 B2 | 3/2004 | Bachovchin et al. |
| 6,706,742 B2 | 3/2004 | De Nanteuil et al. |
| 6,710,040 B1 | 3/2004 | Hulin et al. |
| 6,716,843 B2 | 4/2004 | De Nanteuil et al. |
| 6,727,261 B2 | 4/2004 | Gobbi et al. |
| 6,727,271 B2 | 4/2004 | Cheng et al. |
| 6,747,035 B2 | 6/2004 | Guadilliere et al. |
| 6,800,650 B2 | 10/2004 | Boehringer et al. |
| 6,803,357 B1 | 10/2004 | Bachovchin et al. |
| 6,825,169 B1 | 11/2004 | Bachovchin et al. |
| 6,861,440 B2 | 3/2005 | Boehringer et al. |
| 6,867,205 B2 | 3/2005 | Boehringer et al. |
| 6,998,502 B1 | 2/2006 | Majeed et al. |
| 7,125,881 B2 | 10/2006 | Bailey et al. |
| 7,230,000 B1 | 6/2007 | Finer et al. |
| 7,304,086 B2 | 12/2007 | Schilling et al. |
| 7,371,871 B2 | 5/2008 | Schilling et al. |
| 7,470,700 B2 | 12/2008 | Feng et al. |
| 7,781,584 B2 | 8/2010 | Feng |
| 7,795,428 B2 | 9/2010 | Feng |
| 7,807,689 B2 | 10/2010 | Zhang |
| 7,872,124 B2 | 1/2011 | Feng |
| 7,906,523 B2 | 3/2011 | Feng |
| 2001/0018210 A1 | 8/2001 | Bachovchin et al. |
| 2001/0020006 A1 | 9/2001 | Demuth et al. |
| 2001/0031780 A1 | 10/2001 | Kanstrup et al. |
| 2001/0047078 A1 | 11/2001 | Chang |
| 2001/0051646 A1 | 12/2001 | Demuth et al. |
| 2002/0006899 A1 | 1/2002 | Pospisilik et al. |
| 2002/0016100 A1 | 2/2002 | Okabe et al. |
| 2002/0019411 A1 | 2/2002 | Robl et al. |
| 2002/0037829 A1 | 3/2002 | Aronson et al. |
| 2002/0041871 A1 | 4/2002 | Brudnak |
| 2002/0049153 A1 | 4/2002 | Bridon et al. |
| 2002/0049164 A1 | 4/2002 | Demuth et al. |
| 2002/0061839 A1 | 5/2002 | Scharpe et al. |
| 2002/0071838 A1 | 6/2002 | Demuth et al. |
| 2002/0077340 A1 | 6/2002 | Sulsky et al. |
| 2002/0082292 A1 | 6/2002 | Sahoo et al. |
| 2002/0082427 A1 | 6/2002 | Demuth et al. |
| 2002/0103242 A1 | 8/2002 | Sahoo et al. |
| 2002/0103384 A1 | 8/2002 | Kanstrup et al. |
| 2002/0110560 A1 | 8/2002 | Demuth et al. |
| 2002/0115843 A1 | 8/2002 | Oi et al. |
| 2002/0132979 A1 | 9/2002 | Chen |
| 2002/0147130 A1 | 10/2002 | Huber et al. |
| 2002/0147157 A1 | 10/2002 | Connor |
| 2002/0155565 A1 | 10/2002 | Garin-Chesa et al. |
| 2002/0164759 A1 | 11/2002 | Travis et al. |
| 2002/0165164 A1 | 11/2002 | Demuth et al. |
| 2002/0169159 A1 | 11/2002 | Medina et al. |
| 2002/0183367 A1 | 12/2002 | Sulsky et al. |
| 2002/0193390 A1 | 12/2002 | Villhauer |
| 2002/0198205 A1 | 12/2002 | Himmelsbach et al. |
| 2002/0198242 A1 | 12/2002 | Demuth et al. |
| 2002/0198380 A1 | 12/2002 | Belzer et al. |
| 2003/0008905 A1 | 1/2003 | Demuth et al. |
| 2003/0008925 A1 | 1/2003 | Esteve et al. |
| 2003/0027282 A1 | 2/2003 | Huber et al. |
| 2003/0040478 A1 | 2/2003 | Drucker et al. |
| 2003/0045464 A1 | 3/2003 | Hermeling et al. |
| 2003/0055052 A1 | 3/2003 | Peters et al. |
| 2003/0060412 A1 | 3/2003 | Prouty et al. |
| 2003/0060434 A1 | 3/2003 | Nielsen et al. |
| 2003/0069234 A1 | 4/2003 | Medina et al. |
| 2003/0087935 A1 | 5/2003 | Cheng et al. |
| 2003/0087950 A1 | 5/2003 | DeNanteuil et al. |
| 2003/0089935 A1 | 5/2003 | Fan et al. |
| 2003/0092630 A2 | 5/2003 | Demuth et al. |
| 2003/0092697 A1 | 5/2003 | Cheng et al. |
| 2003/0096846 A1 | 5/2003 | Cheng et al. |
| 2003/0096857 A1 | 5/2003 | Evans et al. |
| 2003/0100563 A1 | 5/2003 | Edmondson et al. |
| 2003/0103968 A1 | 6/2003 | Amelsberg et al. |
| 2003/0105077 A1 | 6/2003 | Kanstrup et al. |
| 2003/0119736 A1 | 6/2003 | Demuth et al. |
| 2003/0119738 A1 | 6/2003 | Niestroj et al. |
| 2003/0119750 A1 | 6/2003 | Demuth et al. |
| 2003/0125304 A1 | 7/2003 | Demuth et al. |
| 2003/0130199 A1 | 7/2003 | von Hoersten et al. |
| 2003/0130281 A1 | 7/2003 | Boehringer et al. |
| 2003/0130306 A1 | 7/2003 | Devasthale et al. |
| 2003/0134802 A1 | 7/2003 | Demuth et al. |
| 2003/0135023 A1 | 7/2003 | Demuth et al. |
| 2003/0139429 A1 | 7/2003 | Cohen et al. |
| 2003/0139434 A1 | 7/2003 | Balkan et al. |
| 2003/0144206 A1 | 7/2003 | Knudsen et al. |
| 2003/0148961 A1 | 8/2003 | Heiser et al. |
| 2003/0149071 A1 | 8/2003 | Gobbi et al. |
| 2003/0153509 A1 | 8/2003 | Bachovchin et al. |
| 2003/0162820 A1 | 8/2003 | Demuth et al. |
| 2003/0166578 A1 | 9/2003 | Arch et al. |
| 2003/0166662 A1 | 9/2003 | Fryburg et al. |
| 2003/0166690 A1 | 9/2003 | Ebdrup et al. |
| 2003/0171358 A1 | 9/2003 | Jeppesen et al. |
| 2003/0171411 A1 | 9/2003 | Kodra et al. |
| 2003/0176357 A1 | 9/2003 | Pospisilik et al. |
| 2003/0181497 A1 | 9/2003 | Chen et al. |
| 2003/0186963 A1 | 10/2003 | Dorwald et al. |
| 2003/0187254 A1 | 10/2003 | Perry et al. |
| 2003/0191112 A1 | 10/2003 | Dorwald et al. |
| 2003/0195188 A1 | 10/2003 | Boehringer et al. |
| 2003/0195190 A1 | 10/2003 | Peschke et al. |
| 2003/0199451 A1 | 10/2003 | Mogensen et al. |
| 2003/0199528 A1 | 10/2003 | Kanstrup et al. |
| 2003/0199563 A1 | 10/2003 | Robl et al. |
| 2003/0199672 A1 | 10/2003 | Knudsen et al. |
| 2003/0203946 A1 | 10/2003 | Behrens et al. |
| 2003/0216382 A1 | 11/2003 | Boehringer et al. |
| 2003/0216450 A1 | 11/2003 | Evans et al. |
| 2003/0220345 A1 | 11/2003 | Hamby et al. |
| 2003/0225102 A1 | 12/2003 | Sankaranarayanan |
| 2003/0232761 A1 | 12/2003 | Hinke et al. |

| | | | | | | |
|---|---|---|---|---|---|---|
| 2003/0236272 | A1 | 12/2003 | Carr | 2006/0135767 A1 | 6/2006 | Feng et al. |
| 2004/0002495 | A1 | 1/2004 | Sher et al. | 2007/0060528 A1 | 3/2007 | Christopher et al. |
| 2004/0002609 | A1 | 1/2004 | Hulin | 2007/0060529 A1 | 3/2007 | Christopher et al. |
| 2004/0006062 | A1 | 1/2004 | Smallheer et al. | 2007/0060530 A1 | 3/2007 | Christopher |
| 2004/0009972 | A1 | 1/2004 | Ding et al. | 2007/0066635 A1 | 3/2007 | Andres et al. |
| 2004/0009998 | A1 | 1/2004 | Dhar et al. | 2008/0003283 A1 | 1/2008 | Feng et al. |
| 2004/0034014 | A1 | 2/2004 | Kanstrup et al. | 2008/0108807 A1 | 5/2008 | Feng |
| 2004/0053369 | A1 | 3/2004 | Abbott et al. | 2008/0108808 A1 | 5/2008 | Feng |
| 2004/0054171 | A1 | 3/2004 | Jensen et al. | 2008/0177064 A1 | 7/2008 | Feng |
| 2004/0058876 | A1 | 3/2004 | Hoffmann et al. | 2008/0275072 A1 | 11/2008 | Ogawa |
| 2004/0063935 | A1 | 4/2004 | Yasuda | 2009/0012059 A1 | 1/2009 | Feng |
| 2004/0072874 | A1 | 4/2004 | Sato et al. | 2011/0087022 A1 | 4/2011 | Feng |
| 2004/0072892 | A1 | 4/2004 | Fukushima et al. | 2011/0192748 A1 | 8/2011 | Christopher |
| 2004/0077645 | A1 | 4/2004 | Himmelsbach et al. | | | |
| 2004/0082497 | A1 | 4/2004 | Evans et al. | FOREIGN PATENT DOCUMENTS | | |
| 2004/0082607 | A1 | 4/2004 | Oi et al. | DE | 2361551 A1 | 6/1975 |
| 2004/0087587 | A1 | 5/2004 | Himmelsbach et al. | DE | 2500024 A1 | 7/1976 |
| 2004/0092478 | A1 | 5/2004 | Rothermel et al. | DE | 2801289 A1 | 5/1979 |
| 2004/0097510 | A1 | 5/2004 | Himmelsbach et al. | DE | 10256264 A | 6/2004 |
| 2004/0106655 | A1 | 6/2004 | Kitajima et al. | EP | 0354549 | 2/1900 |
| 2004/0106656 | A1 | 6/2004 | Ashton et al. | EP | 0378255 A2 | 7/1990 |
| 2004/0106802 | A1 | 6/2004 | Sankaranarayanan et al. | EP | 0378991 A1 | 7/1990 |
| 2004/0110817 | A1 | 6/2004 | Hulin | EP | 0442473 A1 | 8/1991 |
| 2004/0116328 | A1 | 6/2004 | Yoshikawa et al. | EP | 0505893 A1 | 9/1992 |
| 2004/0132713 | A1 | 7/2004 | Hulin et al. | EP | 0547442 A1 | 6/1993 |
| 2004/0132732 | A1 | 7/2004 | Han et al. | EP | 0547514 | 6/1993 |
| 2004/0138148 | A1 | 7/2004 | Fushimi et al. | EP | 0574846 | 12/1993 |
| 2004/0138214 | A1 | 7/2004 | Himmelsbach et al. | EP | 0587377 A2 | 3/1994 |
| 2004/0138215 | A1 | 7/2004 | Eckhardt et al. | EP | 0657452 | 6/1995 |
| 2004/0147434 | A1 | 7/2004 | Ansorge et al. | EP | 0702013 | 3/1996 |
| 2004/0152192 | A1 | 8/2004 | Bachovchin et al. | EP | 0748800 | * 12/1996 |
| 2004/0152745 | A1 | 8/2004 | Jackson et al. | EP | 0570594 | 7/1997 |
| 2004/0166125 | A1 | 8/2004 | Himmelsbach et al. | EP | 0847992 | 6/1998 |
| 2004/0167133 | A1 | 8/2004 | Edmondson et al. | EP | 0900566 A2 | 3/1999 |
| 2004/0167191 | A1 | 8/2004 | Demuth et al. | EP | 0900568 A2 | 3/1999 |
| 2004/0167341 | A1 | 8/2004 | Haffner et al. | EP | 1136482 A1 | 9/2001 |
| 2004/0171104 | A1 | 9/2004 | Blinkovsky et al. | EP | 1197799 A1 | 4/2002 |
| 2004/0171555 | A1 | 9/2004 | Demuth et al. | EP | 1229024 | 8/2002 |
| 2004/0171848 | A1 | 9/2004 | Haffner et al. | EP | 1398032 A1 | 3/2004 |
| 2004/0176406 | A1 | 9/2004 | Gobbi et al. | EP | 1532980 A1 | 5/2005 |
| 2004/0176428 | A1 | 9/2004 | Edmondson et al. | EP | 1586571 A1 | 10/2005 |
| 2004/0180925 | A1 | 9/2004 | Matsuno et al. | FR | 2162106 A1 | 11/1972 |
| 2004/0186153 | A1 | 9/2004 | Yasuda et al. | GB | 699812 | 11/1953 |
| 2004/0198786 | A1 | 10/2004 | Gretzke et al. | GB | 1377642 | 12/1974 |
| 2004/0209891 | A1 | 10/2004 | Broqua et al. | GB | 1441665 A | 7/1976 |
| 2004/0229820 | A1 | 11/2004 | Bachovchin et al. | GB | 1464248 A | 2/1977 |
| 2004/0229848 | A1 | 11/2004 | Demuth et al. | GB | 2143542 A | 9/1986 |
| 2004/0236102 | A1 | 11/2004 | Brockunier et al. | GB | 2230527 A | 10/1990 |
| 2004/0242566 | A1 | 12/2004 | Feng et al. | JP | 9295977 | 11/1997 |
| 2004/0242568 | A1 | 12/2004 | Feng et al. | JP | 2002/338466 | 11/2002 |
| 2004/0242636 | A1 | 12/2004 | Haffner et al. | JP | 2003/128551 | 5/2003 |
| 2004/0242898 | A1 | 12/2004 | Hulin et al. | JP | 2004/099600 A | 4/2004 |
| 2004/0254167 | A1 | 12/2004 | Biftu et al. | JP | 2004/123738 A | 4/2004 |
| 2004/0254226 | A1 | 12/2004 | Feng et al. | WO | WO 89/10701 A1 | 11/1989 |
| 2004/0259843 | A1 | 12/2004 | Madar et al. | WO | WO 91/11457 A1 | 8/1991 |
| 2004/0259870 | A1 | 12/2004 | Feng et al. | WO | WO 91/12001 A1 | 8/1991 |
| 2004/0259883 | A1 | 12/2004 | Sakashita et al. | WO | WO 93/21162 A2 | 1/1993 |
| 2004/0259902 | A1 | 12/2004 | Boehringer et al. | WO | WO 93/08259 A2 | 4/1993 |
| 2004/0259903 | A1 | 12/2004 | Boehringer et al. | WO | WO 93/24634 A1 | 12/1993 |
| 2004/0259919 | A1 | 12/2004 | Magnin et al. | WO | WO 94/03055 A1 | 2/1994 |
| 2005/0004117 | A1 | 1/2005 | Feng et al. | WO | WO 95/15309 A1 | 6/1995 |
| 2005/0014732 | A1 | 1/2005 | Gulve et al. | WO | WO 95/29691 A1 | 11/1995 |
| 2005/0014946 | A1 | 1/2005 | Demuth et al. | WO | WO 95/35031 A1 | 12/1995 |
| 2005/0020574 | A1 | 1/2005 | Hauel et al. | WO | WO 96/02667 A1 | 2/1996 |
| 2005/0026921 | A1 | 2/2005 | Eckhardt et al. | WO | WO 96/32384 A1 | 10/1996 |
| 2005/0032804 | A1 | 2/2005 | Cypes et al. | WO | WO 96/38550 A1 | 12/1996 |
| 2005/0038020 | A1 | 2/2005 | Hamann et al. | WO | WO 97/29776 A1 | 8/1997 |
| 2005/0043292 | A1 | 2/2005 | Parker et al. | WO | WO 97/40832 A1 | 11/1997 |
| 2005/0043299 | A1 | 2/2005 | Evans et al. | WO | WO 98/00439 A2 | 1/1998 |
| 2005/0058635 | A1 | 3/2005 | Demuth et al. | WO | WO 98/18763 A1 | 5/1998 |
| 2005/0065144 | A1 | 3/2005 | Feng et al. | WO | WO 98/19998 A2 | 5/1998 |
| 2005/0065145 | A1 | 3/2005 | Cao | WO | WO 98/24780 A2 | 6/1998 |
| 2005/0065148 | A1 | 3/2005 | Feng et al. | WO | WO 98/50046 A1 | 11/1998 |
| 2005/0070530 | A1 | 3/2005 | Feng et al. | WO | WO 98/51803 A1 | 11/1998 |
| 2005/0070531 | A1 | 3/2005 | Feng et al. | WO | WO 99/02705 A1 | 1/1999 |
| 2005/0070535 | A1 | 3/2005 | Feng et al. | WO | WO 99/16864 A1 | 4/1999 |
| 2005/0070706 | A1 | 3/2005 | Feng et al. | WO | WO 99/17799 A1 | 4/1999 |
| 2005/0075330 | A1 | 4/2005 | Feng et al. | WO | WO 99/18856 A1 | 4/1999 |
| 2005/0261271 | A1 | 11/2005 | Feng et al. | WO | WO 99/28474 A2 | 6/1999 |

| | | | | | | |
|---|---|---|---|---|---|---|
| WO | WO 99/38501 | C2 | 8/1999 | WO | WO 03/002531 A2 | 1/2003 |
| WO | WO 99/46272 | A1 | 9/1999 | WO | WO 03/002553 A2 | 1/2003 |
| WO | WO 99/47152 | A1 | 9/1999 | WO | WO 03/002596 A2 | 1/2003 |
| WO | WO 99/50249 | A2 | 10/1999 | WO | WO 03/004496 A1 | 1/2003 |
| WO | WO 99/52893 | | 10/1999 | WO | WO 03/004498 A1 | 1/2003 |
| WO | WO 99/61431 | A1 | 12/1999 | WO | WO 03/007888 A2 | 1/2003 |
| WO | WO 99/62914 | A1 | 12/1999 | WO | WO 03/010197 A2 | 2/2003 |
| WO | WO 99/67278 | A1 | 12/1999 | WO | WO 03/010314 A2 | 2/2003 |
| WO | WO 99/67279 | A1 | 12/1999 | WO | WO 03/011807 A1 | 2/2003 |
| WO | WO 00/07617 | A1 | 2/2000 | WO | WO 03/011814 A1 | 2/2003 |
| WO | WO 00/09666 | A2 | 2/2000 | WO | WO 03/011892 A2 | 2/2003 |
| WO | WO 00/10549 | A1 | 3/2000 | WO | WO 03/014318 A2 | 2/2003 |
| WO | WO 00/15211 | A2 | 3/2000 | WO | WO 03/015775 A1 | 2/2003 |
| WO | WO 00/20416 | A1 | 4/2000 | WO | WO 03/016335 A2 | 2/2003 |
| WO | WO 00/76986 | A1 | 4/2000 | WO | WO 03/017936 A2 | 3/2003 |
| WO | WO 00/34241 | A1 | 6/2000 | WO | WO 03/022871 A2 | 3/2003 |
| WO | WO 00/40583 | A2 | 7/2000 | WO | WO 03/024942 A1 | 3/2003 |
| WO | WO 00/43366 | A1 | 7/2000 | WO | WO 03/024965 A2 | 3/2003 |
| WO | WO 00/47219 | A2 | 8/2000 | WO | WO 03/053330 A2 | 3/2003 |
| WO | WO 00/53171 | A1 | 9/2000 | WO | WO 03/026652 A1 | 4/2003 |
| WO | WO 00/56296 | A2 | 9/2000 | WO | WO 03/027080 A1 | 4/2003 |
| WO | WO 00/56297 | A2 | 9/2000 | WO | WO 03/030946 A1 | 4/2003 |
| WO | WO 00/57721 | A2 | 10/2000 | WO | WO 03/033524 A2 | 4/2003 |
| WO | WO 01/14318 | A2 | 3/2001 | WO | WO 03/033671 A2 | 4/2003 |
| WO | WO 01/16301 | A1 | 3/2001 | WO | WO 03/035057 A1 | 5/2003 |
| WO | WO 01/19866 | A1 | 3/2001 | WO | WO 03/035067 A1 | 5/2003 |
| WO | WO 01/23364 | A1 | 4/2001 | WO | WO 03/035640 A1 | 5/2003 |
| WO | WO 01/34594 | A1 | 5/2001 | WO | WO 03/037327 A1 | 5/2003 |
| WO | WO 01/40180 | A2 | 6/2001 | WO | WO 03/037888 A1 | 5/2003 |
| WO | WO 01/52825 | A2 | 7/2001 | WO | WO 03/038123 A2 | 5/2003 |
| WO | WO 01/55105 | A1 | 8/2001 | WO | WO 03/040114 A1 | 5/2003 |
| WO | WO 01/55119 | * | 8/2001 | WO | WO 03/040174 A2 | 5/2003 |
| WO | WO 01/55119 | A2 | 8/2001 | WO | WO 03/045228 A2 | 6/2003 |
| WO | WO 01/56988 | A1 | 8/2001 | WO | WO 03/045977 A2 | 6/2003 |
| WO | WO 01/62266 | A2 | 8/2001 | WO | WO 03/048081 A2 | 6/2003 |
| WO | WO 01/68603 | A2 | 9/2001 | WO | WO 03/048158 A1 | 6/2003 |
| WO | WO 01/70729 | A1 | 9/2001 | WO | WO 03/051848 A2 | 6/2003 |
| WO | WO 01/72290 | A2 | 10/2001 | WO | WO 03/055881 A1 | 7/2003 |
| WO | WO 01/74299 | A2 | 10/2001 | WO | WO 03/057144 A2 | 7/2003 |
| WO | WO 01/79206 | A1 | 10/2001 | WO | WO 03/057200 A2 | 7/2003 |
| WO | WO 01/81304 | A1 | 11/2001 | WO | WO 03/057666 A2 | 7/2003 |
| WO | WO 01/81337 | A1 | 11/2001 | WO | WO 03/063903 A2 | 8/2003 |
| WO | WO 01/89569 | A1 | 11/2001 | WO | WO 03/065983 A2 | 8/2003 |
| WO | WO 01/94597 | A1 | 12/2001 | WO | WO 03/068748 A1 | 8/2003 |
| WO | WO 01/96295 | A2 | 12/2001 | WO | WO 03/068757 A1 | 8/2003 |
| WO | WO 01/97808 | A1 | 12/2001 | WO | WO 03/072197 A1 | 9/2003 |
| WO | WO 02/02560 | A2 | 1/2002 | WO | WO 03/072556 A1 | 9/2003 |
| WO | WO 02/04610 | A2 | 1/2002 | WO | WO 03/074500 A2 | 9/2003 |
| WO | WO 02/08931 | A1 | 1/2002 | WO | WO 03/076393 A1 | 9/2003 |
| WO | WO 02/09716 | A2 | 2/2002 | WO | WO 03/076414 A2 | 9/2003 |
| WO | WO 02/14271 | A1 | 2/2002 | WO | WO 03/076418 A1 | 9/2003 |
| WO | WO 02/20488 | A2 | 3/2002 | WO | WO 03/077935 A1 | 9/2003 |
| WO | WO 02/20804 | A1 | 3/2002 | WO | WO 03/080070 A2 | 10/2003 |
| WO | WO 02/26703 | A1 | 4/2002 | WO | WO 03/080633 A1 | 10/2003 |
| WO | WO 02/28742 | A1 | 4/2002 | WO | WO 03/082817 A2 | 10/2003 |
| WO | WO 02/30890 | A1 | 4/2002 | WO | WO 03/082859 A1 | 10/2003 |
| WO | WO 02/30891 | A1 | 4/2002 | WO | WO 03/082898 A2 | 10/2003 |
| WO | WO 02/31134 | A2 | 4/2002 | WO | WO 03/084940 A1 | 10/2003 |
| WO | WO 02/34242 | A2 | 5/2002 | WO | WO 03/092605 A2 | 11/2003 |
| WO | WO 02/34900 | A1 | 5/2002 | WO | WO 03/099279 A1 | 12/2003 |
| WO | WO 02/38541 | A1 | 5/2002 | WO | WO 03/099286 A1 | 12/2003 |
| WO | WO 02/38742 | A2 | 5/2002 | WO | WO 03/099818 A1 | 12/2003 |
| WO | WO 02/051836 | A1 | 7/2002 | WO | WO 03/101449 A2 | 12/2003 |
| WO | WO 02/053170 | A2 | 7/2002 | WO | WO 03/101958 A2 | 12/2003 |
| WO | WO 02/059301 | A1 | 8/2002 | WO | WO 03/104207 A2 | 12/2003 |
| WO | WO 02/059343 | A2 | 8/2002 | WO | WO 03/104208 | 12/2003 |
| WO | WO 02/062764 | C2 | 8/2002 | WO | WO 03/104229 | 12/2003 |
| WO | WO 02/066627 | A1 | 8/2002 | WO | WO 03/106416 A2 | 12/2003 |
| WO | WO 02/068420 | A1 | 9/2002 | WO | WO 03/106456 A2 | 12/2003 |
| WO | WO 02/076450 | A1 | 10/2002 | WO | WO 2004/002535 A1 | 1/2004 |
| WO | WO 02/083109 | A1 | 10/2002 | WO | WO 2004/002986 A2 | 1/2004 |
| WO | WO 02/083128 | A1 | 10/2002 | WO | WO 2004/004655 A2 | 1/2004 |
| WO | WO 02/092127 | A1 | 11/2002 | WO | WO 2004/004661 A2 | 1/2004 |
| WO | WO 02/094178 | A2 | 11/2002 | WO | WO 2004/004665 A2 | 1/2004 |
| WO | WO 02/096357 | A1 | 12/2002 | WO | WO 2004/007446 | 1/2004 |
| WO | WO 03/000180 | A2 | 1/2003 | WO | WO 2004/007468 | 1/2004 |
| WO | WO 03/000181 | A2 | 1/2003 | WO | WO 2004/011640 | 2/2004 |
| WO | WO 03/000250 | A1 | 1/2003 | WO | WO 2004/014860 A2 | 2/2004 |
| WO | WO 03/002530 | A2 | 1/2003 | WO | WO 2004/017989 A1 | 3/2004 |

| | | |
|---|---|---|
| WO | WO 2004/018467 A2 | 3/2004 |
| WO | WO 2004/018468 A2 | 3/2004 |
| WO | WO 2004/018469 A1 | 3/2004 |
| WO | WO 2004/020407 A1 | 3/2004 |
| WO | WO 2004/024184 A1 | 3/2004 |
| WO | WO 2004/026822 A2 | 4/2004 |
| WO | WO 2004/028524 A1 | 4/2004 |
| WO | WO 2004/031175 A2 | 4/2004 |
| WO | WO 2004/031374 A2 | 4/2004 |
| WO | WO 2004/032836 A2 | 4/2004 |
| WO | WO 2004/032861 A2 | 4/2004 |
| WO | WO 2004/033455 A2 | 4/2004 |
| WO | WO 2004/037169 A2 | 5/2004 |
| WO | WO 2004/037176 A2 | 5/2004 |
| WO | WO 2004/037181 A2 | 5/2004 |
| WO | WO 2004/041795 A1 | 5/2004 |
| WO | WO 2004/043940 A1 | 5/2004 |
| WO | WO 2004/046106 A1 | 6/2004 |
| WO | WO 2004/048352 A2 | 6/2004 |
| WO | WO 2004/050022 A2 | 6/2004 |
| WO | WO 2004/050656 A1 | 6/2004 |
| WO | WO 2004/050658 A1 | 6/2004 |
| WO | WO 2004/052850 A2 | 6/2004 |
| WO | WO 2004/058266 A1 | 7/2004 |
| WO | WO 2004/062613 A2 | 7/2004 |
| WO | WO 2004/064778 A2 | 8/2004 |
| WO | WO 2004/067509 A1 | 8/2004 |
| WO | WO 2004/069162 A2 | 8/2004 |
| WO | WO 2004/071454 A2 | 8/2004 |
| WO | WO 2004/075815 A2 | 9/2004 |
| WO | WO 2004/075891 A1 | 9/2004 |
| WO | WO 2004/076401 A1 | 9/2004 |
| WO | WO 2004/076433 A1 | 9/2004 |
| WO | WO 2004/076434 A1 | 9/2004 |
| WO | WO 2004/078777 A2 | 9/2004 |
| WO | WO 2004/080958 A2 | 9/2004 |
| WO | WO 2004/082599 A2 | 9/2004 |
| WO | WO 2004/083212 A1 | 9/2004 |
| WO | WO 2004/085408 A1 | 10/2004 |
| WO | WO 2004/085661 A2 | 10/2004 |
| WO | WO 2004/087053 C2 | 10/2004 |
| WO | WO 2004/087650 A2 | 10/2004 |
| WO | WO 2004/087880 A2 | 10/2004 |
| WO | WO 2004/089362 A1 | 10/2004 |
| WO | WO 2004/096806 A1 | 11/2004 |
| WO | WO 2004/098625 A2 | 11/2004 |
| WO | WO 2004/099134 A2 | 11/2004 |
| WO | WO 2004/099185 A1 | 11/2004 |
| WO | WO 2004/101514 A1 | 11/2004 |
| WO | WO 2004/103276 A2 | 12/2004 |
| WO | WO 2004/103993 A1 | 12/2004 |
| WO | WO 2004/104215 A2 | 12/2004 |
| WO | WO 2004/104216 A2 | 12/2004 |
| WO | WO 2004/110436 A1 | 12/2004 |
| WO | WO 2004/111041 A1 | 12/2004 |
| WO | WO 2004/111051 A1 | 12/2004 |
| WO | WO 2004/112701 A2 | 12/2004 |
| WO | WO 2005/000846 A1 | 1/2005 |
| WO | WO 2005/000848 A1 | 1/2005 |
| WO | WO 2005/003135 A1 | 1/2005 |
| WO | WO 2005/004906 A2 | 1/2005 |
| WO | WO 2005/011581 A2 | 2/2005 |
| WO | WO 2005/012249 A2 | 2/2005 |
| WO | WO 2005/016911 A1 | 2/2005 |
| WO | WO 2005/019168 A2 | 3/2005 |
| WO | WO 2005/095381 A1 | 10/2005 |
| WO | WO 2007/033265 | 3/2007 |
| WO | WO 2007/033266 | 3/2007 |
| WO | WO 2007/033350 | 3/2007 |
| WO | WO 01/70675 A2 | 9/2007 |

OTHER PUBLICATIONS

Sederaviciute et al., CAPLUS Abstract 125:300937 (1996).
Abdel-Fattah et al. Indian Journal of Heterocyclic Chemistry (1999), 8(3), 177-182. (Abstract, 2 pages).
Abdel-Rahman, R. M.: Synthesis of some new fluorine bearing trisubstituted 3-thioxo-1, 2, 4-triazin-5-ones as potential anticancer agents: Farmaco, Edizione Scientifica, Societa Chimica Italiana, Pavia, IT, vol. 47, No. 3 (Mar. 1992), pp. 319-326, XP008000322.
Abstract of Barnela et al. HCAPLUS Accesssion No. 1987:138384 Indian Journal of Chemistry Section B: Organic Chemistry Including Medicinal Chemistry (1986), 25B(7), 709-11. (Abstract 2 pages).
Abstract of Barnickel et al. STN Printout (one page). Accession No. 1996:12269. Abstract of WO 06/23364.
Abstract of Lakhan et al. Journal of Indian Chemical Society (1987), 64 (5), 316-18 (2 pages).
Abstract of Shyam et al. Current Science (1975), 44(16), 572-4 (one page).
Abstract of Tiwari et al. Indian of Journal of Pharmaceutical Sciences (1978), 40(2), 40-3 (2 pages).
Abstract of Pattanaik et al. Indian Journal of Chemistry, Section B; Organic Chemistry including Medicinal Chemistry (1998), 37B (12), 1304-1306 from STN CAS online search printout (3 pages).
Akahoshi, F. et al.: "Synthesis and pharmacological activitey of ||riazole[1,5-a]triazine derivatives inhibiting eosinophilia." Journal of Medicinal Chemistry, vol. 41, No. 16, (Jul. 30, 1998), pp. 2985-2993, XP002390903.
Alagarsamy, V. et al. "Synthesis and pharmacological investigation . . . " Pharmazie, vol. 57, No. 5 2002, pp. 306-307, XP008084498.
Algarsamy, V. et al. "Synthesis, analgesic, antii-inflammatory . . . " Bio & Pharm. Bulletin of Japan, Pharma society of JP, vol. 25, No. 11, 2002, pp. 1432-1435, XP008084513 ISSN: 0918-6158.
Argaud, Doriane et al., Metaformin decreases gluconeogenesis by enhancing the pyruvate kinase flux in isolated rat hepatocytes, European J. Biochem. 213, 1341-1348 (1993).
Ashcroft, Stephen J.H. et al., Structure-activity relationships of alloxan-like compounds derived from uric acid, Br. J. Pharmac. (1986), 89 pp. 469-472.
Bahaji E-H et al. Database Biosis [Online] Biosciences Information Service, Philadelphia, PA, US; 1991,: "Studies on Immunostimulating Derivatives Synthesis of Some Pyrrolo-1 2-C-Pyrimidines" XP002392081. Database accession No. PREV199192140000 abstract.
Baker, B.R. et al., Irreversible Enzyme Inhibitors. On the Mode of Pyrimidine Binding of 5-alkyl and 5-Arylpyrimidines to Dihydrofolic Reductase (1,2), Journal of Heterocyclic Chemistry vol. 4 (1967) pp. 39-48.
Bal, Gunther, Dipeptidyl Peptidase IV and Prolyl Oligopeptidase: Design, Synthesis and Evaluation of Substrates and Inhibitors, (2002) Universiteit Antwerpen.
Banker, G.S. et al, "Modern Pharmaceutices, 3$^{rd}$ edition", Marcel Dekker, New York, 1996, pp. 451 and 596.
Barakat, S.E.S., Synthesis and hypoglycemic activity of some new 3-[4-[[[(cyclohexylamino) carbonyl] amino]sulfony]phenyl]-4(3H)-quinazolinones, Az. J. Pharm. Sci., vol. 25, (2000), pp. 48-57.
Barakat, S.E.S., Synthesis and Hypoglycemic Activity of Some New 4(3H)-Quinazolinone Analogues, Saudi Pharmaceutical Journal, vol. 8, No. 4 (2000) pp. 198-204.
Belgodere, Elena et al., Synthesis of Substituted Pyrimidines, Study of the Structure and of the Tautomeric Equilibria, (1976) Chem. Abstracts, Columbus, OH vol. 85 No. 9. XP002298337.
Bhaduri, A.P. et al., Urinary Metabolite of 2-Piperazino-3 (H)-4-Quinazolone (Centpiperalone), A Potent Blood Sugar Lowering Agent, Indian J. Biochem. Biophys., vol. 12 (1975), pp. 413-414.
Borrell, J. I. et al.: "Synthesis, structure and cytotoxicity evaluation of palladium(II) complexes of 4-amino-3-hydrazino-1,2,4-triazin-5(4h)-on es and 4-amino-3-(n-methylhydrazino)-1,2,4-triazi N-5(4H)-ones" Anales De Quimica, vol. 91, No. ¾, 1995, pp. 243-252, XP008000323.
Botta, M., Saladino, R., Lamba, D. Nicoletti, R.: Researches on Antiviral Agents. 31. Synthesis and Transformations of Racemic and Chiral 6-Oxiranyl Pyrimidinones, Tetrahedron, vol. 49, 1993, pp. 6053-6070, XP002329846.
Bouras, Mohammed, et al., Metabolism of enterostatin in rat intestine, brain, membranes and serum: differential involvement of proline-specific peptidases, Peptides, vol. 16, No. 3, (1995), pp. 399-405.
Brun, Jean-Frederic, et al., Effects of Oral Zinc Gluconate on Glucose Effectiveness and Insulin Sensitivity in Humans, Biological Trace Element Research vol. 47 (1995), pp. 385-391.

Buckley, Di, Analysis of the Degradation of Insulinotropin [GLP-1 (7-37)] in Human Plasma and Production of Degradation Resistant Analogs.
Buysens, K. J. et al.: "Synthesis of New Pyrrolo[3,4-b]- and [3,4-c]∥uinazol(on)es and related 1,7-Naphthyridinones and 2,7-naphthyridines via intramolecular diels-alder reactions of 2(1H)-pyrazinones" Tetrahedron, Elsevier Science Publishers, Amsterdam, NL, vol. 52, No. 27, (Jul. 1, 1996), pp. 9161-9178, XP004104003.
Caira M R: "Crystalline Polymorphism of Organic Compounds" Topics in Current Chemistry, Springer, Berlin, DE, vol. 198, 1998, pp. 163-208, XP001156954 ISSN: 0340-1022 p. 165.
Callebaut, Christian et al. "T Cell Activation Antigien, CD26, as a Cofactor of Entry of HIV in CD4+ Cells" Science, (1993), vol. 262, pp. 2045-2050.
Cecil Textbook of Medicine, edited by Bennet, J.C., and Plum F., 20$^{th}$ edition, vol. 1, 1004-10, 1996.
Chatterjee, A.K. et al., Effect of Centpiperalone, a New Hypoglycemic Agent on Insulin Biosynthesis & Release from Isolated Pancreatic Islets of Rat, Indian Journal of Experimental Biology vol. 20 (1981) pp. 270-272.
Chatterjee, A.K. et al., Effect of Centpiperalone in Insulin Deficient Diabetes, Indian Journal of Experimental Biology vol. 18 (1980), pp. 1005-1008.
Chenard et al. J. Med Chem. 2001, 44, 1710-1717.
Cheng, Hung-Chi et al. "Lung Endothelial Dipeptidyl Peptidase IV Promoted Adhesion and Metastasis of Rat Brest Cancer Cells via Tumor Cell Surface-associated Gibronectin" J. of Bio. Chem., (1998), vol. 273, No. 37, pp. 24207-24215.
Coppola, Gary M. et al., 1-Aminomethylisoquinoline-4-carboxylates as Novel Dipeptidylpeptidase IV Inhibitors, Bioorganic & Medicinal Chemistry Letters vol. 10 (2000), pp. 1555-1558.
Database Beilstein [online] Beilstein Corssfire Institut Zur Foerderung Der Chemischen Wissenschaften, DE; 1989 XP002392086. Database Accession No. BRN 5951213 abstract.
Database Beilstein [online] Beilstein Crossfire Institut Zur Foerderung Der Chemischen Wissenschaften, DE; 1924, XP002392085. Database Accession No. BRN 3799088 abstract.
Database Beilstein [online] Beilstein Crossfire Institut Zur Foerderung Der Chemischen Wissenschaften, DE; 1960 XP002392087. Database Accession No. BRN 609897 abstract.
Database Beilstein [online] Beilstein Crossfire Institut Zur Foererung Der Chemischen Wissenschaften DE; 1974 XP002392089. Database Accession No. BRN 514343 abstract.
Database Beilstein [online] Beilstein Crossfire Institut Zur Foerderung Der Chemischen Wissenschaften, DE; 1993 XP002392088. Database Accession No. BRN 6139401 abstract.
Database Beilstein [online] Beilstein Crossfire Institut Zur Foerderung Der Chemischen Wissenschaften, DE; Citation No. 5593678 1991, XP00239083.
Database CA [online] Chemical Abstract service, Columbus, Ohio, US; Reg No. 102482-94-0 Liu, Gang: "Fungal endophyte-epichloe and its secondary metabolites" XP002392084. Database Accession No. 2004:340837 abstract.
Database Crossfire Beilstein Institut zur Foerderung der Wissenchaften, Frankfurt am Main, DE; XP002335066. Database Accession No. 386682 & J.Chem.Soc., 1952, pp. 4985-4990.
Database Crossfire Beilstein Institut zur Foerderung der Wissenchaften, Frankfurt am Main, DE; XP002335067. Database Accession No. 389575 & Chem.Ber., vol. 88, 1968, pp. 106-109.
Database Crossfire Beilstein Institut zur Foerderung der Wissenchaften, Frankfurt am Main, DE; XP002335074. Database Accession No. 392446, J.Heterocycl.Chem., vol. 8, 1971, pp. 367-371.
Database Crossfire Beilstein Institut zur Foerderung der Wissenchaften, Frankfurt am Main, DE; XP002335068. Database Accession No. 472441 & Yakugaku Zasshi, vol. 88, 1968, pp. 106-109.
Database Crossfire Beilstein Institut zur Foerderung der Wissenchaften, Frankfurt am Main, DE; XP002335076. Database Accession No. 490809, & Angew.Chem., vol. 84, 1972, p. 1185.
Database Crossfire Beilstein Institut zur Foerderung der Wissenchaften, Frankfurt am Main, DE; XP002335072. Database Accession No. 990008, J.Prakt.Chem., vol. 315, 1973, pp. 1166-1168.
Database Crossfire Beilstein Institut zur Foerderung der Wissenchaften, Frankfurt am Main, DE; XP002335065. Database Accession No. 1447134 & J.Org.Chem., vol. 43, 1978, pp. 4069-4074.
Database Crossfire Beilstein Institut zur Foerderung der Wissenchaften, Frankfurt am Main, DE; XP002335069. Database Accession No. 1447840 & Chem.Ber., vol. 101, No. 8, 1968, pp. 2679-2689.
Database Crossfire Beilstein Institut zur Foerderung der Wissenchaften, Frankfurt am Main, DE; XP002335064. Database Accession No. 1447881 & J. Heterocycl.Chem., vol. 305, 1972, pp. 724-730.
Database Crossfire Beilstein Institut zur Foerderung der Wissenchaften, Frankfurt am Main, DE; XP002335070. Database Accession No. 1448669 & Chem.Ber., vol. 101, No. 8, 1968, pp. 2679-2689.
Database Crossfire Beilstein Institut zur Foerderung der Wissenchaften, Franfurt am Main, DE: XP002335063. Database-Accession No. 1525341 & J. Heterocycl.Chem., vol. 12, 1975, pp. 683-687.
Database Crossfire Beilstein Institut zur Foerderung der Wissenchaften, Frankfurt am Main, DE; XP002335075. Database Accession No. 4742608, J. Prakt.Chem., vol. 333, No. 1, 1991, pp. 149-151.
Database Crossfire Beilstein Institut zur Foerderung der Wissenchaften, Frankfurt am Main, DE; XP002335071. Database Accession No. 4991064, J.Chem.Soc.Perkin Trans.1, 1980, pp. 1370-1380.
Database Crossfire Beilstein Institut zur Foerderung der Wissenchaften, Frankfurt am Main, DE; XP002335073. Database Accession No. 6219070, J.Prakt.Chem., vol. 330, No. 2, 1988, pp. 323-324.
Database Beilstein [online] Beilstein Crossfire Institut Zur Forderung Der Chemischen Wissenschaften, DE; 1991, XP002392082. Database Accession No. BRN 5340228 abstract.
Deacon, Carolyn F. et al., Both Subcutaneously and Intravenously Administered Glucagon-Like Peptide I Are Rapidly Degraded From the $NH_2$-Terminus in Type II Diabetic Patients and in Healthy Subjects, Diabetes, vol. 44 (1996), pp. 1125-1131.
Deacon, Carolyn F. et al., Degradation of Glucagon-Like Peptide 1 in Vitro Yields an N-Terminally Truncated Peptide That is a Major Endogenous Metabolite in Vivo, Journal of Clinical Endocrinology and Metabolism vol. 80, No. 3 (1995), pp. 952-957.
Deacon, Carolyn F. et al., Dipeptidyl peptidase IV Inhibition Influences GLP-1 Metabolism in Vivo, Regulatory Peptides vol. 64 Issues 1-3 (1996) p. 30.
Deacon, Carolyn F. et al., Dipeptidyl peptidase IV Inhibition Potentiates the Insulinotropic Effect of Glucagon-Like Peptide 1 in the Anesthetized Pig, Diabetes, vol. 47 (1998), pp. 764-769.
Deacon, Carolyn F. et al., Dipeptidyl peptidase IV Inhibition as an Approach to the Treatment and Prevention of Type 2 Diabetes: a Historical Perspective, Biochemical and Biophysical Research Communications 294 (2002), pp. 1-4.
Demuth, Hans-Ulrich et al., Rebuttal to Deacon and Holst: "Metaformin effects on ∥uinazolin peptidase IV degradation of glucagons-like peptide-1" versus "dipeptidyl peptidase inhibition as an approach to the treatment and prevention of type 2 diabetes: a historical perspective" Biochemical and Biophysical Research Communications 296 (2002) pp. 229-232.
Desai N C et al "Synthesis and anti-Hiv . . . " Indian Journal of Experimental Bio.,vol. 36, No. 12, 1998 pp. 1280-1283, XP008084509 ISSN: 0019-5889.
Dey, Paramita D., et al., Regioselective [4+2] Cycloaddition versus Nucleophilic Reactions of N-Arylamino Substituted 1,3-Diaza-1,3-Butadienes with Ketenes: Synthesis of Pyrimidinone and Fused Pyrimidione Derivatives. Part II. Tetrahedron, vol. 53, No. 40, pp. 13829-13840, 1997.
Dumas, Donald J. "Total synthesis of peramine" Journal of Organic Chemistry, American Chemical Society, Easton, US, vol. 5, 1988, pp. 4650-4653, XP002087391.
Engel, Michael et al., The crystal structure of dipeptidyl peptidase IV (CD26) reveals its functional regulation and enzymatic mechanism, Proc. Nat. Acad. Sci. Early Edition (2003), pp. 1-6.
EP 900568A2 Abstract from STN CAS online search printout (3 pages).
Fantus et al "Mechanism of Action . . . " Journal of Clinical. Endocrin. and Metabol. vol. 63, No. 4, pp. 898-905.

Felczak et al. Database Crossfire Beilstein Institut Zur Foerderung Der Chmischen Wissenschaften. XP002310121. Beilstein Registry No. 7289032 & Nucleosides Nucleotides, vol. 14, No. 3-5, 1995, pp. 653-656.

Fraisse, L., et al. Long-Chained Substituted Uric Acid and 5,6-Diaminouracil Derivatives as Novel Agents against Free Radical Processes: Synthesis and in Vitro Activity, Journal of Medicinal Chemistry, vol. 36, 1993, pp. 1456-1473, XP002329847.

Fraser & Kermack "The Reaction of Paludrine (Proguanil) with Ethyl Acetoacetate" 1951 pp. 2682-2686.

Garratt, Peter J. et al., One-Carbon Compounds as Synthetic Intermediates. The Synthesis of Hydropyrimidines and Hydroquinazolines by Sequential Nucleophilic Addition to Diphenyl Cyanocarbonimidate With Concomitant Cyclization, J. Org. Chem. (1988), pp. 1062-1069.

Garratt, Peter J. et al., A Novel Synthesis of Dihydropyrimidines, J. Chem. Soc., Chem. Commun. (1987), pp. 568-569. XP002298336.

Gazit, Aviv et al., Tyrphostins IV—Highly Potent Inhibitors of EGF Receptor Kinase. Structure-Activity Relationship Study of 4-Anilidoquinazolines, Bioorganic & Medicinal Chemistry, vol. 4, No. 8 (1996) pp. 1203-1207.

Green et al., Expert Opin. Emergin Drugs, 11(3); 525-539, 2006.

Guerrieri, N., et al., Vanadium Inhibition of Serine and Cysteine Proteases, Comparative Biochemistry and Physiology Part A 122 (1997), pp. 331-336.

Gupta, A. et al.: "Fluorine containing Biologically Active Agents: Synthesis of some new Pyrimidine Derivatives" J.Ind. Chem.Soc., vol. 71 1994, pp. 635-636, XP000889664 compound 1.

Gupta, C.M. et al., A Novel Class of Hypoglycaemic Agents: Syntheses & SAR in 2-Substituted 4(3H)-Quinazolones, 2-Substituted 4-Hydroxypolymethylene 5,6]pyrimidines & 3-Substituted 4-Oxo-pyrido [I,2-a] pyrimidines, Indian Journal of Chemistry, vol. 9 (1971), pp. 201-206.

Gupta, C.M. et al., Drugs Acting on the Central Nervous System. Syntheses of Substituted Quinazolones and Quinazolines and Triazepino-and Triazocionquinazolones, Division of Medicinal Chemistry, Central Drug Research Institute, Lucknow, India (1967), pp. 392-395.

Hamid et al. Scientia Pharmaceutica (2001), 69(4), 351-366.

Hcaplus 121: 35089 Snider, Barry B. et al. Tetrahedron Ltrs 1994 35(4) 531-4.

Hcaplus 122: 132810 Snider, Barry B. et al. Jornal of Organic Chem. 1994, 59(26) 8065-70.

Hermecz, Istvan et al., Pyrido[1,2-a]Pyrimidines; New Chemical Entities in Medicinal Chemistry, Medicinal Research Reviews, vol. 8, No. 2 (1988) pp. 203-230.

Hildebrandt, Martin et al. "A guardian angel: the involvement of dipeptidyl peptidase IV in psychoneuroendocrine function, nutrition and immune defence" Clinical Science, (2000), vol. 99, pp. 93-104.

Hinke, Simon A. et al., Metaformin Effects on Dipeptidylpeptidase IV Degradation of Glucagon-like Peptide-1, Biochemical and Biophysical Research Communications, 291 (2002) pp. 1302-1308.

Hinke, Simon A. et al., On Combination Therapy of Diabetes With Metaformin and Dipeptidyl Peptidase IV Inhibitors, Diabetes Care, vol. 25, No. 8 (2002) pp. 1490-1492.

Holz, George G. et al, Pancreatic Beta-Cells are Rendered Glucose-Competent by the Insulinotropic Hormone Glucagon-Like Peptide-1(7-37), Nature, vol. 361 (1993), pp. 362-365.

Jakubkiene, Virginija, et al., (G-Methyl-2methylsulfanyl-4-oxo-3,4-dihydro-3-pyrimidinyl)acetic acid and related compounds exhibiting anti-inflammatory activity. Pharmazie 57 (2002) 9, pp. 610-613.

Jones, Terence R., et al., Azafluorenes Containing Two Bridgehead Nitrogen Atoms. Journal of the Chemical Society, Perkin Transactions 1, No. 12, Dec. 1987, pp. 2585-2592.

Kamata et al., CAPLUS Abstract 105: 191027, 1986 Chemical & Pharma Bulletin (1985), 33(8), 3160-75.

Kazuo, M. et al. "Reaction of Copper (II) Complexes Optically . . . " J. Chem. Soc. Dalton Trans. 1987, pp. 1127-1132, XP008082357.

Kesarwani, A. P. et al.: Solid-phase synthesis of ||uinazoline-(3H)-ones with three-point diversity, Tetrahedron Letters, vol. 43, (2002) pp. 5579-5581.

Khalid, Noraini M., et al., Purification and Partial Characterization of a Prolyl-Dipeptidyl Aminopeptidase From *Lactobacillus helveticus* CNRZ 32, Applied and Environmental Microbiology (1990), pp. 381-388.

Kieffer, Timothy J. et al., Degradation of Glucose-Dependant Insulinotropic Polypeptide and Truncated Glucagon-Like Peptide 1 in Vitro and in Vivo by Dipeptidyl Peptidase IV, Endocrinology, vol. 136, No. 8 (1995) 3585-3596.

Kim, H.O. et al., Structure-Activity Relationships of 1,3-Dialkylxanthine Derivatives at Rat $A_3$ Adenosine Receptors, Journal of Medicinal Chemistry, vol. 37, 1994, pp. 3373-3382, XP002329848.

Kimura, Toshikiro et al., Oral Administration of Insulin as Poly(Vinyl Alcohol)-Gel Spheres in Diabetic Rats, Biological & Pharmaceutical Bulletin, vol. 19, No. 6 (1996), 897-900.

Kobe, J. et al.: "The synthesis of s-triazolo[4.3-a]1,3,5-triazines" Tetrahedron, Elsevier Science Publishers, Amsterdam, NL, vol. 26, Jul. 1970, pp. 3357-3368, XP002390908.

Koreeda, Yuji et al. "Isolation and characterization of dipeptidyl peptidase IV from *Prevotella loescheii* ATCC 15930" Archives of Oral Biology, vol. 46, 2001, 759-766.

Kotani, T. et al., "Highly selective aldose reductase . . . " Journal of Medicinal Chem., American Chem. Society. Washington, US, vol. 40, No. 5, 1997, pp. 684-694 XP000652330.

Kotra, L. P. et al.: "4-Azido-2-pyrimidone Nucleosides and Related Chemistry" Journal of Organic Chemistry, American Chemical Society. Easton, US, vol. 62, 1997, pp. 7267-7271, XP002390905.

Kozhevnikov et al. Tr. Perm. Sel.-Khoz. Inst. (1971), No. 79, 66-72 From ref. Zh., Khim. 1972, Abstr. No. 9Zh404 Journal (English Abstract attached).

Kusar, Mihael et al., Diethyl N,N-Dimethylaminomethylenemalonate in the Synthesis of Fused Heterocyclic Systems, Heterocyclic Chem. 33 (1996) pp. 1041-1046.

Lambeir, Anne-Marie et al. "Dipeptidyl-Peptidase IV from Bench to Bedside: An Update of Structural Properties, Functions, and Clinical Aspects f the Enzyme DPPIV" Clinical Reviews in Clinical Laboratory sciences, (2003), vol. 40(3), pp. 209-294.

Lin et al., CAPLUS Abstract 104:65665, 1986 Journal of Medicinal Chem. (1986) , 29(1), 84-9.

Lin, Jian, Total Synthesis and Biological Evaluation of Fluoroolefin-containing Dipeptidyl Isosteres as Inhibitors of Dipeptidyl Peptidase IV (CD26), Dissertation presented to State University of New York at Albany, Department of Chemistry (1998).

Li Jinping, et al., Permolybdate and Pertungstate—Potent Stimulators of Insulin Effects in Rat Adipocytes: Mechanism of Action, Biochemistry, 34 (1995) 6218-6225.

Loeser, Eric et al., Selective N-Alkylation of Primary Amines with Chloroacetamides Under pH-Controlled Aqueous Conditions, Synthetic Communications, 32(3) (2002) pp. 403-409.

Majim R. Berichet der Deutschen Chemischen Gesellschaft 1908 41 pp. 176-186.

Mall et al. Reactivity Difference of Cis-Trans Pairs: I Behavior of Stillbene Oxides and Activates Stibene Imines, 1987, Journal of Organic Chemistry, 1987, vol. 52, pp. 4812-4814.

Mannucci, Eduardo, et al., Effect of Metaformin on Glucagon-Like Peptide-1 (GLP-1) and Leptin Levels in Obese Nondiabetic Subjects, Diabetes Care, vol. 24, No. 3 (2001) 489-494.

Marcus et al. PubMed Abstract (Intervirology, 45/4-6):260-6) 2002.

Mentlein, Rolf et al., Dipeptidyl-Peptidase IV Hydrolyses gastric Inhibitory Polypeptide, Glucagon-Like Peptide-1(7-36)amide, Peptide Histidine Methionine and is Respoinsible for Their Degradation in Human Serum, Eur. J. Biochem, vol. 214, 829-835 (1993).

Meyerovitch, Josph et al. "Oral Administration of Vanadate Normalizes Blood Glucose Levels in Streptozotocin-treated Rats" Journal of Biological Chemistry, 1987, vol. 262, No. 14, pp. 6658-6662.

Misra, V. et al. "Synthesis of N-aryl-n . . . " Pol. J. Pharmacol Pharm vol. 31, 1979, pp. 161-167, XP008084507.

Molina, P. et al.: "Iminophosphorane-mediated annulation of 1,3,5-triazine to benzimidazole: Synthesis of 1,3,5-triazino[1,2-a]benzimidazoles" Synthesis 1992 Germany, No. 3, 1992—pp. 297-302, XP002390907.

Mukherjee et al "A novel hypoglycemic compound" Biochemical Pharmacology, vol. 22, 1972, pp. 1529-1531.

Mukerjee, S.S. et al., Chronic Toxicity Studies of a Hypoglycemic Compound: Centpiperalone in Rats & Rhesus Monkeys, Indian Journal of Experimental Biology, vol. 17 (1979) pp. 1346-1349.

Mukerjee, S.S. et al., Tissue Distribution of [3H]Centpiperalone after Oral Administration, Indian J. Biochem. Biophys., vol. 17 (1980) pp. 399-401.

Mukherjee, Surath K. et al., Effect of 2-piperazino-4(3H)-quinazolinone monoacetate on some aspects of carbohydrate metabolism of albino rats, Biochemical Pharmacology, vol. 22 (1973) pp. 2205-2206.

Mukerjee, S.S. et al., Effect of 2-piperazino-4(3H)-quinazolinone monoacetate on the tissue respiration, glucose uptake and lactic acid production by rat hemidiaphragm, Biochemical Pharmacology, vol. 23 (1974) 3066-3067.

Mukherjee, Surath K. et al., Influence of Timing Oral Dosing of a Novel Hypoglycaemic Agent A-4166 in Relation to Food, Diabetologia vol. 38 A194 Supplement 1 (1995).

Mukerjee, S.S. et al., Studies on the Mechanism of Centpiperalone-Induced Hypoglycemia, Acta Diabet. Lat 13, 8 (1976) p. 8.

Mukherjee, Surath K. et al., Studies on the Metabolic Changes Induced by a Synthetic Insulinogenic Agent, Ind. J. Physiol. & Allied Sci., vol. 30, No. 3 (1976) pp. 105-116.

Murthy, G. Rama et al., New Hypoglycemic Agents: Synthesis and Hypogylcemic Activity of Some New 1-[{p-(4-OXO-2-Substituted-3(4H)-Quinazolinyl)-Phenyl} Sulphonyl]-3-Aryl/Cyclohexyl-2-Thioureas, Current Science, vol. 56, No. 24 (1987) pp. 1263-1265.

Murthy, G. Rama et al., New Hypoglycemic Agents: Part V—Synthesis & Hypoglycemic Activity of Some New 1-[[p-(4-OXO-2-Methyl/Phenyl-3 (4H)-Quinazolinyl) Phenyl]] 3-Aryl-2-Ureas, Indian Drugs, 25 (1) (1987) pp. 19-22.

Nakamura, Seiji, et al., Effect of Chronic Vanadate Administration in Partially Depancreatized Rats, Diabetes Research and Clinical Practice 27 (1995) pp. 51-59. (Abstract Only).

Ohkubo, I., et al., Dipeptidyl Peptidase IV From Porcine Seminal Plasma: Purification, Characterization, and N-Terminal Amino Acid Sequence, J. Biochem. (Tokyo) (1994) 116(5) pp. 1182-11826.

Oord, J.J.Van Den "Expression of CD26/dipeptidyl-peptidase IV in benign and malignant pigment-cell lesions of the skin" British Journal of Dermatology, 1998, vol. 138, pp. 615-621.

Pandeya, S.N. et al., Synthesis of Some New Amidine Derivatives As Potent Hypoglycemic Agents, Pharmacological Research Communications, vol. 17, No. 8 (1985) pp. 699-709.

Patent Asbstracts of Japan Publication No. 2002338551, Publication Date Nov. 27, 2002.

Patent Abstracts of Japan, vol. 2003, No. 12, Xanthine Derivative, Dec. 5, 2003 & JP 2003 300977 A (Sumitomo Pharmaceut Co Ltd), Oct. 21, 2003, Abstract.

Pauly, et al. "Inhibition of DPPIV in Rat . . . " RegulatoryPeptides, vol. 64, Issues 1-3, 1996, p. 148.

Pederson, et al. "Improved Glucose Tolerance in Zucker Fatty Rats by Oral Administration of the Dipeptidyl Peptidase IV Inhibitor Isoleucine Thiazolidide" Diabetes, vol. 47, 1998, pp. 1253-1258.

Pillai, Sreekumar et al. "Effects of ATP, Vanadate and Molybdate on Cathepsin D-catalyzed Proteolysis" J of_Bio Chem, No. 14, pp. 8384-8389.

Podanyi, B. et al. "Nitrogen Bridge Compounds . . . " Journal Organic Chemistry, 1986, vol. 51, pp. 394-399.

Poje "Diabetogenic_action_of_alloxan-like . . . " Experientia—vol. 36—1980—pp. 78-79.

Poje et al. "Oxidation of Uric Acid. 4, Synthesis, Structure, and Diabetogenic Action of 5-Imino-2,4,6(1H,3H,5H_-pyrimidinetrione Salts and Their Alloxan-Like Covalent Adducts" J. of Med. Chem. 1988, vol. 28, pp. 861-861.

Polacek et al. "Hypoglycemic Activity of Amine Derivatives" Preliminary Observations Chemische Fabrik von Heyden GmbH. Rogensburg. Azneim-Forsh / Drug Res. 28(I), Heft 5 (1978), pp. 791-793.

Ram, Vishnu Ji et al., Synthesis and Antihyperglycemic Activity of Suitably Functionalized 3H-quinazolin-4-ones, Bioorganic & Medicinal Chemistry 11 (2003), pp. 2439-2444.

Rauchman, B.S. et al. "2,4-Diamino-5-benylpyrimidines and Analogues as antibacterial Agents", Journal of Med. Chem., vol. 23, 1980, pp. 384-391, XP002335048 Scheme II.

Sammour et al. Egyptian Journal of Chemistry (1979) Volume Date 1976, 19(6), 1109-16. (Abstract 2 pages).

Sawyer, James H. et al., Pyrido[1,2-a]pyrimidinium Salts. Part 1. Synthesis from 2-Aminopyridines and Interconversion with 2-(2-Acylvinylamino) pyridines, J.C.S. Perkin I (1972), 1138-1143.

Saxena, A.M. et al., Mode of action of three structurally different hypoglycemic agents: A comparative study, Indian Journal of Experimental Biology, vol. 34 (1996), pp. 351-355.

Schilling et al., CAPLUS 2005:1050865 DN 143:347172.

Sedo, Aleksi et al., Dipeptidyl peptidase IV-like molecules: homologous proteins or homologous activities? Biochimica et Biophysica Acta 1550 (2001), pp. 107-116.

Sekiya, T. et al., Pyrimidine derivatives. III (1) Synthesis of hypoglycemic 4-alkoxy-2-piperazino-activity of 6-polymethylenepyrmidines, Eur. J. Med. Chem. (1982), 75-79.

Senten, Kristel et al., Development of Potent and Selective Dipeptidyl Peptidase II Inhibitors, Bioorganic & Medicinal Chemistry Letters 12 (2002) pp. 2825-2828.

Seth, M. et al., Syntheses of 2-Substituted & 2,3-Distributed 4(3H)-Quinazolones, Indian Journal of Chemistry, vol. 14B (1975), 536-540.

Sharma, Arun K., et al. Tandem sigmatropic shifts in [4 + 2] cycloaddition reactions of 1,3-diazabuta-1,3-dienes with butadienylketene: synthesis of pyrimidinone derivatives. J. Chem. Soc., Perkin Trans. 1, 2002, 774-784.

Shimazawa, Rumiko et al. "Novel Small Molecule Nonpeptide Aminopeptidase N Inhibitors with A Cyclic Imide Skeleton" Journal of Enzyme Inhibition, vol. 14, 1999, pp. 259-275.

Shisheva, Assia, et al., Insulinlike Effects of Zinc Ion in Vitro and in Vivo; Preferential Effects on Desensitized Adipocytes and Induction of Normoglycemia in Streptozocin-Induced Rats, Diabetes, vol. 41 (1992), pp. 982-988.

Sinyak, R. S. et al., Synthesis and Biological Properties of Derivatives of 4-Heterylmercaptoquinazoline, Translated from Khimiko-farmatsevticheskii Zhurnal, vol. 20, No. 2, pp. 168-171 (1986), pp. 103-105.

Sokal, Joseph E., Basal Plasma Glucagon Levels of Man, Journal of Clinical Investigation, vol. 46, No. 5 (1967) pp. 778-785.

Soliman et al. Journal of the Chemical Society of Pakistan (1986), 8(2), 97-106. (Abstract 2 pages).

Somasekhara et al. Indian Journal of Pharmacey (1972), 34(5), 121-2.

Srivastava, P.P. et al., Efficacy of Centpiperalone in Combination With Biguanide & Sulfonylurea, Indian Journal of Experimental Biology, vol. 21 (1983), pp. 390-392.

Sun et al. CAPLUS Abstract 128:257413 (1998).

Syadyaryavichyute et al. Database Crossfire Beilstein Institut Zur Foerderung Der Chmischen Wissenschaften. XP002310118. Beilstein Registry No. 7643826 & Khim. Geterotsikl. Soedin., vol. 32, No. 5, 1996, pp. 703-707.

Tam, S. Y-K, et al.: "Nucleosides 112. Synthesis of Some New Pyrazolo-1 5-A-1 3 5-Triazines and Their C Nucleosides" Journal of Organic Chemistry, vol. 44, No. 25, 1979, pp. 4547-4553, XP002390906.

Tanaka, Keiji et al, Vanadate Inhibits the ATP-Dependant Degradation of Proteins in Reticulocytes Without Affecting Ubiquitin Conjugation, The Journal of Biological Chemistry, vol. 259, No. 4 (1983), 2803-2809.

Troschuetz, R. et al. Database CA Online Chemical Abstracts Service, Columbus, OH, US;, The reaction of O-functional benzylmalononitriles with N-bisnucleophiles as well as alcoholates. XP002311761 retrieved from STN Database accession No. 1994:217538 abstract & Archiv Der Pharmazie (Winheim, Germany), 326(11), 865-9 Coden: ARPMAS; ISSN: 0365-6233, 1993.

Van Heeswijk et al., PubMed Abstract (Antivir Ther. 6(4);2001-29) Dec. 2001.

Villhauer, Edwin B. et al., 1-[[(3-Hydroxy-1-adamantyl)amino]acetyl]-2-cyano-(S)-pyrrolidine: A Potent, Selective, and Orally Bioavailable Dipeptidyl Peptidase IV Inhibitor with Antihyperglycemic Properties, J. Med. Chem. 46 (2003), pp. 2774-2789.

Villhauer, Edwin B. et al., DPP-IV Inhibition and Therapeutic Potential, Annual Reports in Chemistry 36 (2001), 191-200.

Vippagunta et al, Advanced Drug Delivery Reviews 48: 3-26, 2001.
Wang, F. et al.: "A novel Synthesis of Aryl[1,2-a]pyrazine Derivatives" Molecules, Molecular Diversity Preservation International, Basel, CH, vol. 9, May 2004, pp. 574-582, XP002390904.
Wang et al. "Studies of Quinazolinones . . ." Biorganic & Med hem.. Letters, Oxford, GB, vol. 12, No. 4, 2002, pp. 571-574, XP009077496 ISSN 0960-894X.
Weber, A.E.: Dipeptidyl Peptidase IV Inhibitors for the Treatment of Diabetes, Journal of Medicinal Chemistry, vol. 47, 2004 pp. 4135-4141, XP002329845.
West, Antony R., Solid State Chemistry and its Applictions, Wile, New York, 1988, pp. 358 & 365.
Wiedeman, Paul E. et al. "Dipeptidyl peptidase IV inhibitors for the treatment of impaired glucose tolerance and type 2 diabetes" Current Opinion in Investigational Drugs, 2003, vol. 4, No. 4, pp. 412-420.
Wolfe et al., CAPLUS Abstract 115: 114452 (1991).
Wolfe et al. Database Crossfire Beilstein Institut Zur Foerderung Der Chmischen Wissenschaften. XP002310119. Beilstein Registry No. 649497 & J. Pharm. Sci. vol. 80, No. 7, 1991, pp. 705-706.
Wolf Manfred E. "Burger's Medicinal Chemistry, 5ed, Part 1" John Wiley and Sons, 1995, pp. 975-977.

Yakubkene et al. Database Crossfire Beilstein Institut Zur Foerderung Der Chmischen Wissenschaften. XP002310117. Beilstein Registry No. 8373244 & Khim. Geterotsikl. Soedin., No. 8, 1998, pp. 1125-1129.
Yasuda, Nobuyuki et al. "Enhanced secretion of glucagon-like peptide 1 by biguande compouns" Biochem and Biophysical Research Communications, vol. 298, 2002, pp. 779-784.
Yuen, V.G. et al. "Acute and chronic oral administration of bis(maltolato)oxovanadium(IV) in Zucker diabetic fatty (ZDF) rats" Diabetes Research and Clinical Practice, vol. 43, 1999, pp. 9-19.
Zander, Mette et al. "Additive glucose-loweing effects of glucagon-like peptide-1 and metformin in type 2 diabetes" Diabetes Care, vol. 24, 2001, pp. 720-725.
Zhang, Anqi et al. "Vanadate Stimulation of Insulin Release in Normal Mouse Islets" Journal of Biological Chemistry, vol. 266, No. 32, 1991, pp. 21649-21656.
Zorbach et al. Database Crossfire Beilstein Institut Zur Foerderung Der Chmischen Wissenschaften. XP002310120. Beilstein Registry No. 638238 & Synthetic Procedures in Nucleic Acid Chemistry, vol. 1, 1968, p. 92.

* cited by examiner

DIPEPTIDYL PEPTIDASE INHIBITORS

FIELD OF THE INVENTION

The invention relates to methods of making compounds that may be used to inhibit dipeptidyl peptidases. The invention further relates to methods of making intermediates useful in the production of dipeptidyl peptidase inhibitors.

DESCRIPTION OF RELATED ART

Dipeptidyl Peptidase IV (IUBMB Enzyme Nomenclature EC.3.4.14.5) is a type II membrane protein that has been referred to in the literature by a wide a variety of names including DPP4, DP4, DAP-IV, FAPβ, adenosine deaminase complexing protein 2, adenosine deaminase binding protein (ADAbp), dipeptidyl aminopeptidase IV; Xaa-Pro-dipeptidyl-aminopeptidase; Gly-Pro naphthylamidase; postproline dipeptidyl alianopeptidase IV; lymphocyte antigen CD26; glycoprotein GP110; dipeptidyl peptidase IV; glycylproline aminopeptidase; glycylproline aminopeptidase; X-prolyl dipeptidyl aminopeptidase; pep X; leukocyte antigen CD26; glycylprolyl dipeptidylaminopeptidase; dipeptidyl-peptide hydrolase; glycylprolyl aminopeptidase; dipeptidyl-aminopeptidase IV; DPP IV/CD26; amino acyl-prolyl dipeptidyl aminopeptidase; T cell triggering molecule Tp103; X-PDAP. Dipeptidyl Peptidase IV is referred to herein as "DPP-IV."

DPP-IV is a non-classical serine aminodipeptidase that removes Xaa-Pro dipeptides from the amino terminus (N-terminus) of polypeptides and proteins. DPP-IV dependent slow release of dipeptides of the type X-Gly or X-Ser has also been reported for some naturally occurring peptides.

DPP-IV is constitutively expressed on epithelial and endothelial cells of a variety of different tissues (intestine, liver, lung, kidney and placenta), and is also found in body fluids. DPP-IV is also expressed on circulating T-lymphocytes and has been shown to be synonymous with the cell-surface antigen, CD-26. DPP-IV has been implicated in a number of disease states, some of which are discussed below.

DPP-IV is responsible for the metabolic cleavage of certain endogenous peptides (GLP-1 (7-36), glucagon) in vivo and has demonstrated proteolytic activity against a variety of other peptides (GHRH, NPY, GLP-2, VIP) in vitro.

GLP-1 (7-36) is a 29 amino-acid peptide derived by post-translational processing of proglucagon in the small intestine. GLP-1 (7-36) has multiple actions in vivo including the stimulation of insulin secretion, inhibition of glucagon secretion, the promotion of satiety, and the slowing of gastric emptying. Based on its physiological profile, the actions of GLP-1 (7-36) are believed to be beneficial in the prevention and treatment of type II diabetes and potentially obesity. For example, exogenous administration of GLP-1 (7-36) (continuous infusion) in diabetic patients has been found to be efficacious in this patient population. Unfortunately, GLP-1 (7-36) is degraded rapidly in vivo and has been shown to have a short half-life in vivo ($t_{1/2}$=1.5 minutes).

Based on a study of genetically bred DPP-IV knock out mice and on in vivo/in vitro studies with selective DPP-IV inhibitors, DPP-IV has been shown to be the primary degrading enzyme of GLP-1 (7-36) in vivo. GLP-1 (7-36) is degraded by DPP-IV efficiently to GLP-1 (9-36), which has been speculated to act as a physiological antagonist to GLP-1 (7-36). Inhibiting DPP-IV in vivo is therefore believed to be useful for potentiating endogenous levels of GLP-1 (7-36) and attenuating the formation of its antagonist GLP-1 (9-36). Thus, DPP-IV inhibitors are believed to be useful agents for the prevention, delay of progression, and/or treatment of conditions mediated by DPP-IV, in particular diabetes and more particularly, type 2 diabetes mellitus, diabetic dislipidemia, conditions of impaired glucose tolerance (IGT), conditions of impaired fasting plasma glucose (IFG), metabolic acidosis, ketosis, appetite regulation and obesity.

DPP-IV expression is increased in T-cells upon mitogenic or antigenic stimulation (Mattem, T., et al., *Scand. J. Immunol.*, 1991, 33, 737). It has been reported that inhibitors of DPP-IV and antibodies to DPP-IV suppress the proliferation of mitogen-stimulated and antigen-stimulated T-cells in a dose-dependant manner (Schon, E., et al., *Biol. Chem.*, 1991, 372, 305). Various other functions of T-lymphocytes such as cytokine production, IL-2 mediated cell proliferation and B-cell helper activity have been shown to be dependent on DPP-IV activity (Schon, E., et al., *Scand. J. Iimmunol.*, 1989, 29, 127). DPP-IV inhibitors, based on boroproline, (Flentke, G. R., et al., *Proc. Nat. Acad. Sci. USA*, 1991, 88, 1556) although unstable, were effective at inhibiting antigen-induced lymphocyte proliferation and IL-2 production in murine CD4+ T-helper cells. Such boronic acid inhibitors have been shown to have an effect in vivo in mice causing suppression of antibody production induced by immune challenge (Kubota, T. et al., *Clin. Exp. Immun.*, 1992, 89, 192). The role of DPP-IV in regulating T lymphocyte activation may also be attributed, in part, to its cell-surface association with the transmembrane phosphatase, CD45. DPP-IV inhibitors or non-active site ligands may possibly disrupt the CD45-DPP-IV association. CD45 is known to be an integral component of the T-cell signaling apparatus. It has been reported that DPP-IV is essential for the penetration and infectivity of HIV-1 and HIV-2 viruses in CD4+ T-cells (Wakselman, M., Nguyen, C., Mazaleyrat, J.-P., Callebaut, C., Krust, B., Hovanessian, A. G., Inhibition of HIV-1 infection of CD 26+ but not CD 26-cells by a potent cyclopeptidic inhibitor of the DPP-IV activity of CD 26. Abstract P.44 of the 24.sup.th European Peptide Symposium 1996). Additionally, DPP-IV has been shown to associate with the enzyme adenosine deaminase (ADA) on the surface of T-cells (Kameoka, J., et al., *Science*, 193, 26 466). ADA deficiency causes severe combined immunodeficiency disease (SCID) in humans. This ADA-CD26 interaction may provide clues to the pathophysiology of SCID. It follows that inhibitors of DPP-IV may be useful immunosuppressants (or cytokine release suppressant drugs) for the treatment of among other things: organ transplant rejection; autoimmune diseases such as inflammatory bowel disease, multiple sclerosis and rheumatoid arthritis; and the treatment of AIDS.

It has been shown that lung endothelial cell DPP-IV is an adhesion molecule for lung-metastatic rat breast and prostate carcinoma cells (Johnson, R. C., et al., *J. Cell. Biol.*, 1993, 121, 1423). DPP-IV is known to bind to fibronectin and some metastatic tumor cells are known to carry large amounts of fibronectin on their surface. Potent DPP-IV inhibitors may be useful as drugs to prevent metastases of, for example, breast and prostate tumors to the lungs.

High levels of DPP-IV expression have also been found in human skin fibroblast cells from patients with psoriasis, rheumatoid arthritis (RA) and lichen planus (Raynaud, F., et al., *J. Cell. Physiol.*, 1992, 151, 378). Therefore, DPP-IV inhibitors may be useful as agents to treat dermatological diseases such as psoriasis and lichen planus.

High DPP-IV activity has been found in tissue homogenates from patients with benign prostate hypertrophy and in prostatosomes. These are prostate derived organelles important for the enhancement of sperm forward motility (Vanhoof, G., et al., *Eur. J. Clin. Chem. Clin. Biochemi.*, 1992, 30, 333). DPP-IV inhibitors may also act to suppress sperm motility and therefore act as a male contraceptive agent. Conversely, DPP-IV inhibitors have been implicated as novel for treatment of infertility, and particularly human female infertility due to Polycystic ovary syndrome (PCOS, Stein-Leventhal syndrome) which is a condition characterized by thickening of the ovarian capsule and formation of multiple follicular cysts. It results in infertility and amenorrhea.

DPP-IV is thought to play a role in the cleavage of various cytokines (stimulating hematopoietic cells), growth factors and neuropeptides.

Stimulated hematopoietic cells are useful for the treatment of disorders that are characterized by a reduced number of hematopoietic cells or their precursors in vivo. Such conditions occur frequently in patients who are immunosuppressed, for example, as a consequence of chemotherapy and/or radiation therapy for cancer. It was discovered that inhibitors of dipeptidyl peptidase type IV are useful for stimulating the growth and differentiation of hematopoietic cells in the absence of exogenously added cytokines or other growth factors or stromal cells. This discovery contradicts the dogma in the field of hematopoietic cell stimulation, which provides that the addition of cytokines or cells that produce cytokines (stromal cells) is an essential element for maintaining and stimulating the growth and differentiation of hematopoietic cells in culture. (See, e.g., PCT Intl. Application No. PCT/US93/017173 published as WO 94/03055).

DPP-IV in human plasma has been shown to cleave N-terminal Tyr-Ala from growth hormone-releasing factor and cause inactivation of this hormone. Therefore, inhibitors of DPP-IV may be useful in the treatment of short stature due to growth hormone deficiency (Dwarfism) and for promoting GH-dependent tissue growth or re-growth.

DPP-IV can also cleave neuropeptides and has been shown to modulate the activity of neuroactive peptides substance P, neuropeptide Y and CLIP (Mentlein, R., Dahms, P., Grandt, D., Kruger, R., Proteolytic processing of neuropeptide Y and peptide YY by dipeptidyl peptidase IV, *Regul. Pept.*, 49, 133, 1993; Wetzel, W., Wagner, T., Vogel, D., Demuth, H.-U., Balschun, D., Effects of the CLIP fragment ACTH 20-24 on the duration of REM sleep episodes, *Neuropeptides*, 31, 41, 1997). Thus DPP-IV inhibitors may also be useful agents for the regulation or normalization of neurological disorders.

Several compounds have been shown to inhibit DPP-IV. Nonetheless, a need still exists for new DPP-IV inhibitors that have advantageous potency, stability, selectivity, toxicity and/or pharmacodynamics properties. In this regard, synthetic methods are provided that can be used to male a novel class of DPP-IV inhibitors.

SUMMARY OF THE INVENTION

The present invention relates to methods of making compounds. One use of the methods is for making compounds that have activity for inhibiting DPP-IV. It is noted that these compounds may also have activity for inhibiting other S9 proteases and thus may be used against these other S9 proteases as well as DPP-IV.

It is noted that unless a particular stereochemistry is specified, recitation of a compound is intended to encompass all possible stereoisomers (e.g., enantiomers or diastereomers depending on the number of chiral centers), independent of whether the compound is present as an individual isomer or a mixture of isomers. Further, unless otherwise specified, recitation of a compound is intended to encompass all possible resonance forms and tautomers. With regard to the claims, the language "compound comprising the formula" is intended to encompass the compound and all pharmaceutically acceptable ionized forms and solvates, all possible stereoisomers, and all possible resonance forms and tautomers unless otherwise specifically specified in the particular claim.

Definitions

Unless otherwise stated, the following terms used in the specification and claims shall have the following meanings for the purposes of this Application.

"Alicyclic" means a moiety comprising a non-aromatic ring structure. Alicyclic moieties may be saturated or partially unsaturated with one, two or more double or triple bonds. Alicyclic moieties may also optionally comprise heteroatoms such as nitrogen, oxygen and sulfur. The nitrogen atoms can be optionally quaternerized or oxidized and the sulfur atoms can be optionally oxidized. Examples of alicyclic moieties include, but are not limited to moieties with $C_{3-8}$ rings such as cyclopropyl, cyclohexane, cyclopentane, cyclopentene, cyclopentadiene, cyclohexane, cyclohexene, cyclohexadiene, cycloheptane, cycloheptene, cycloheptadiene, cyclooctane, cyclooctene, and cyclooctadiene.

"Aliphatic" means a moiety characterized by a straight or branched chain arrangement of constituent carbon atoms and may be saturated or partially unsaturated with one, two or more double or triple bonds.

"Alkenyl" represented by itself means a straight or branched, unsaturated, aliphatic radical having a chain of carbon atoms having at least one double bond between adjacent carbon atoms. $C_X$ alkenyl and $C_{X-Y}$ alkenyl are typically used where X and Y indicate the number of carbon atoms in the chain. For example, $C_{2-6}$ alkenyl includes alkenyls that have a chain of between 2 and 6 carbons.

"Alkoxy" means an oxygen moiety having a further alkyl substituent. The alkoxy groups of the present invention can be optionally substituted.

"Alkyl" represented by itself means a straight or branched, saturated or unsaturated, aliphatic radical having a chain of carbon atoms, optionally with oxygen (See "oxaalkyl") or nitrogen atoms (See "aminoalkyl") between the carbon atoms. Cx alkyl and $C_{X-Y}$ alkyl are typically used where X and Y indicate the number of carbon atoms in the chain. For example, $C_{1-6}$ alkyl includes alkyls that have a chain of between 1 and 6 carbons (e.g., methyl, ethyl, propyl, isopropyl, butyl, sec-butyl, isobutyl, tert-butyl, vinyl, allyl, 1-propenyl, isopropenyl, 1-butenyl, 2-butenyl, 3-butenyl, 2-methylallyl, ethynyl, 1-propynyl, 2-propynyl, and the like). Alkyl represented along with another radical (e.g., as in arylalkyl, heteroarylalkyl) means a straight or branched, saturated or unsaturated aliphatic divalent radical having the number of atoms indicated or when no atoms are indicated means a bond (e.g., $(C_{6-10})$aryl$(C_{1-3})$alkyl includes, benzyl, phenethyl, 1-phenylethyl, 3-phenylpropyl, 2-thienylmethyl, 2-pyridinylmethyl and the like).

"Alkylene", unless indicated otherwise, means a straight or branched, saturated or unsaturated, aliphatic, divalent radical. $C_X$ alkylene and $C_{X-Y}$ alkylene are typically used where X and Y indicate the number of carbon atoms in the chain. For example, $C_{1-6}$ alkylene includes methylene (—$CH_2$—), ethylene (—$CH_2CH_2$—), trimethylene (—$CH_2CH_2CH_2$—), tetramethylene (—$CH_2CH_2CH_2CH_2$—) 2-butenylene (—$CH_2CH$=$CHCH_2$—), 2-methyltetramethylene (—$CH_2CH(CH_3)CH_2CH_2$—), pentamethylene (—$CH_2CH_2CH_2CH_2CH_2$—) and the like).

"Alkylidene" means a straight or branched saturated or unsaturated, aliphatic radical connected to the parent molecule by a double bond. $C_X$ alkylidene and $C_{X-Y}$ alkylidene are typically used where X and Y indicate the number of carbon atoms in the chain. For example, $C_{1-6}$ alkylidene includes methylene (=$CH_2$), ethylidene (=$CHCH_3$), isopropylidene (=C(CH$_3$)$_2$), propylidene (=CHCH$_2$CH$_3$), allylidene (=CH—CH=CH$_2$), and the like).

"Alkynyl" represented by itself means a straight or branched, unsaturated, aliphatic radical having a chain of carbon atoms having at least one triple bond between adjacent carbon atoms. C$_X$ alkynyl and C$_{X-Y}$ alkynyl are typically used where X and Y indicate the number of carbon atoms in the chain. For example, C$_{2-6}$ alkynyl includes alkynyls that have a chain of between 2 and 6 carbons.

"Amino" means a nitrogen moiety having two further substituents where a hydrogen or carbon atom is attached to the nitrogen. For example, representative amino groups include —NH$_2$, —NHCH$_3$, —N(CH$_3$)$_2$, —NHC$_{1-3}$-alkyl, —N(C$_{1-3}$-alkyl)$_2$ and the like. Unless indicated otherwise, the compounds of the invention containing amino moieties may include protected derivatives thereof. Suitable protecting groups for amino moieties include acetyl, tert-butoxycarbonyl, benzyloxycarbonyl, and the like.

"Aminoalkyl" means an alkyl, as defined above, except where one or more substituted or unsubstituted nitrogen atoms (—N—) are positioned between carbon atoms of the alkyl. For example, an (C$_{2-6}$) aminoalkyl refers to a chain comprising between 2 and 6 carbons and one or more nitrogen atoms positioned between the carbon atoms.

"Animal" includes humans, non-human mammals (e.g., dogs, cats, rabbits, cattle, horses, sheep, goats, swine, deer, and the like) and non-mammals (e.g., birds, and the like).

"Aromatic" means a moiety wherein the constituent atoms make up an unsaturated ring system, all atoms in the ring system are sp$^2$ hybridized and the total number of pi electrons is equal to 4n+2. An aromatic ring may be such that the ring atoms are only carbon atoms or may include carbon and non-carbon atoms (see Heteroaryl).

"Aryl" means a monocyclic or polycyclic ring assembly wherein each ring is aromatic or when fused with one or more rings forms an aromatic ring assembly. If one or more ring atoms is not carbon (e.g., N, S), the aryl is a heteroaryl. C$_X$ aryl and C$_{X-Y}$ aryl are typically used where X and Y indicate the number of atoms in the ring. For example, aryl includes phenyl.

"Bicycloalkyl" means a saturated or partially unsaturated fused bicyclic or bridged polycyclic ring assembly.

"Bicycloaryl" means a bicyclic ring assembly wherein the rings are linked by a single bond or fused and at least one of the rings comprising the assembly is aromatic. C$_X$ bicycloaryl and C$_{X-Y}$ bicycloaryl are typically used where X and Y indicate the number of carbon atoms in the bicyclic ring assembly and directly attached to the ring.

"Bridging ring" as used herein refers to a ring that is bonded to another ring to form a compound having a bicyclic structure where two ring atoms that are common to both rings are not directly bound to each other. Non-exclusive examples of common compounds having a bridging ring include borneol, norbornane, 7-oxabicyclo[2.2.1]heptane, and the like. One or both rings of the bicyclic system may also comprise heteroatoms.

"Carbamoyl" means the radical —OC(O)NR$_a$R$_b$ where R$_a$ and R$_b$ are each independently two further substituents where a hydrogen or carbon atom is attached to the nitrogen.

"Carbocycle" means a ring consisting of carbon atoms.

"Carbocyclic ketone derivative" means a carbocyclic derivative wherein the ring contains a —CO— moiety.

"Carbonyl" means the radical —CO—. It is noted that the carbonyl radical may be further substituted with a variety of substituents to form different carbonyl groups including acids, acid halides, aldehydes, amides, esters, and ketones.

"Carboxy" means the radical —CO$_2$—. It is noted that compounds of the invention containing carboxy moieties may include protected derivatives thereof, i.e., where the oxygen is substituted with a protecting group. Suitable protecting groups for carboxy moieties include benzyl, tert-butyl, and the like.

"Cyano" means the radical —CN.

"Cycloalkyl" means a non-aromatic, saturated or partially unsaturated, monocyclic, fused bicyclic or bridged polycyclic ring assembly. C$_X$ cycloalkyl and C$_{X-Y}$ cycloalkyl are typically used where X and Y indicate the number of carbon atoms in the ring assembly. For example, C$_{3-10}$ cycloalkyl includes cyclopropyl, cyclobutyl, cyclopentyl, cyclohexyl, cyclohexenyl, 2,5-cyclohexadienyl, bicyclo[2.2.2]octyl, adamantan-1-yl, decahydronaphthyl, oxocyclohexyl, dioxocyclohexyl, thiocyclohexyl, 2-oxobicyclo[2.2.1]hept-1-yl, and the like.

"Cycloalkylene" means a divalent saturated or partially unsaturated, monocyclic or polycyclic ring assembly. C$_X$ cycloalkylene and C$_{X-Y}$ cycloalkylene are typically used where X and Y indicate the number of carbon atoms in the ring assembly.

"Fused ring" as used herein refers to a ring that is bonded to another ring to form a compound having a bicyclic structure where the ring atoms that are common to both rings are directly bound to each other. Non-exclusive examples of common fused rings include decalin, naphthalene, anthracene, phenanthrene, indole, furan, benzofuran, quinoline, and the like. Compounds having fused ring systems may be saturated, partially saturated, carbocyclics, heterocyclics, aromatics, heteroaromatics, and the like.

"Halo" means fluoro, chloro, bromo or iodo.

"Halo-substituted alkyl", as an isolated group or part of a larger group, means "alkyl" substituted by one or more "halo" atoms, as such terms are defined in this Application. Halo-substituted alkyl includes haloalkyl, dihaloalkyl, trihaloalkyl, perhaloalkyl and the like (e.g. halo-substituted (C$_{1-3}$)alkyl includes chloromethyl, dichloromethyl, difluoromethyl, trifluoromethyl, 2,2,2-trifluoroethyl, perfluoroethyl, 2,2,2-trifluoro-1,1-dichloroethyl, and the like).

"Heteroatom" refers to an atom that is not a carbon atom. Particular examples of heteroatoms include, but are not limited to nitrogen, oxygen, and sulfur.

"Heteroatom moiety" includes a moiety where the atom by which the moiety is attached is not a carbon. Examples of heteroatom moieties include —N=, —NR$_c$—, —N$^+$(O$^-$)=, —O—, —S— or —S(O)$_2$—, wherein R$_c$ is further substituent.

"Heterobicycloalkyl" means bicycloalkyl, as defined in this Application, provided that one or more of the atoms within the ring is a heteroatom. For example hetero(C$_{9-12}$) bicycloalkyl as used in this application includes, but is not limited to, 3-aza-bicyclo[4.1.0]hept-3-yl, 2-aza-bicyclo[3.1.0]hex-2-yl, 3-aza-bicyclo[3.1.0]hex-3-yl, and the like.

"Heterocycloalkylene" means cycloalkylene, as defined in this Application, provided that one or more of the ring member carbon atoms is replaced by a heteroatom.

"Heteroaryl" means a cyclic aromatic group having five or six ring atoms, wherein at least one ring atom is a heteroatom and the remaining ring atoms are carbon. The nitrogen atoms can be optionally quaternerized and the sulfur atoms can be optionally oxidized. Heteroaryl groups of this invention include, but are not limited to, those derived from furan, imidazole, isothiazole, isoxazole, oxadiazole, oxazole, 1,2,3-oxadiazole, pyrazine, pyrazole, pyridazine, pyridine, pyrimidine, pyrroline, thiazole, 1,3,4-thiadiazole, triazole and tetrazole. "Heteroaryl" also includes, but is not limited to, bicyclic or tricyclic rings, wherein the heteroaryl ring is fused to one or two rings independently selected from the group consisting of an aryl ring, a cycloalkyl ring, a cycloalkenyl ring, and another monocyclic heteroaryl or heterocycloalkyl ring. These bicyclic or tricyclic heteroaryls include, but are not limited to, those derived from benzo[b]furan, benzo[b]thiophene, benzimidazole, imidazo[4,5-c]pyridine, quinazoline, thieno[2,3-c]pyridine, thieno[3,2-b]pyridine, thieno[2,3-b]pyridine, indolizine, imidazo[1,2a]pyridine, quinoline, isoquinoline, phthalazine, quinoxaline, naphthyridine, quinolizine, indole, isoindole, indazole, indoline, benzoxazole, benzopyrazole, benzothiazole, imidazo[1,5-a]pyridine, pyrazolo[1,5-a]pyridine, imidazo[1,2-a]pyrimidine, imidazo[1,2-c]pyrimidine, imidazo[1,5-a]pyrimidine, imidazo[1,5-c]pyrimidine, pyrrolo[2,3-b]pyridine, pyrrolo[2,3-c]pyridine, pyrrolo[3,2-c]pyridine, pyrrolo[3,2-b]pyridine, pyrrolo[2,3-d]pyrimidine, pyrrolo[3,2-d]pyrimidine, pyrrolo[2,3-b]pyrazine, pyrazolo[1,5-a]pyridine, pyrrolo[1,2-b]pyridazine, pyrrolo[1,2-c]pyrimidine, pyrrolo[1,2-a]pyrimidine, pyrrolo[1,2-a]pyrazine, triazo[1,5-a]pyridine, pteridine, purine, carbazole, acridine, phenazine, phenothiazene, phenoxazine, 1,2-dihydropyrrolo[3,2,1-hi]indole, indolizine, pyrido[1,2-a]indole and 2(1H)-pyridinone. The bicyclic or tricyclic heteroaryl rings can be attached to the parent molecule through either the heteroaryl group itself or the aryl, cycloalkyl, cycloalkenyl or heterocycloalkyl group to which it is fused. The heteroaryl groups of this invention can be substituted or unsubstituted.

"Heterobicycloaryl" means bicycloaryl, as defined in this Application, provided that one or more of the atoms within the ring is a heteroatom. For example, hetero($C_{4-10}$)bicycloaryl as used in this Application includes, but is not limited to, 2-amino-4-oxo-3,4-dihydropteridin-6-yl, tetrahydroisoquinolinyl, and the like.

"Heterocycloalkyl" means cycloalkyl, as defined in this Application, provided that one or more of the atoms forming the ring is a heteroatom selected, independently from N, O, or S. Non-exclusive examples of heterocycloalkyl include piperidyl, 4-morpholyl, 4-piperazinyl, pyrrolidinyl, perhydropyrrolizinyl, 1,4-diazaperhydroepinyl, 1,3-dioxanyl, 1,4-dioxanyl and the like.

"Hydroxy" means the radical —OH.

"Iminoketone derivative" means a derivative comprising the moiety —C(NR)—, wherein R comprises a hydrogen or carbon atom attached to the nitrogen.

"Isomers" mean any compound having an identical molecular formulae but differing in the nature or sequence of bonding of their atoms or in the arrangement of their atoms in space. Isomers that differ in the arrangement of their atoms in space are termed "stereoisomers." Stereoisomers that are not mirror images of one another are termed "diastereomers" and stereoisomers that are nonsuperimposable mirror images are termed "enantiomers" or sometimes "optical isomers." A carbon atom bonded to four nonidentical substituents is termed a "chiral center." A compound with one chiral center has two enantiomeric forms of opposite chirality. A mixture of the two enantiomeric forms is termed a "racemic mixture." A compound that has more than one chiral center has $2^{n-1}$ enantiomeric pairs, where n is the number of chiral centers. Compounds with more than one chiral center may exist as ether an individual diastereomer or as a mixture of diastereomers, termed a "diastereomeric mixture." When one chiral center is present a stereoisomer may be characterized by the absolute configuration of that chiral center. Absolute configuration refers to the arrangement in space of the substituents attached to the chiral center. Enantiomers are characterized by the absolute configuration of their chiral centers and described by the R- and S-sequencing rules of Cahn, Ingold and Prelog. Conventions for stereochemical nomenclature, methods for the determination of stereochemistry and the separation of stereoisomers are well known in the art (e.g., see "Advanced Organic Chemistry", 4th edition, March, Jerry, John Wiley & Sons, New York, 1992).

"Leaving group" means a moiety that can be displaced by another moiety, such as by nucleophilic attack, during a chemical reaction. Leaving groups are well known in the art and include, for example, halides and $OSO_2R'$ where R' is, for example, alkyl, haloalkyl, or aryl optionally substituted by halo, alkyl, alkoxy, amino, and the like. Non-limiting examples of leaving groups include chloro, bromo, iodo, mesylate, tosylate, and other similar groups.

"Nitro" means the radical —$NO_2$.

"Oxaalkyl" means an alkyl, as defined above, except where one or more oxygen atoms (—O—) are positioned between carbon atoms of the alkyl. For example, an ($C_{2-6}$)oxaalkyl refers to a chain comprising between 2 and 6 carbons and one or more oxygen atoms positioned between the carbon atoms.

"Oxoalkyl" means an alkyl, further substituted with a carbonyl group. The carbonyl group may be an aldehyde, ketone, ester, amide, acid or acid chloride.

"Pharmaceutically acceptable" means that which is useful in preparing a pharmaceutical composition that is generally safe, non-toxic and neither biologically nor otherwise undesirable and includes that which is acceptable for veterinary use as well as human pharmaceutical use.

"Pharmaceutically acceptable salts" means salts of inhibitors of the present invention which are pharmaceutically acceptable, as defined above, and which possess the desired pharmacological activity. Such salts include acid addition salts formed with inorganic acids such as hydrochloric acid, hydrobromic acid, sulfuric acid, nitric acid, phosphoric acid, and the like; or with organic acids such as acetic acid, propionic acid, hexanoic acid, heptanoic acid, cyclopentanepropionic acid, glycolic acid, pyruvic acid, lactic acid, malonic acid, succinic acid, malic acid, maleic acid, fumaric acid, tartatic acid, citric acid, benzoic acid, o-(4-hydroxybenzoyl) benzoic acid, cinnamic acid, mandelic acid, methanesulfonic acid, ethanesulfonic acid, 1,2-ethanedisulfonic acid, 2-hydroxyethanesulfonic acid, benzenesulfonic acid, p-chlorobenzenesulfonic acid, 2-naphthalenesulfonic acid, p-toluenesulfonic acid, camphorsulfonic acid, 4-methylbicyclo [2.2.2]oct-2-ene-1-carboxylic acid, glucoheptonic acid, 4,4'-methylenebis(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid and the like.

Pharmaceutically acceptable salts also include base addition salts which may be formed when acidic protons present are capable of reacting with inorganic or organic bases. Acceptable inorganic bases include sodium hydroxide, sodium carbonate, potassium hydroxide, aluminum hydroxide and calcium hydroxide. Acceptable organic bases include ethanolamine, diethanolamine, triethanolamine, tromethamine, N-methylglucamine and the like.

"Prodrug" means a compound that is convertible in vivo metabolically into an inhibitor according to the present invention. The prodrug itself may or may not also have DPP-IV inhibitory activity. For example, an inhibitor comprising a hydroxy group may be administered as an ester that is converted by hydrolysis in vivo to the hydroxy compound. Suitable esters that may be converted in vivo into hydroxy compounds include acetates, citrates, lactates, tartrates, malonates, oxalates, salicylates, propionates, succinates, fumarates, maleates, methylene-bis-b-hydroxynaphthoates, gentisates, isethionates, di-p-toluoyltartrates, methanesulfonates, ethanesulfonates, benzenesulfonates, p-toluenesulfonates, cyclohexylsulfamates, quinates, esters of amino acids, and the like. Similarly, an inhibitor comprising an amine group may be administered as an amide that is converted by hydrolysis in vivo to the amine compound.

"Protected derivatives" means derivatives of inhibitors in which a reactive site or sites are blocked with protecting groups. Protected derivatives are useful in the preparation of inhibitors or in themselves may be active as inhibitors. A comprehensive list of suitable protecting groups can be found in T. W. Greene, *Protecting Groups in Organic Synthesis,* 3rd edition, John Wiley & Sons, Inc. 1999.

"Reacting" refers to a chemical process or processes in which two or more reactants are allowed to come into contact with each other to effect a chemical change or transformation. "Reacting" is intended to encompass a variety of methods used in the art for directly or indirectly contacting reactants including, but not being limited to, mixing, stirring, sonicating, and the like.

"Substituted or unsubstituted" means that a given moiety may consist of only hydrogen substituents through available valencies (unsubstituted) or may further comprise one or more non-hydrogen substituents through available valencies (substituted) that are not otherwise specified by the name of the given moiety. For example, isopropyl is an example of an ethylene moiety that is substituted by —$CH_3$. In general, a non-hydrogen substituent may be any substituent that may be bound to an atom of the given moiety that is specified to be substituted. Examples of substituents include, but are not limited to, aldehyde, alicyclic, aliphatic, alkyl, alkylene, alkylidene, amide, amino, aminoalkyl, aromatic, aryl, bicycloalkyl, bicycloaryl, carbamoyl, carbocyclyl, carboxyl, carbonyl group, cyano, cycloalkyl, cycloalkylene, ester, halo, heterobicycloalkyl, heterocycloalkylene, heteroaryl, heterobicycloaryl, heterocycloalkyl, oxo, hydroxy, iminoketone, ketone, nitro, oxaalkyl, and oxoalkyl moieties, each of which may optionally also be substituted or unsubstituted.

"Sulfinyl" means the radical —SO—. It is noted that the sulfinyl radical may be further substituted with a variety of substituents to form different sulfinyl groups including sulfinic acids, sulfinamides, sulfinyl esters, and sulfoxides.

"Sulfonyl" means the radical —$SO_2$—. It is noted that the sulfonyl radical may be further substituted with a variety of substituents to form different sulfonyl groups including sulfonic acids, sulfonamides, sulfonate esters, and sulfones.

"Thiocarbonyl" means the radical —CS—. It is noted that the thiocarbonyl radical may be further substituted with a variety of substituents to form different thiocarbonyl groups including thioacids, thioamides, thioesters, and thioketones.

It is noted in regard to all of the definitions provided herein that the definitions should be interpreted as being open ended in the sense that further substituents beyond those specified may be included. Hence, a $C_1$ alkyl indicates that there is one carbon atom but does not indicate what are the substituents on the carbon atom. Hence, a $C_1$ alkyl comprises methyl (i.e., —$CH_3$) as well as —$R_aR_bR_c$ where $R_a$, $R_b$, and $R_c$ may each independently be hydrogen or any other substituent where the atom attached to the carbon is a heteroatom or cyano. Hence, $CF_3$, $CH_2OH$ and $CH_2CN$, for example, are all $C_1$ alkyls.

DETAILED DESCRIPTION OF THE INVENTION

The present invention relates to methods of making compounds. One use of the methods provided herein is for making compounds that inhibit dipeptidyl peptidases IV (referred to herein as DPP-IV). The methods may also be used to make intermediates useful in the production of dipeptidyl peptidase inhibitors.

In one embodiment, the present invention relates to a process comprising reacting a compound of the formula

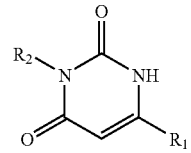

with a compound of the formula

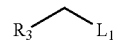

under conditions that form a reaction product of the formula

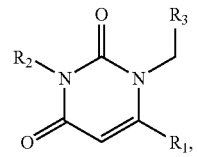

wherein $R_1$ is selected from the group consisting of hydrogen, halo, nitro, cyano, thio, hydroxy, alkoxy, aryloxy, heteroaryloxy, carbonyl, amino, ($C_{1-10}$)alkylamino, sulfonamido, imino, sulfonyl, sulfinyl, ($C_{1-10}$)alkyl, halo($C_{1-10}$)alkyl, carbonyl($C_{1-3}$)alkyl, thiocarbonyl($C_{1-3}$)alkyl, sulfonyl ($C_{1-3}$)alkyl, sulfinyl($C_{1-3}$)alkyl, amino ($C_{1-10}$)alkyl, imino($C_{1-3}$)alkyl, ($C_{3-12}$)cycloalkyl($C_{1-5}$)alkyl, hetero ($C_{3-12}$)cycloalkyl($C_{1-5}$)alkyl, aryl($C_{1-10}$)alkyl, heteroaryl($C_{1-5}$)alkyl, ($C_{9-12}$)bicycloaryl($C_{1-5}$)alkyl, hetero($C_{8-12}$)bicycloaryl($C_{1-5}$)alkyl, ($C_{3-12}$)cycloalkyl, hetero($C_{3-12}$)cycloalkyl, ($C_{9-12}$)bicycloalkyl, hetero ($C_{3-12}$)bicycloalkyl, aryl, heteroaryl, ($C_{9-12}$)bicycloaryl and hetero($C_{4-12}$)bicycloaiyl, each substituted or unsubstituted, $R_2$ is hydrogen or selected from the group consisting of ($C_{1-10}$)alkyl, ($C_{3-12}$)cycloalkyl, ($C_{3-12}$)cycloalkyl($C_{1-5}$) alkyl, hetero($C_{3-12}$)cycloalkyl($C_{1-5}$)alkyl, hetero($C_{3-12}$) cycloalkyl, aryl($C_{1-10}$)alkyl, heteroaryl($C_{1-5}$)alkyl, ($C_{9-12}$)bicycloaryl, hetero($C_{4-12}$)bicycloaryl, hetero($C_{4-12}$)bicycloaryl($C_{1-5}$)alkyl, carbonyl($C_{1-3}$) alkyl, thiocarbonyl($C_{1-3}$)alkyl, sulfonyl($C_{1-3}$)alkyl, sulfinyl($C_{1-3}$)alkyl, imino ($C_{1-3}$)alkyl, amino, aryl, heteroaryl, hydroxy, alkoxy, aryloxy, heteroaryloxy, carbonyl group, imino group, sulfonyl group and sulfinyl group, each substituted or unsubstituted, $R_3$ is selected from the group consisting of ($C_{1-10}$)alkyl, ($C_{3-12}$)cycloalkyl, hetero($C_{3-12}$)cycloalkyl, aryl($C_{1-10}$) alkyl, heteroaryl($C_{1-5}$)alkyl, ($C_{9-12}$)bicycloaryl, hetero ($C_{4-12}$)bicycloaryl, carbonyl($C_{1-3}$)alkyl, thiocarbonyl ($C_{1-3}$)alkyl, sulfonyl ($C_{1-3}$)alkyl, sulfinyl($C_{1-3}$)alkyl, imino ($C_{1-3}$)alkyl, amino, aryl, heteroaryl, hydroxy, alkoxy, aryloxy, heteroaryloxy, alkenyl, alkynyl, carbonyl group, cyano, imino group, sulfonyl group and sulfinyl group, each substituted or unsubstituted, and $L_1$ is a leaving group.

In another embodiment, the present invention relates to a process comprising reacting a compound of the formula

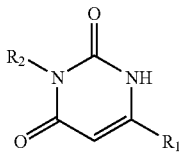

with a compound of the formula

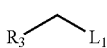

in dimethylsulfoxide in the presence of $K_2CO_3$ under conditions that form a reaction product of the formula

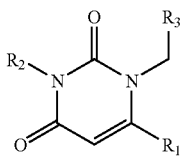

wherein
$R_1$ is selected from the group consisting of hydrogen, halo, nitro, cyano, thio, hydroxy, alkoxy, aryloxy, heteroaryloxy, carbonyl, amino, $(C_{1-10})$alkylamino, sulfonamido, imino, sulfonyl, sulfinyl, $(C_{1-10})$alkyl, halo$(C_{1-10})$alkyl, carbonyl$(C_{1-3})$alkyl, thiocarbonyl$(C_{1-3})$alkyl, sulfonyl $(C_{1-3})$alkyl, sulfinyl$(C_{1-3})$alkyl, amino$(C_{1-10})$alkyl, imino$(C_{1-3})$alkyl, $(C_{3-12})$cycloalkyl$(C_{1-5})$alkyl, hetero$(C_{3-12})$cycloalkyl$(C_{1-5})$alkyl, aryl$(C_{1-10})$alkyl, heteroaryl$(C_{1-5})$alkyl, $(C_{9-12})$bicycloaryl$(C_{1-5})$alkyl, hetero$(C_{8-12})$bicycloaiyl$(C_{1-5})$alkyl, $(C_{3-12})$cycloalkyl, hetero$(C_{3-12})$cycloalkyl, $(C_{9-12})$bicycloalkyl, hetero$(C_{3-12})$bicycloalkyl, aryl, heteroaryl, $(C_{9-12})$bicycloaryl and hetero$(C_{4-12})$bicycloaiyl, each substituted or unsubstituted, $R_2$ is hydrogen or selected from the group consisting of $(C_{1-10})$alkyl, $(C_{3-12})$cycloalkyl, $(C_{3-12})$cycloalkyl$(C_{1-5})$alkyl, hetero$(C_{3-12})$cycloalkyl$(C_{1-5})$alkyl, hetero$(C_{3-12})$cycloalkyl, aryl$(C_{1-10})$alkyl, heteroaryl$(C_{1-5})$alkyl, $(C_{9-12})$bicycloaryl, hetero$(C_{4-12})$bicycloaryl, hetero$(C_{4-12})$bicycloaryl$(C_{1-5})$alkyl, carbonyl$(C_{1-3})$ alkyl, thiocarbonyl$(C_{1-3})$alkyl, sulfonyl$(C_{1-3})$alkyl, sulfinyl$(C_{1-3})$alkyl, imino$(C_{1-3})$alkyl, amino, aryl, heteroaryl, hydroxy, alkoxy, aryloxy, heteroaryloxy, carbonyl group, imino group, sulfonyl group and sulfinyl group, each substituted or unsubstituted, $R_3$ is selected from the group consisting of $(C_{1-10})$alkyl, $(C_{3-12})$cycloalkyl, hetero$(C_{3-12})$cycloalkyl, aryl$(C_{1-10})$ alkyl, heteroaryl$(C_{1-5})$alkyl, $(C_{9-12})$bicycloaryl, hetero$(C_{4-12})$bicycloaryl, carbonyl$(C_{1-3})$alkyl, thiocarbonyl $(C_{1-3})$alkyl, sulfonyl $(C_{1-3})$alkyl, sulfinyl$(C_{1-3})$alkyl, imino$(C_{1-3})$alkyl, amino, aryl, heteroaryl, hydroxy, alkoxy, aryloxy, heteroaryloxy, alkenyl, alkynyl, carbonyl group, cyano, imino group, sulfonyl group and sulfinyl group, each substituted or unsubstituted, and $L_1$ is a leaving group.

In one variation of each of the above embodiments, the reacting step is performed at a temperature between 45° C. and 75° C. In another variation of each of the above embodiments and variations, the reacting step is performed for at least 1 hr.

In yet another variation, the process also comprises the step of extracting the reaction product using ethyl acetate. In still another variation, the process further comprises the step of purifying the reaction product. In one particular variation, the reaction product is purified by column chromatography.

In a further variation of each of the above embodiments and variations, $R_1$ is a leaving group and the reaction product is further reacted with a piperidine of the formula

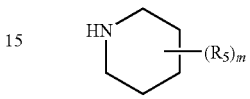

under conditions that form a second reaction product of the formula

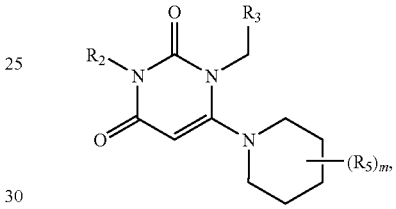

wherein
m is selected from the group consisting of 0, 1, 2, 3, 4, 5, 6, 7, 8, 9 and 10, and each $R_5$ is independently selected from the group consisting of hydrogen, halo, nitro, cyano, thio, hydroxy, alkoxy, aryloxy, heteroaryloxy, carbonyl, amino, $(C_{1-10})$ alkylamino, sulfonamido, imino, sulfonyl, sulfinyl, $(C_{1-10})$alkyl, halo$(C_{1-10})$alkyl, carbonyl$(C_{1-3})$alkyl, thiocarbonyl$(C_{1-3})$alkyl, sulfonyl$(C_{1-3})$alkyl, sulfinyl $(C_{1-3})$alkyl, amino$(C_{1-10})$alkyl, imino$(C_{1-3})$alkyl, $(C_{3-12})$cycloalkyl$(C_{1-5})$alkyl, hetero$(C_{3-12})$cycloalkyl $(C_{1-5})$alkyl, aryl$(C_{1-10})$alkyl, heteroaryl$(C_{1-5})$alkyl, $(C_{9-12})$bicycloaryl$(C_{1-5})$alkyl, hetero$(C_{8-12})$bicycloaryl $(C_{1-5})$alkyl, $(C_{3-12})$cycloalkyl, hetero$(C_{3-12})$cycloalkyl, $(C_{9-12})$bicycloalkyl, hetero$(C_{3-12})$bicycloalkyl, aryl, heteroaryl, $(C_{9-12})$bicycloaryl and hetero$(C_{4-12})$bicycloaiyl, each substituted or unsubstituted.

In still another embodiment, the present invention relates to a process comprising forming a mixture of sodium hydride and lithium bromide with a compound of the formula

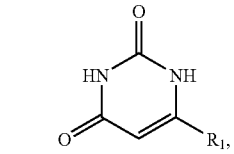

and adding to the mixture a compound of the formula

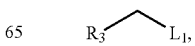

wherein
the process is performed under conditions that form a reaction product of the formula

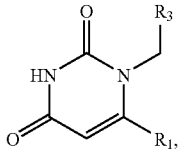

$R_1$ is selected from the group consisting of hydrogen, halo, nitro, cyano, thio, hydroxy, alkoxy, aryloxy, heteroaryloxy, carbonyl, amino, $(C_{1-10})$alkylamino, sulfonamido, imino, sulfonyl, sulfinyl, $(C_{1-10})$alkyl, halo$(C_{1-10})$alkyl, carbonyl$(C_{1-3})$alkyl, thiocarbonyl$(C_{1-3})$alkyl, sulfonyl $(C_{1-3})$alkyl, sulfinyl$(C_{1-3})$alkyl, amino$(C_{1-10})$alkyl, imino$(C_{1-3})$alkyl, $(C_{3-12})$cycloalkyl$(C_{1-5})$alkyl, hetero$(C_{3-12})$cycloalkyl$(C_{1-5})$alkyl, aryl$(C_{1-10})$alkyl, heteroaiyl$(C_{1-5})$alkyl, $(C_{9-12})$bicycloaryl$(C_{1-5})$alkyl, hetero$(C_{8-12})$bicycloaryl$(C_{1-5})$alkyl, $(C_{3-12})$cycloalkyl, hetero$(C_{3-12})$cycloalkyl, $(C_{9-12})$bicycloalkyl, hetero$(C_{3-12})$bicycloalkyl, aryl, heteroaryl, $(C_{9-12})$bicycloaryl and hetero$(C_{4-12})$bicycloaryl, each substituted or unsubstituted, $R_3$ is selected from the group consisting of $(C_{1-10})$alkyl, $(C_{3-12})$cycloalkyl, hetero$(C_{3-12})$cycloalkyl, aryl$(C_{1-10})$ alkyl, heteroaryl$(C_{1-5})$alkyl, $(C_{9-12})$bicycloaryl, hetero $(C_{4-12})$bicycloaryl, carbonyl$(C_{1-3})$alkyl, thiocarbonyl $(C_{1-3})$alkyl, sulfonyl $(C_{1-3})$alkyl, sulfinyl$(C_{1-3})$alkyl, imino$(C_{1-3})$alkyl, amino, aryl, heteroaryl, hydroxy, alkoxy, aryloxy, heteroaryloxy, alkenyl, alkynyl, carbonyl group, cyano, imino group, sulfonyl group and sulfinyl group, each substituted or unsubstituted, and $L_1$ is a leaving group.

In one variation, at least a portion of the process is conducted at a temperature between $-5°$ C. and $5°$ C. In another variation, the reaction product is further reacted with a compound of the formula $R_2'$-X to form a second reaction product of the formula

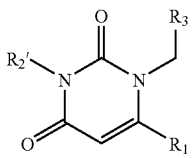

wherein
$R_2'$ is a substituted or unsubstituted $(C_{1-10})$alkyl, and
X is a halide.

In still another variation, $R_1$ is a leaving group and the second reaction product is further reacted with a piperidine of the formula

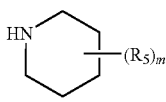

under conditions that form a compound of the formula

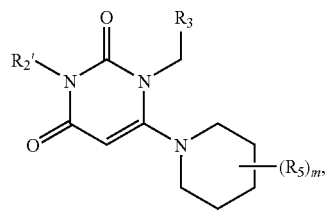

wherein
m is selected from the group consisting of 0, 1, 2, 3, 4, 5, 6, 7, 8, 9 and 10; and
each $R_5$ is independently selected from the group consisting of hydrogen, halo, nitro, cyano, thio, hydroxy, alkoxy, aryloxy, heteroaryloxy, carbonyl, amino, $(C_{1-10})$ alkylamino, sulfonamido, imino, sulfonyl, sulfinyl, $(C_{1-10})$alkyl, halo$(C_{1-10})$alkyl, carbonyl$(C_{1-3})$alkyl, thiocarbonyl$(C_{1-3})$alkyl, sulfonyl$(C_{1-3})$alkyl, sulfinyl $(C_{1-3})$alkyl, amino$(C_{1-10})$alkyl, imino$(C_{1-3})$alkyl, $(C_{3-12})$cycloalkyl$(C_{1-5})$alkyl, hetero$(C_{3-12})$cycloalkyl $(C_{1-5})$alkyl, aryl$(C_{1-10})$alkyl, heteroaryl$(C_{1-5})$alkyl, $(C_{9-12})$bicycloaryl$(C_{1-5})$alkyl, hetero$(C_{8-12})$bicycloaryl $(C_{1-5})$alkyl, $(C_{3-12})$cycloalkyl, hetero$(C_{3-12})$cycloalkyl, $(C_{9-12})$bicycloalkyl, hetero$(C_{3-12})$bicycloalkyl, aryl, heteroaryl, $(C_{9-12})$bicycloaryl and hetero$(C_{4-12})$bicycloaryl, each substituted or unsubstituted.

In a further embodiment, the present invention relates to a process comprising reacting a compound of the formula

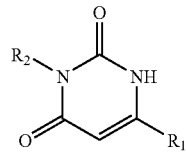

with a compound of the formula

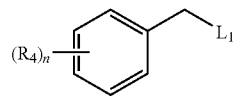

under conditions that form a reaction product of the formula

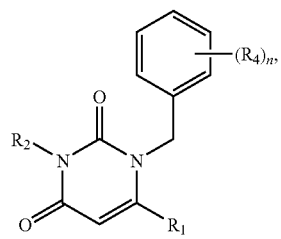

wherein
n is selected from the group consisting of 0, 1, 2, 3, 4 and 5;
$R_1$ is selected from the group consisting of hydrogen, halo, nitro, cyano, thio, hydroxy, alkoxy, aryloxy, heteroaryloxy, carbonyl, amino, $(C_{1-10})$alkylamino, sulfonamido, imino, sulfonyl, sulfinyl, $(C_{1-10})$alkyl, halo$(C_{1-10})$alkyl, carbonyl$(C_{1-3})$alkyl, thiocarbonyl$(C_{1-3})$alkyl, sulfonyl ($C_{1-3}$)alkyl, sulfinyl($C_{1-3}$)alkyl, amino($C_{1-10}$)alkyl, imino($C_{1-3}$)alkyl, ($C_{3-12}$)cycloalkyl($C_{1-5}$)alkyl, hetero($C_{3-12}$)cycloalkyl($C_{1-5}$)alkyl, aryl($C_{1-10}$)alkyl, heteroaryl($C_{1-5}$)alkyl, ($C_{9-12}$)bicycloaryl($C_{1-5}$)alkyl, hetero($C_{9-12}$)bicycloaryl($C_{1-5}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, aryl, heteroaryl, ($C_{9-12}$)bicycloaryl and hetero($C_{4-12}$)bicycloaryl, each substituted or unsubstituted;

$R_2$ is hydrogen or selected from the group consisting of ($C_{1-10}$)alkyl, ($C_{3-12}$)cycloalkyl, ($C_{3-12}$)cycloalkyl($C_{1-5}$)alkyl, hetero($C_{3-12}$)cycloalkyl($C_{1-5}$)alkyl, hetero($C_{3-12}$)cycloalkyl, aryl($C_{1-10}$)alkyl, heteroaryl($C_{1-5}$)alkyl, ($C_{9-12}$)bicycloaryl, hetero($C_{4-12}$)bicycloaryl, hetero($C_{4-12}$)bicycloaryl($C_{1-5}$)alkyl, carbonyl($C_{1-3}$)alkyl, thiocarbonyl($C_{1-3}$)alkyl, sulfonyl($C_{1-3}$)alkyl, sulfinyl($C_{1-3}$)alkyl, imino($C_{1-3}$)alkyl, amino, aryl, heteroaryl, hydroxy, alkoxy, aryloxy, heteroaryloxy, carbonyl group, imino group, sulfonyl group and sulfinyl group, each substituted or unsubstituted;

each $R_4$ is independently selected from the group consisting of hydrogen, halo, nitro, cyano, thio, hydroxy, alkoxy, aryloxy, heteroaryloxy, carbonyl, amino, ($C_{1-10}$) alkylamino, sulfonamido, imino, sulfonyl, sulfinyl, ($C_{1-10}$)alkyl, halo($C_{1-10}$)alkyl, carbonyl($C_{1-3}$)alkyl, thiocarbonyl($C_{1-3}$)alkyl, sulfonyl($C_{1-3}$)alkyl, sulfinyl($C_{1-3}$)alkyl, amino($C_{1-10}$)alkyl, imino($C_{1-3}$)alkyl, ($C_{3-12}$)cycloalkyl($C_{1-5}$)alkyl, hetero($C_{3-12}$)cycloalkyl($C_{1-5}$)alkyl, aryl($C_{1-10}$)alkyl, heteroaryl($C_{1-5}$)alkyl, ($C_{9-12}$)bicycloaryl($C_{1-5}$)alkyl, hetero($C_8S_{12}$)bicycloaryl($C_{1-5}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, aryl, heteroaryl, ($C_{9-12}$)bicycloaryl and hetero($C_{4-12}$)bicycloaryl, each substituted or unsubstituted; and $L_1$ is a leaving group.

In one variation, $R_1$ is a leaving group and the reaction product is further reacted with a piperidine of the formula

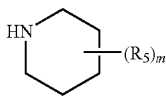

under conditions that form a second reaction product of the formula

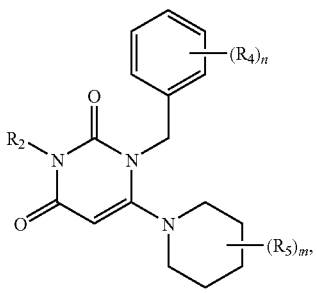

wherein m is selected from the group consisting of 0, 1, 2, 3, 4, 5, 6, 7, 8, 9 and 10, and each $R_5$ is independently selected from the group consisting of hydrogen, halo, nitro, cyano, thio, hydroxy, alkoxy, aryloxy, heteroaryloxy, carbonyl, amino, ($C_{1-10}$) alkylamino, sulfonamido, imino, sulfonyl, sulfinyl, ($C_{1-10}$)alkyl, halo($C_{1-10}$)alkyl, carbonyl($C_{1-3}$)alkyl, thiocarbonyl($C_{1-3}$)alkyl, sulfonyl($C_{1-3}$)alkyl, sulfinyl($C_{1-3}$)alkyl, amino($C_{1-10}$)alkyl, imino($C_{1-3}$)alkyl, ($C_{3-12}$)cycloalkyl($C_{1-5}$)alkyl, hetero($C_{3-12}$)cycloalkyl($C_{1-5}$)alkyl, aryl($C_{1-10}$)alkyl, heteroaryl($C_{1-5}$)alkyl, ($C_{9-12}$)bicycloaryl($C_{1-5}$)alkyl, hetero($C_{8-12}$)bicycloaryl($C_{1-5}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, aryl, heteroaryl, ($C_{9-12}$)bicycloaryl and hetero($C_{4-12}$)bicycloaryl, each substituted or unsubstituted.

In another embodiment, the present invention relates to a process comprising reacting a compound of the formula

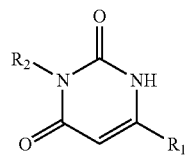

with a compound of the formula

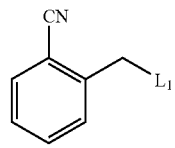

under conditions that form a reaction product of the formula

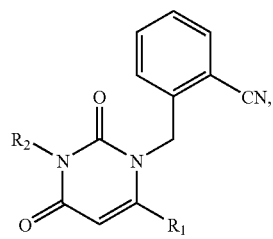

wherein $R_1$ is selected from the group consisting of hydrogen, halo, nitro, cyano, thio, hydroxy, alkoxy, aryloxy, heteroaryloxy, carbonyl, amino, ($C_{1-10}$)alkylamino, sulfonamido, imino, sulfonyl, sulfinyl, ($C_{1-10}$)alkyl, halo($C_{1-10}$)alkyl, carbonyl($C_{1-3}$)alkyl, thiocarbonyl($C_{1-3}$)alkyl, sulfonyl($C_{1-3}$)alkyl, sulfinyl($C_{1-3}$)alkyl, amino($C_{1-10}$)alkyl, imino($C_{1-3}$)alkyl, ($C_{3-12}$)cycloalkyl($C_{1-5}$)alkyl, hetero($C_{3-12}$)cycloalkyl($C_{1-5}$)alkyl, aryl($C_{1-10}$)alkyl, heteroaryl($C_{1-5}$)alkyl, ($C_{9-12}$)bicycloaryl($C_{1-5}$)alkyl, hetero($C_{9-12}$)bicycloaryl($C_{1-5}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, aryl, heteroaryl, ($C_{9-12}$)bicycloaryl and hetero($C_{4-12}$)bicycloaryl, each substituted or unsubstituted, $R_2$ is hydrogen or selected from the group consisting of ($C_{1-10}$)alkyl, ($C_{3-12}$)cycloalkyl, ($C_{3-12}$)cycloalkyl($C_{1-5}$)alkyl, hetero($C_{3-12}$)cycloalkyl($C_{1-5}$)alkyl, hetero($C_{3-12}$)cycloalkyl, aryl($C_{1-10}$)alkyl, heteroaryl($C_{1-5}$)alkyl, ($C_{9-12}$)bicycloaryl, hetero($C_{4-12}$)bicycloaryl, hetero($C_{4-12}$)bicycloaryl($C_{1-5}$)alkyl, carbonyl($C_{1-3}$)

alkyl, thiocarbonyl($C_{1-3}$)alkyl, sulfonyl($C_{1-3}$)alkyl, sulfinyl($C_{1-3}$)alkyl, imino($C_{1-3}$)alkyl, amino, aryl, heteroaryl, hydroxy, alkoxy, aryloxy, heteroaryloxy, carbonyl group, imino group, sulfonyl group and sulfinyl group, each substituted or unsubstituted, and $L_1$ is a leaving group.

In one variation, $R_1$ is a leaving group and the reaction product is further reacted with a piperidine of the formula

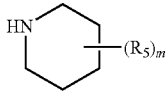

under conditions that form a second reaction product of the formula

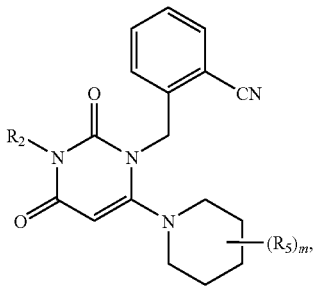

wherein m is selected from the group consisting of 0, 1, 2, 3, 4, 5, 6, 7, 8, 9 and 10; and each $R_5$ is independently selected from the group consisting of hydrogen, halo, nitro, cyano, thio, hydroxy, alkoxy, aryloxy, heteroaryloxy, carbonyl, amino, ($C_{1-10}$)alkylamino, sulfonamido, imino, sulfonyl, sulfinyl, ($C_{1-10}$)alkyl, halo($C_{1-10}$)alkyl, carbonyl($C_{1-3}$)alkyl, thiocarbonyl($C_{1-3}$)alkyl, sulfonyl($C_{1-3}$)alkyl, sulfinyl($C_{1-3}$)alkyl, amino($C_{1-10}$)alkyl, imino($C_{1-3}$)alkyl, ($C_{3-12}$)cycloalkyl($C_{1-5}$)alkyl, hetero($C_{3-12}$)cycloalkyl($C_{1-5}$)alkyl, aryl($C_{1-10}$)alkyl, heteroaryl($C_{1-5}$)alkyl, ($C_{9-12}$)bicycloaryl($C_{1-5}$)alkyl, hetero($C_{9-12}$)bicycloaryl($C_{1-5}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, aryl, heteroaryl, ($C_{9-12}$)bicycloaryl and hetero($C_{4-12}$)bicycloaryl, each substituted or unsubstituted.

In still another embodiment, the present invention relates to a process comprising reacting a compound of the formula

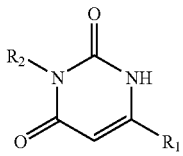

with a compound of the formula

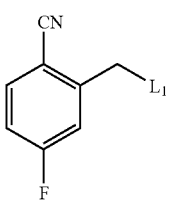

under conditions that form a reaction product of the formula

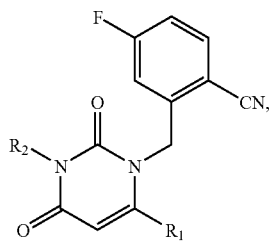

wherein $R_1$ is selected from the group consisting of hydrogen, halo, nitro, cyano, thio, hydroxy, alkoxy, aryloxy, heteroaryloxy, carbonyl, amino, ($C_{1-10}$)alkylamino, sulfonamido, imino, sulfonyl, sulfinyl, ($C_{1-10}$)alkyl, halo($C_{1-10}$)alkyl, carbonyl($C_{1-3}$)alkyl, thiocarbonyl($C_{1-3}$)alkyl, sulfonyl($C_{1-3}$)alkyl, sulfinyl($C_{1-3}$)alkyl, amino($C_{1-10}$)alkyl, imino($C_{1-3}$)alkyl, ($C_{3-12}$)cycloalkyl($C_{1-5}$)alkyl, hetero($C_{3-12}$)cycloalkyl($C_{1-5}$)alkyl, aryl($C_{1-10}$)alkyl, heteroaryl($C_{1-5}$)alkyl, ($C_{9-12}$)bicycloaryl($C_{1-5}$)alkyl, hetero($C_{8-12}$)bicycloaryl($C_{1-5}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, aryl, heteroaryl, ($C_{9-12}$)bicycloaryl and hetero($C_{4-12}$)bicycloaryl, each substituted or unsubstituted, $R_2$ is hydrogen or selected from the group consisting of ($C_{1-10}$)alkyl, ($C_{3-12}$)cycloalkyl, ($C_{3-12}$)cycloalkyl($C_{1-5}$)alkyl, hetero($C_{3-12}$)cycloalkyl($C_{1-5}$)alkyl, hetero($C_{3-12}$)cycloalkyl, aryl($C_{1-10}$)alkyl, heteroaryl($C_{1-5}$)alkyl, ($C_{9-12}$)bicycloaryl, hetero($C_{4-12}$)bicycloaryl, hetero($C_{4-12}$)bicycloaryl($C_{1-5}$)alkyl, carbonyl($C_{1-3}$)alkyl, thiocarbonyl($C_{1-3}$)alkyl, sulfonyl($C_{1-3}$)alkyl, sulfinyl($C_{1-3}$)alkyl, imino($C_{1-3}$)alkyl, amino, aryl, heteroaryl, hydroxy, alkoxy, aryloxy, heteroaryloxy, carbonyl group, imino group, sulfonyl group and sulfinyl group, each substituted or unsubstituted, and $L_1$ is a leaving group.

In one variation, $R_1$ is a leaving group and the reaction product is further reacted with a piperidine of the formula

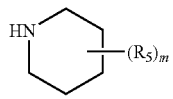

under conditions that form a second reaction product of the formula

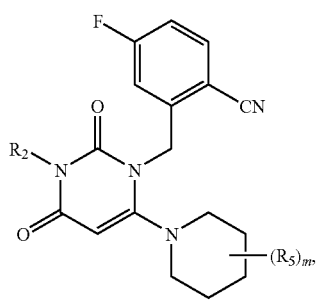

wherein m is selected from the group consisting of 0, 1, 2, 3, 4, 5, 6, 7, 8, 9 and 10, and each $R_5$ is independently selected from the group consisting of hydrogen, halo, nitro, cyano, thio, hydroxy, alkoxy, aryloxy, heteroaryloxy, carbonyl, amino, $(C_{1-10})$alkylamino, sulfonamido, imino, sulfonyl, sulfinyl, $(C_{1-10})$alkyl, halo$(C_{1-10})$alkyl, carbonyl$(C_{1-3})$alkyl, thiocarbonyl$(C_{1-3})$alkyl, sulfonyl$(C_{1-3})$alkyl, sulfinyl $(C_{1-3})$alkyl, amino$(C_{1-10})$alkyl, imino$(C_{1-3})$alkyl, $(C_{3-12})$cycloalkyl$(C_{1-5})$alkyl, hetero$(C_{3-12})$cycloalkyl $(C_{1-5})$alkyl, aryl$(C_{1-10})$alkyl, heteroaryl$(C_{1-5})$alkyl, $(C_{9-12})$bicycloaryl$(C_{1-5})$alkyl, hetero$(C_{8-12})$bicycloaryl $(C_{1-5})$alkyl, $(C_{3-12})$cycloalkyl, hetero$(C_{3-12})$cycloalkyl, $(C_{9-12})$bicycloalkyl, hetero$(C_{3-12})$bicycloalkyl, aryl, heteroaryl, $(C_{9-12})$bicycloaryl and hetero$(C_{4-12})$bicycloaryl, each substituted or unsubstituted.

In one variation of each of the above embodiments and variations, $R_1$ is a leaving group. In one particular variation, $R_1$ is selected from the group consisting of halo (e.g., chloro, bromo and iodo), and $OSO_2R'$ where R' is alkyl, haloalkyl, or aryl optionally substituted by halo, alkyl, alkoxy or amino (e.g., mesylate and tosylate). In another particular variation, $R_1$ is halo. In still another particular variation, $R_1$ is chloro.

In another variation of each of the above embodiments and variations, $R_2$ is hydrogen. In still another variation, $R_2$ is a substituted or unsubstituted $C_{1-6}$ alkyl. In one particular variation, $R_2$ is methyl.

In yet another variation of each of the above embodiments and variations, $R_2'$ is hydrogen. In a further variation, $R_2'$ is a substituted or unsubstituted $C_{1-6}$ alkyl. In one particular variation, $R_2'$ is methyl.

In a further variation of each of the above embodiments and variations, $R_3$ is a substituted or unsubstituted aryl or heteroaryl. In another variation, $R_3$ is a substituted or unsubstituted phenyl. In still another variation, $R_3$ is a phenyl substituted with one or more substituents selected from the group consisting of halo, perhalo$(C_{1-10})$alkyl, $CF_3$, $(C_{1-10})$alkyl, alkenyl, alkynyl, aryl, heteroaryl, aminosulfonyl, alkylsulfonyl, arylsulfonyl, heteroarylsulfonyl, aryloxy, heteroaryloxy, arylalkyl, heteroarylalkyl, cycloalkyl, heterocycloalkyl, amino, thio, cyano, nitro, hydroxy, alkoxy, carbonyl group, imino group, sulfonyl group and sulfinyl group, each substituted or unsubstituted. In one particular variation, $R_3$ is a cyanophenyl and optionally a 2-cyanophenyl. In another particular variation, $R_3$ is a halocyanophenyl and optionally 2-cyano-5-fluorophenyl.

In another variation of each of the above embodiments and variations, each $R_4$ is independently cyano or halo.

In still another variation of each of the above embodiments and variations, at least one $R_5$ is amino.

In another embodiment, the present invention relates to a process comprising reacting a compound of the formula

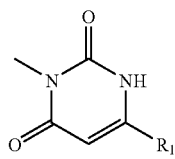

with a compound of the formula

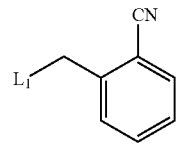

under conditions that form a reaction product of the formula

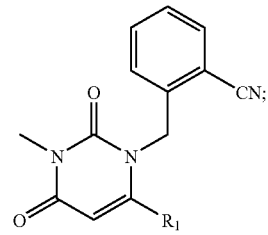

and reacting the reaction product with a piperidine of the formula

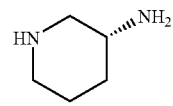

under conditions that form a second reaction product of the formula:

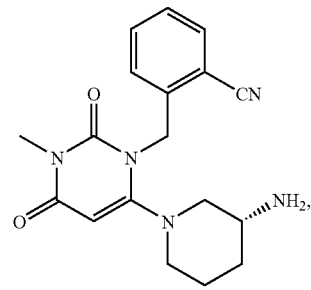

wherein $R_1$ is halo, and $L_1$ is a leaving group.

In still another embodiment, the present invention relates to a process comprising reacting a compound of the formula

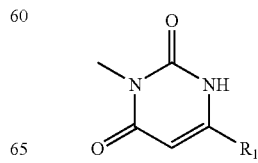

with a compound of the formula

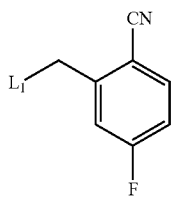

under conditions that form a reaction product of the formula

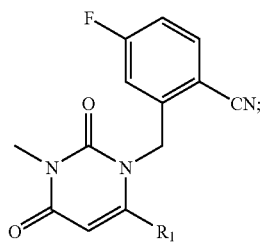

and reacting the reaction product with a piperidine of the formula

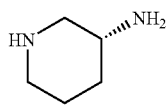

under conditions that form a second reaction product of the formula

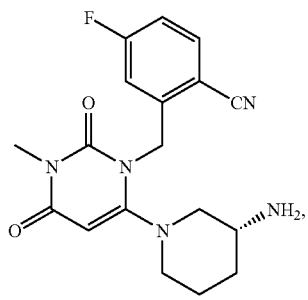

wherein
$R_1$ is halo, and
$L_1$ is a leaving group.

In one variation of each of the above embodiments and variations, $L_1$ is halo and optionally bromo.

In one variation the pyrimidindione product is further converted to an acid addition salt. In particular variations, the acid addition salt is selected from the group consisting of acetate, citrate, hydrochloride, L-lactate, succinate, sulfate, p-toluenesulfonate, benzenesulfonate, benzoate, methanesulfonate, naphthylene-2-sulfonate, propionate, p-toluenesulfonate, hydrobromate, hydroiodate, R-mandelate, and L-tartrate.

In still another variation of each of the above embodiments and variations, the pyrimidin-dione is present as a mixture of stereoisomers. In yet another variation, the pyrimidin-dione comprises a single stereoisomer.

It is noted in regard to all of the embodiments, and any further embodiments, variations, or individual compounds described or claimed herein that all such embodiments, variations, and/or individual compounds are intended to encompass all pharmaceutical acceptable salt forms whether in the form of a single stereoisomer or mixture of stereoisomers unless it is specifically specified otherwise. Similarly, when one or more potentially chiral centers are present in any of the embodiments, variations, and/or individual compounds specified or claimed herein, both possible chiral centers are intended to be encompassed unless it is specifically specified otherwise.

Salts, Hydrates, and Prodrugs of DPP-IV Inhibitors

It should be recognized that compounds made according to the present invention for pharmaceutical applications may optionally be converted into pharmaceutically acceptable salts and prodrugs.

When compounds made according to the present invention possess a free base form, the compounds can be prepared as a pharmaceutically acceptable acid addition salt by reacting the free base form of the compound with a pharmaceutically acceptable inorganic or organic acid, e.g., hydrohalides such as hydrochloride, hydrobromide, hydroiodide; other mineral acids and their corresponding salts such as sulfate, nitrate, phosphate, etc.; and alkyl and monoarylsulfonates such as ethanesulfonate, toluenesulfonate and benzenesulfonate; and other organic acids and their corresponding salts such as acetate, tartrate, maleate, succinate, citrate, benzoate, salicylate and ascorbate. Further examples of acid addition salts include, but are not limited to: adipate, alginate, arginate, aspartate, bisulfate, bisulfite, bromide, butyrate, camphorate, camphorsulfonate, caprylate, chloride, chlorobenzoate, cyclopentanepropionate, digluconate, dihydrogenphosphate, dinitrobenzoate, dodecylsulfate, fumarate, galacterate (from mucic acid), galacturonate, glucoheptaoate, gluconate, glutamate, glycerophosphate, hemisuccinate, hemisulfate, heptanoate, hexanoate, hippurate, hydrochloride, hydrobromide, hydroiodide, 2-hydroxyethanesulfonate, iodide, isethionate, iso-butyrate, lactate, lactobionate, malate, malonate, mandelate, metaphosphate, methanesulfonate, methylbenzoate, monohydrogenphosphate, 2-naphthalenesulfonate, nicotinate, nitrate, oxalate, oleate, pamoate, pectinate, persulfate, phenylacetate, 3-phenylpropionate, phosphate, phosphonate and phthalate. It should be recognized that the free base forms will typically differ from their respective salt forms somewhat in physical properties such as solubility in polar solvents, but otherwise the salts are equivalent to their respective free base forms.

When the compounds made according to the present invention possess a free acid form, a pharmaceutically acceptable base addition salt can be prepared by reacting the free acid form of the compound with a pharmaceutically acceptable inorganic or organic base. Examples of such bases are alkali metal hydroxides including potassium, sodium and lithium hydroxides; alkaline earth metal hydroxides such as barium and calcium hydroxides; alkali metal alkoxides, e.g. potassium ethanolate and sodium propanolate; and various organic bases such as ammonium hydroxide, piperidine, diethanolamine and N-methylglutamine. Also included are the aluminum salts of the compounds made according to the present invention. Further examples of base salts include, but are not limited to: copper, ferric, ferrous, lithium, magnesium, manganic, manganous, potassium, sodium and zinc salts. Examples of organic base salts include, but are not limited to, salts of primary, secondary and tertiary amines, substituted amines including naturally occurring substituted amines, cyclic amines and basic ion exchange resins, e.g., arginine, betaine, caffeine, chloroprocaine, choline, N,N'-dibenzylethylenediamine(benzathine), dicyclohexylamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, iso-propylamine, lidocaine, lysine, meglumine, N-methyl-D-glucamine, morpholine, piperazine, piperidine, polyamine resins, procaine, purines, theobromine, triethanolamine, triethylamine, trimethylamine, tripropylamine and tris-(hydroxymethyl)-methylamine (tromethamine). It should be recognized that the free acid forms will typically differ from their respective salt forms somewhat in physical properties such as solubility in polar solvents, but otherwise the salts are equivalent to their respective free acid forms.

Compounds that comprise basic nitrogen-containing groups may be quaternized with such agents as $(C_{1-4})$alkyl halides, e.g., methyl, ethyl, iso-propyl and tert-butyl chlorides, bromides and iodides; di$(C_{1-4})$alkyl sulfates, e.g., dimethyl, diethyl and diamyl sulfates; $(C_{10-18})$alkyl halides, e.g., decyl, dodecyl, lauryl, myristyl and stearyl chlorides, bromides and iodides; and aryl$(C_{1-4})$alkyl halides, e.g., benzyl chloride and phenethyl bromide. Such salts permit the preparation of both water-soluble and oil-soluble compounds.

N-oxides of compounds can be prepared by methods known to those of ordinary skill in the art. For example, N-oxides can be prepared by treating an unoxidized form of the compound with an oxidizing agent (e.g., trifluoroperacetic acid, permaleic acid, perbenzoic acid, peracetic acid, meta-chloroperoxybenzoic acid, or the like) in a suitable inert organic solvent (e.g., a halogenated hydrocarbon such as dichloromethane) at approximately 0° C. Alternatively, the N-oxides of the compounds can be prepared from the N-oxide of an appropriate starting material.

Prodrug derivatives of compounds can be prepared by modifying substituents that are then converted in vivo to a different substituent. For example, prodrugs can be prepared by reacting a compound with a carbamylating agent (e.g., 1,1-acyloxyalkylcarbonochloridate, para-nitrophenyl carbonate, or the like) or an acylating agent. Further examples of methods of making prodrugs are described in Saulnier et al. (1994), *Bioorganic and Medicinal Chemistry Letters*, Vol. 4, p. 1985.

Protected derivatives of compounds can also be made. Examples of techniques applicable to the creation of protecting groups and their removal can be found in T. W. Greene, *Protecting Groups in Organic Synthesis*, $3^{rd}$ edition, John Wiley & Sons, Inc. 1999.

Compounds may also be conveniently prepared, or formed, as solvates (e.g. hydrates). Hydrates of compounds may be conveniently prepared by recrystallization from an aqueous/organic solvent mixture, using organic solvents such as dioxin, tetrahydrofuran or methanol.

A "pharmaceutically acceptable salt", as used herein, is intended to encompass any compound made according to the present invention that is utilized in the form of a salt thereof, especially where the salt confers on the compound improved pharmacokinetic properties as compared to the free form of compound or a different salt form of the compound. The pharmaceutically acceptable salt form may also initially confer desirable pharmacokinetic properties on the compound that it did not previously possess, and may even positively affect the pharmacodynamics of the compound with respect to its therapeutic activity in the body. An example of a pharmacokinetic property that may be favorably affected is the manner in which the compound is transported across cell membranes, which in turn may directly and positively affect the absorption, distribution, biotransformation and excretion of the compound. While the route of administration of the pharmaceutical composition is important, and various anatomical, physiological and pathological factors can critically affect bioavailability, the solubility of the compound is usually dependent upon the character of the particular salt form thereof, which it utilized. One of skill in the art will appreciate that an aqueous solution of the compound will provide the most rapid absorption of the compound into the body of a subject being treated, while lipid solutions and suspensions, as well as solid dosage forms, will result in less rapid adsorption of the compound.

Indications For Use of DPP-IV Inhibitors

DPP-IV is believed to contribute to the pathology and/or symptomology of several different diseases such that reduction of the activity of DPP-IV in a subject through inhibition may be used to therapeutically address these disease states. Examples of various diseases that may be treated using DPP-IV inhibitors are described herein. It is noted that additional diseases beyond those disclosed herein may be later identified as the biological roles that DPP-IV plays in various pathways becomes more fully understood.

One set of indications that DPP-IV inhibitors may be used to treat are those involving the prevention and treatment of diabetes and obesity, in particular type 2 diabetes mellitus, diabetic dislipidemia, conditions of impaired glucose tolerance (IGT), conditions of impaired fasting plasma glucose (IFG), metabolic acidosis, ketosis, appetite regulation and obesity.

DPP-IV inhibitors may also be used as immunosuppressants (or cytokine release suppressant drugs) for the treatment of among other things: organ transplant rejection; autoimmune diseases such as inflammatory bowel disease, multiple sclerosis and rheumatoid arthritis; and the treatment of AIDS.

DPP-IV inhibitors may also be used for treating various cancers including breast cancer, lung cancer and prostate cancer.

DPP-IV inhibitors may also be used to treat dermatological diseases such as psoriasis, rheumatoid arthritis (RA) and lichen planus.

DPP-IV inhibitors may also be used to treat infertility and amenorrhea.

DPP-IV inhibitors may also be used to modulate cleavage of various cytokines (stimulating hematopoietic cells), growth factors and neuropeptides. For example, such conditions occur frequently in patients who are immunosuppressed, for example, as a consequence of chemotherapy and/or radiation therapy for cancer.

DPP-IV inhibitors may also be used prevent or reduce cleavage of N-terminal Tyr-Ala from growth hormone-releasing factor. Accordingly, these inhibitors may be used in the treatment of short stature due to growth hormone deficiency (Dwarfism) and for promoting GH-dependent tissue growth or re-growth.

DPP-IV inhibitors may also be used to address disease states associated with cleavage of neuropeptides and thus may be useful for the regulation or normalization of neurological disorders.

For oncology indications, DPP-IV inhibitors may be used in conjunction with other agents to inhibit undesirable and uncontrolled cell proliferation. Examples of other anti-cell proliferation agents that may be used in conjunction with the DPP-IV inhibitors of the present invention include, but are not limited to, retinoid acid and derivatives thereof, 2-methoxyestradiol, ANGIOSTATIN™ protein, ENDOSTATIN™ protein, suramin, squalamine, tissue inhibitor of metalloproteinase-I, tissue inhibitor of metalloproteinase-2, plasminogen activator inhibitor-1, plasminogen activator inhibitor-2, cartilage-derived inhibitor, paclitaxel, platelet factor 4, protamine sulfate (clupeine), sulfated chitin derivatives (prepared from queen crab shells), sulfated polysaccharide peptidoglycan complex (sp-pg), staurosporine, modulators of matrix metabolism, including for example, proline analogs ((1-azetidine-2-carboxylic acid (LACA)), cishydroxyproline, d,1-3,4-dehydroproline, thiaproline, beta.-aminopropionitrile fumarate, 4-propyl-5-(4-pyridinyl)-2(3H)-oxazolone, methotrexate, mitoxantrone, heparin, interferons, 2 macroglobulin-serum, chimp-3, chymostatin, beta.-cyclodextrin tetradecasulfate, eponemycin; fumagillin, gold sodium thiomalate, d-penicillamine (CDPT), beta.-1-anticollagenase-serum, alpha.2-antiplasmin, bisantrene, lobenzarit disodium, n-2-carboxyphenyl-4-chloroanthronilic acid disodium or "CCA", thalidomide; angostatic steroid, carboxyaminoimidazole; metalloproteinase inhibitors such as BB94. Other anti-angiogenesis agents that may be used include antibodies, preferably monoclonal antibodies against these angiogenic growth factors: bFGF, aFGF, FGF-5, VEGF isoforms, VEGF-C, HGF/SF and Ang-1/Ang-2. Ferrara N. and Alitalo, K. "Clinical application of angiogenic growth factors and their inhibitors" (1999) Nature Medicine 5:1359-1364.

EXAMPLES

As used herein the symbols and conventions used in these processes, schemes and examples are consistent with those used in the contemporary scientific literature, for example, the Journal of the American Chemical Society or the Journal of Biological Chemistry. Standard single-letter or three-letter abbreviations are generally used to designate amino acid residues, which are assumed to be in the L-configuration unless otherwise noted. Unless otherwise noted, all starting materials were obtained from commercial suppliers and used without further purification. Specifically, the following abbreviations may be used in the examples and throughout the specification:

g (grams); mg (milligrams);
L (liters); mL (milliliters);
µL (microliters); psi (pounds per square inch);
M (molar); mM (millimolar);
i.v. (intravenous); Hz (Hertz);
MHz (megahertz); mol (moles);
mmol (millimoles); RT (ambient temperature);
min (minutes); h (hours);
mp (melting point); TLC (thin layer chromatography);
Tr (retention time); RP (reverse phase);
MeOH (methanol); i-PrOH (isopropanol);
TEA (triethylamine); TFA (trifluoroacetic acid);
TFAA (trifluoroacetic anhydride); THF (tetrahydrofuran);
DMSO (dimethylsulfoxide); EtOAc (ethyl acetate);
DME (1,2-dimethoxyethane); DCM (dichloromethane);
DCE (dichloroethane); DMF (N,N-dimethylformamide);
DMPU (N,N'-dimethylpropyleneurea); CDI (1,1-carbonyldiimidazole);
IBCF (isobutyl chloroformate); HOAc (acetic acid);
HOSu (N-hydroxysuccinimino); HOBT (1-hydroxybenzotriazole);
Et$_2$O (diethyl ether); EDCI (ethylcarbodimino hydrochloride);
BOC (tert-butyloxycarbonyl); FMOC (9-fluorenylmethoxycarbonyl);
DCC (dicyclohexylcarbodiimino); CBZ (benzyloxycarbonyl);
Ac (acetyl); atm (atmosphere);
TMSE (2-(trimethylsilyl)ethyl); TMS (trimethylsilyl);
TIPS (triisopropylsilyl); TBS (t-butyldimethylsilyl);
DMAP (4-dimethylaminopyridine); Me (methyl);
OMe (methoxy); Et (ethyl);
Et (ethyl); tBu (tert-butyl);
HPLC (high pressure liquid chromatography);
BOP (bis(2-oxo-3-oxazolidinyl)phosphinic chloride);
TBAF (tetra-n-butylammonium fluoride);
mCPBA (meta-chloroperbenzoic acid.

All references to ether or Et$_2$O are to diethyl ether; brine refers to a saturated aqueous solution of NaCl. Unless otherwise indicated, all temperatures are expressed in ° C. (degrees Centigrade). All reactions conducted under an inert atmosphere at RT unless otherwise noted. $^1$H NMR spectra were recorded on a Bruker Avance 400. Chemical shifts are expressed in parts per million (ppm). Coupling constants are in units of hertz (Hz). Splitting patterns describe apparent multiplicities and are designated as s (singlet), d (doublet), t (triplet), q (quartet), m (multiplet), br (broad).

Low-resolution mass spectra (MS) and compound purity data were acquired on a Waters ZQ LC/MS single quadrupole system equipped with electrospray ionization (ESI) source, UV detector (220 and 254 nm), and evaporative light scattering detector (ELSD). Thin-layer chromatography was performed on 0.25 mm E. Merck silica gel plates (60F-254), visualized with UV light, 5% ethanolic phosphomolybdic acid, Ninhydrin or p-anisaldehyde solution. Flash column chromatography was performed on silica gel (230-400 mesh, Merck).

It will be readily recognized that certain compounds made according to the present invention have atoms with linkages to other atoms that confer a particular stereochemistry to the compound (e.g., chiral centers). It is recognized that synthesis of compounds according to the present invention may result in the creation of mixtures of different stereoisomers (enantiomers, diastereomers). Unless a particular stereochemistry is specified, recitation of a compound is intended to encompass all of the different possible stereoisomers.

Various methods for separating mixtures of different stereoisomers are known in the art. For example, a racemic mixture of a compound may be reacted with an optically active resolving agent to form a pair of diastereoisomeric compounds. The diastereomers may then be separated in order to recover the optically pure enantiomers. Dissociable complexes may also be used to resolve enantiomers (e.g., crystalline diastereoisomeric salts). Diastereomers typically have sufficiently distinct physical properties (e.g., melting points, boiling points, solubilities, reactivity, etc.) that they can be readily separated by taking advantage of these dissimilarities. For example, diastereomers can typically be separated by chromatography or by separation/resolution techniques based upon differences in solubility. A more detailed description of techniques that can be used to resolve stereoisomers of compounds from their racemic mixture can be found in Jean Jacques Andre Collet, Samuel H. Wilen, Enantiomers, Racemates and Resolutions, John Wiley & Sons, Inc. (1981).

Compounds made according to the present invention can also be prepared as their individual stereoisomers by reacting a racemic mixture of the compound with an optically active resolving agent to form a pair of diastereoisomeric compounds, separating the diastereomers and recovering the optically pure enantiomer. While resolution of enantiomers can be carried out using covalent diastereomeric derivatives of compounds, dissociable complexes are preferred (e.g., crystalline diastereoisomeric salts). Diastereomers have distinct physical properties (e.g., melting points, boiling points, solubilities, reactivity, etc.) and can be readily separated by taking advantage of these dissimilarities. The diastereomers can be separated by chromatography or, preferably, by separation/resolution techniques based upon differences in solubility. The optically pure enantiomer is then recovered, along with the resolving agent, by any practical means that would not result in racemization. A more detailed description of the techniques applicable to the resolution of stereoisomers of compounds from their racemic mixture can be found in Jean Jacques Andre Collet, Samuel H. Wilen, Enantiomers, Racemates and Resolutions, John Wiley & Sons, Inc. (1981).

Synthetic Schemes of the Present Invention

Several illustrative reaction schemes according to the present invention are provided in the following examples. These reaction schemes may be used to mal-e DPP-IV inhibitors, as well as intermediates in the preparation of DPP-IV inhibitors.

In the reactions described hereinafter it may be necessary to protect reactive functional groups, for example hydroxy, amino, imino, thio or carboxy groups, where these are desired in the final product, to avoid their unwanted participation in the reactions. Conventional protecting groups may be used in accordance with standard practice, for examples see T. W. Greene and P. G. M. Wuts in "Protective Groups in Organic Chemistry" John Wiley and Sons, 1991.

Scheme 1:

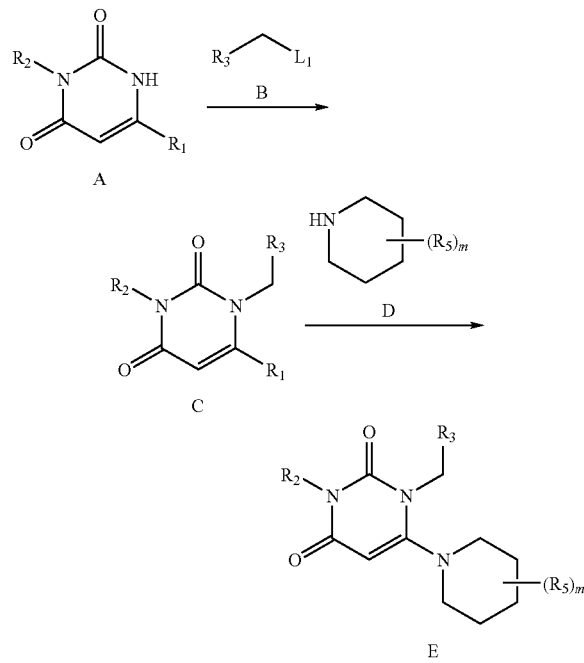

Compound C. A mixture of an optionally substituted 3,6-disubstituted uracil (A), Compound B and a base (e.g., $K_2CO_3$, $CSCO_3$ or diisopropylethylamine) in a solvent (e.g., DMSO, NMP or DMF) is optionally stirred for at least about 1 hour, and optionally at least about 2 hours, at a temperature between 50 and 70° C., and optionally at a temperature between 55 and 65° C. The reaction is optionally cooled (e.g., 20-30° C.), diluted with water and optionally extracted with an organic solvent (e.g., EtOAc or isopropanol). The organics are dried (e.g., over $MgSO_4$ or $Na_2SO_4$) and the solvent removed. The residue is optionally purified using any of a variety of purification techniques known in the art, including column chromatography.

Compound E. Compound C, an optionally substituted piperidine (D) and a base (e.g., sodium bicarbonate or $K_2CO_3$) are stirred (e.g., in a sealed tube) with an alcohol (e.g., MeOH, EtOH or isopropanol) at a temperature between 80 and 110° C., and optionally between 90 and 100° C., for at least about 1 h, and optionally at least about 2 h. The mixture is optionally dried by stirring the reactants with activated molecular sieves (4A). The reaction is filtered (e.g., through Celite), concentrated in vacuo, diluted with $CHCl_3$ or $CH_2Cl_2$, and then washed with water. The water phase is extracted with $CHCl_3$ or $CH_2Cl_2$, and the combined organic phases are washed with water, dried (e.g., $Na_2SO_4$), and filtered. TFA is added and the solution is then concentrated in vacuo. The residue is dissolved in a small amount of alcohol (e.g., MeOH), and $Et_2O$ or hexanes is added to force precipitation. The mixture can then be allowed to stand at RT overnight. Solvents are then decanted, and the solid washed with $Et_2O$ to give the TFA salt.

Alternatively, compound C can be reacted with an optionally substituted piperidine dihydrochloride (D) in water and an alcohol (e.g., isopropanol) at a temperature between 55 and 70° C., and optionally between 60 and 65° C., until completion (e.g., for at least about 12 h). The mixture is optionally cooled (e.g., to a temperature between 35 and 50° C.). The inorganic salts are removed by filtration and the filter cake washed (e.g., with a heated alcohol). The filtrate is optionally concentrated, diluted with a solvent (e.g., THF), and acidified with HCl while optionally maintaining the temperature below 20° C. The resultant slurry is optionally cooled, and agitated to allow crystals to grow. The slurry is filtered and the filter cake optionally washed and dried to give the HCl salt.

The HCl salt can be converted to a benzoic acid salt as follows. The HCl salt is dissolved in water at a temperature between 35 and 50° C., and optionally between 40 and 45° C., and washed (e.g., with isopropyl acetate) to remove dimer. The mixture is optionally heated, and free-based from the water layer into the organic layer (e.g., by the addition of solid potassium carbonate). The layers are separated and the organic layer optionally washed to remove residual salts. The organic solution is optionally concentrated, treated with 2B alcohol, and optionally concentrated again. The solution is optionally filtered and benzoic acid is added while optionally maintaining the temperature of the solution between 60 and 75° C., and optionally between 65 and 70° C. The solution is then crystallized (e.g., by cooling to a temperature between −5 and 10° C. and stirring). The solution is filtered, optionally washed, optionally conditioned under nitrogen, and dried, to provide the benzoic acid salt.

By varying the substituents on Compounds A, B and D, a wide variety of compounds can be synthesized using the methods of the present invention. By way of example, and not limitation, several variations of Scheme 1 are provided below as Schemes 1a-1e.

Scheme 1a:

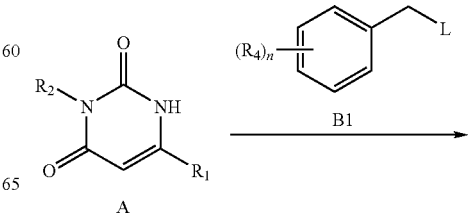

-continued
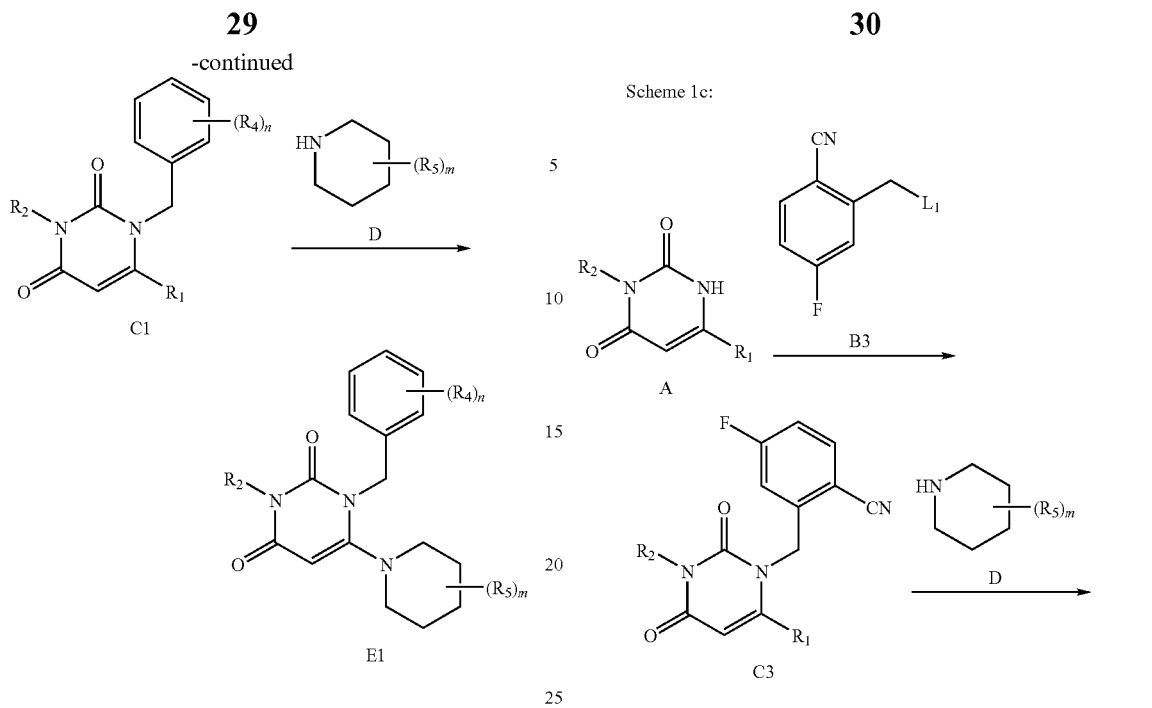
Scheme 1b:
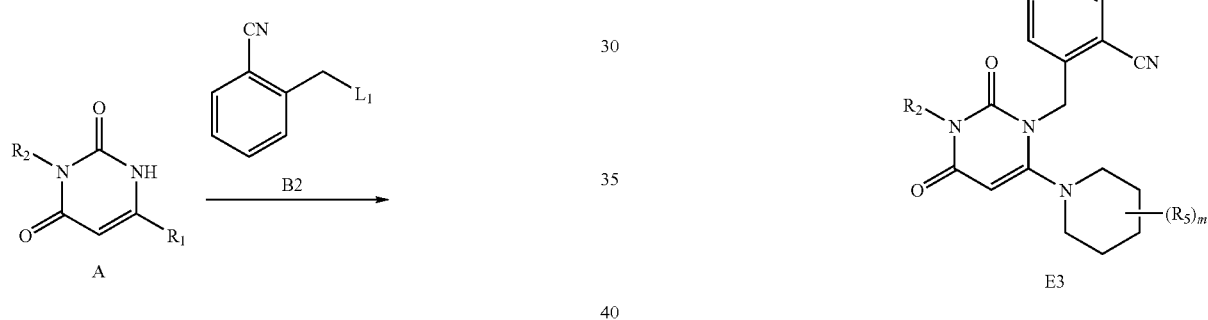
Scheme 1c:
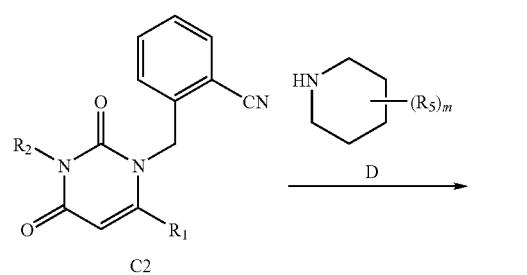
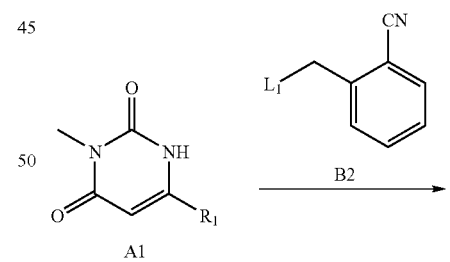
Scheme 1d:
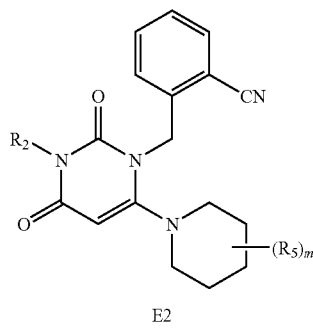
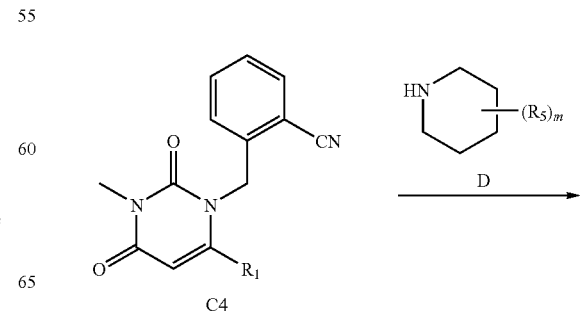

31

-continued

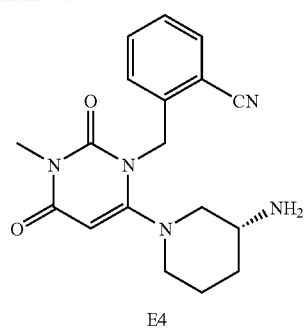

E4

Scheme 1e:

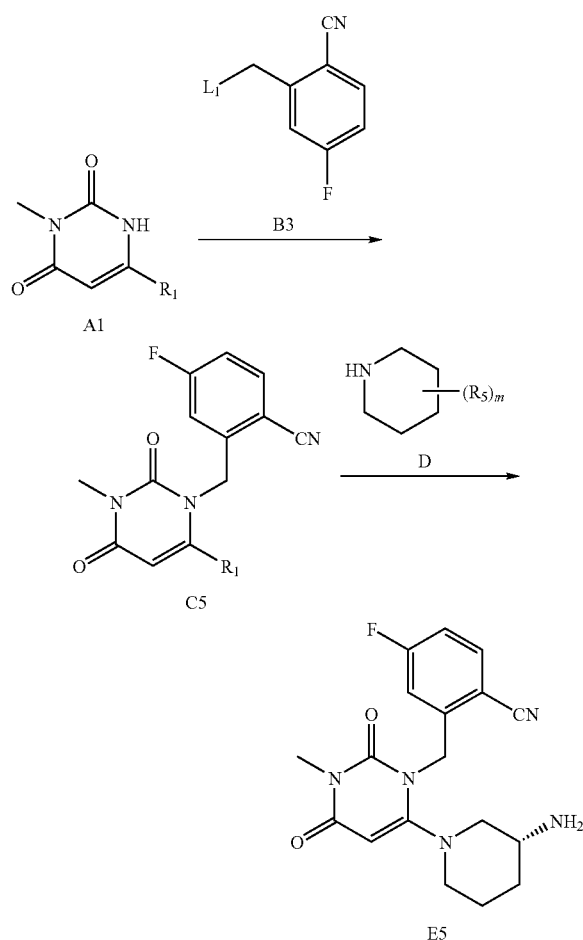

Scheme 2:

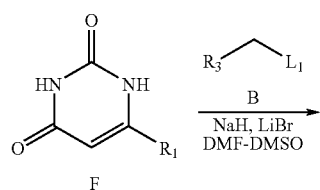

32

-continued

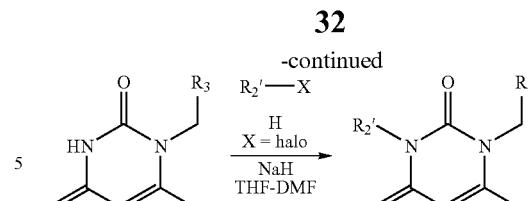

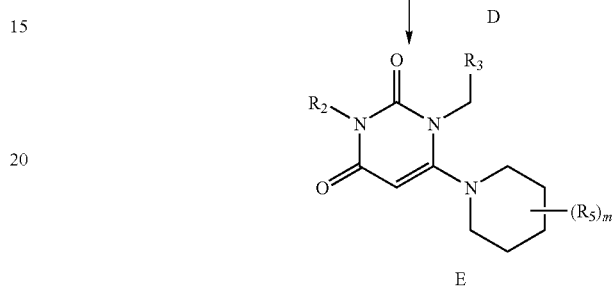

Compound G. To a solution of an optionally 6-substituted uracil (F) in a mixture of DMF-DMSO (6:1) under nitrogen at a temperature between −5 and 5° C., is added sodium hydride (60%) in portions. After at least about 15 minutes and optionally at least about 30 minutes, lithium bromide is added and the mixture stirred for at least about 15 min at a temperature between −5 and 5° C. A solution of Compound B in DMF is added. The mixture is then stirred at this temperature for at least about 30 minutes and optionally at least about 1 h, and then RT overnight. It will be understood that alkylation may be performed under standard conditions known in the art, including the use of a base such as NaH, LiH and the like in an organic solvent or mixture of solvents. The solvent may include DMSO, THF, DMF and the like, or mixtures thereof. In addition, additives may be used, including LiBr, LiI, NaI and the like.

The mixture is then evaporated and co-evaporated with water in vacuo to remove most of the solvent, and then poured into ice water. The precipitate is collected by filtration. The crude product is suspended in hot AcOEt-CHCl$_3$, sonicated, allowed to stand at a temperature of between −5 and 5° C. for at least about 30 minutes, and optionally at least about 1 h, and then filtered to give the title compound. It will also be understood by those skilled in the art that purification may be accomplished using various methods known in the art, including washing with an aqueous/organic solvent or mixture of solvents, recrystallization and/or column chromatography. Non-limiting examples of organic solvents and solvent mixtures may include ethyl acetate, isopropyl acetate, acetone, THF and the like.

Compound C. To a cold (between −5 and 5° C., and optionally about 0° C.) solution of an optionally 1,6-disubstituted uracil (G) in DMF-THF under nitrogen, is added NaH (60%) in portions, followed by -adding LiBr. The mixture is stirred at a temperature between −5 and 5° C. and optionally about 0° C., for at least about 10 minutes and optionally at least 20 minutes. Compound H is added and the flask sealed. The mixture is maintained at this temperature for at least about 5 minutes and optionally at least about 10 minutes; RT for at least about 1 h and optionally at least about 2 h; and at a temperature between 25 and 45° C. and optionally between 30 and 40° C. overnight. The product can then be concentrated in vacuo. It will be understood that alkylation may be performed under standard conditions known in the art, including the use of a base such as NaH, LiH or the like in an organic solvent or mixture of solvents. The solvent may include DMSO, TBIF, DMF and the like, or mixtures thereof. In addition, additives may be used, including LiBr, LiI, NaI and the like. For example, the alkylation can be performed using iodomethane and $K_2CO_3$ in acetone.

The residue is dissolved (e.g., in $CHCl_3$), washed with water and brine, dried (e.g., $Na_2SO_4$), filtered, and then concentrated in vacuo. The crude product is crystallized from, for example, THF-Hexanes to give the title compound. It will also be understood by those skilled in the art that Compound C may be purified in a variety of organic solvents or solvent mixtures. For example, Compound C can be purified by adding a mixture of dichloromethane and heptane. Optionally, Compound C may be further purified in an organic solvent or and 100° C., for at least about 1 h, and optionally at least about 2 h. The mixture is optionally dried by stirring the reactants with activated molecular sieves (4A). The reaction is filtered (e.g., through Celite), concentrated in vacuo, diluted with $CHCl_3$ or $CH_2Cl_2$, and then washed with water. The water phase is extracted with $CHCl_3$ or $CH_2Cl_2$, and the combined organic phases are washed with water, dried (e.g., $Na_2SO_4$), and filtered. TFA is added and the solution is then concentrated in vacuo. The residue is dissolved in a small amount of alcohol (e.g., MeOH), and $Et_2O$ or hexanes is added to force precipitation. The mixture can then be allowed to stand at RT overnight. Solvents are then decanted, and the solid washed with $Et_2O$ to give the TFA salt.

It will be understood that Scheme 2 provides an alternate method to that of Scheme 1. Specifically, Scheme 2 allows for substitution at the 3-position of Compound C after alkylation at the 1-position. Accordingly, Scheme 2 can be performed with Scheme 1 whenever $R_2$ of Scheme 1 is hydrogen or a protecting group.

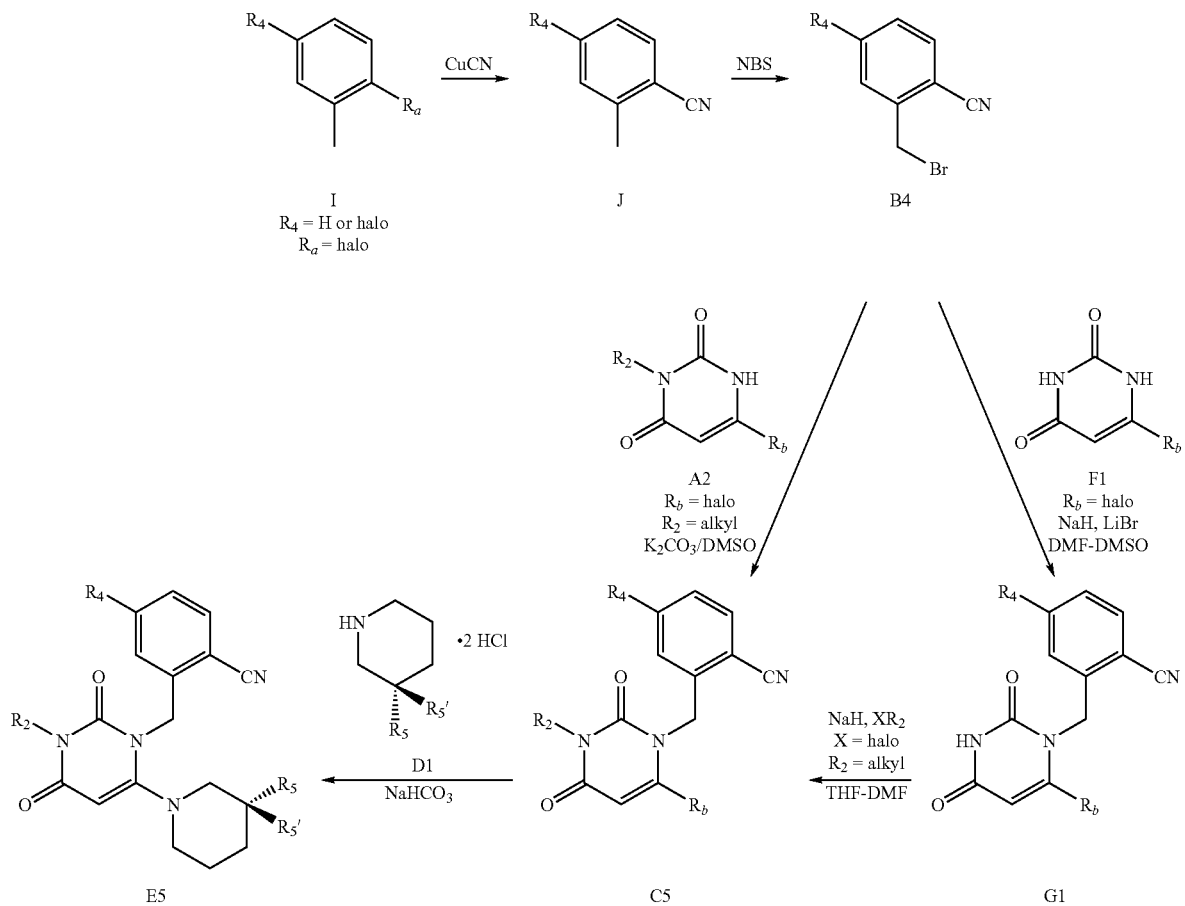

Scheme 3:

mixture of solvents such as dichloromethane, chloroform, acetonitrile, THF, ethyl acetate, isopropyl acetate and the like. In one particular embodiment, the product is purified and washed with ethyl acetate.

Compound E. Compound C, an optionally substituted piperidine (D) and sodium bicarbonate or $K_2CO_3$ are stirred in a sealed tube with an alcohol (e.g., MeOH or EtOH) at a temperature between 80 and 110° C., and optionally between 90

Compound J. A mixture of an optionally substituted 2-halotoluene (A) and CuCN in DMF is refluxed, optionally for at least 24 hours. The reaction is diluted with water and extracted with an organic solvent (e.g., hexane). The organics are optionally dried (e.g., over $MgSO_4$ or $Na_2SO_4$) and the solvent removed to give Compound J.

Compound B4. A mixture of an optionally substituted 2-methylbenzonitrile (J), N-bromosuccinimide (NBS) and azobisisobutylnitrile (AIBN) in $CCl_4$ is refluxed under nitrogen, optionally for at least 2 hours. The reaction is cooled to room temperature and the solid removed by filtration. The organic solution can be concentrated to Compound B4, which can be used in the next steps without further purification. Alternatively, the crude product can be purified using any of a variety of purification techniques known in the art, including washing with an aqueous/organic solvent or mixture of solvents, recrystallization and/or column chromatography.

Compound B4 can also be prepared as follows. 2-Methylbenzonitrile (J) in DCE is treated with AIBN and heated to a temperature between 70 and 80° C. DBH in DCE is added and the mixture stirred (e.g., for >30 min). The reaction is optionally monitored for completion by, for example, measuring the amount of residual benzonitrile using HPLC. Additional AIBN optionally can be added to move the reaction toward completion. A base (e.g., $K_2CO_3$, $CSCO_3$ or diisopropylethylamine) and diethyl phosphite are added, and the mixture is optionally stirred until completion. The mixture can be optionally washed and purified.

Compound G1. To a solution of a 6-halouracil (F1) in a mixture of DMF-DMSO (6:1) under nitrogen at a temperature between −5 and 5° C., is added sodium hydride (60%) in portions. After at least about 15 minutes and optionally at least about 30 minutes, lithium bromide is added and the mixture stirred for at least about 15 min at a temperature between −5 and 5° C. A solution of an optionally substituted 2-bromomethylbenzonitrile (B4) in DMF is added. The mixture is then stirred at this temperature for at least about 30 minutes and optionally at least about 1 h, and then RT overnight. It will be understood that alkylation may be performed under standard conditions known in the art, including the use of a base such as NaH, LiH and the like in an organic solvent or mixture of solvents. The solvent may include DMSO, THF, DMF and the like, or mixtures thereof. In addition, additives may be used, including LiBr, LiI, NaI and the like.

The mixture is then evaporated and co-evaporated with water in vacuo to remove most of the solvent, and then poured into ice water. The precipitate is collected by filtration. The crude product is suspended in hot $AcOEt-CHCl_3$, sonicated, allowed to stand at a temperature of between −5 and 5° C. for at least about 30 minutes, and optionally at least about 1 h, and then filtered to give the title compound. It will also be understood by those skilled in the art that purification may be accomplished using various methods known in the art, including washing with an aqueous/organic solvent or mixture of solvents, recrystallization and/or column chromatography. Non-limiting examples of organic solvents and solvent mixtures may include ethyl acetate, isopropyl acetate, acetone, THF and the like.

Compound C5. A mixture of a crude 3-alkyl-6-halouracil (A2), optionally substituted 2-bromomethylbenzonitrile (B4) and $K_2CO_3$ or $CsCO_3$ in a solvent (e.g., DMSO, DMF or NMP) is stirred for at least about 1 hour, and optionally at least about 2 hours, at a temperature between 50 and 70° C., and optionally at a temperature between 55 and 65° C. The reaction is diluted with water and extracted with an organic solvent (e.g., EtOAc). The organics are dried (e.g., over $MgSO_4$ or $Na_2SO_4$) and the solvent removed. The residue is optionally purified using any of a variety of purification techniques known in the art, including column chromatography.

Compound C5 can also be prepared as follows. To a solution of 3-alkyl-6-halouracil (A2) and a base (e.g., $K_2CO_3$, $CsCO_3$ or diisopropylethylamine) is added a solution of optionally substituted 2-bromomethylbenzonitrile (B4). The mixture is then heated to a temperature between 55 and 65° C. for 2 hours or until completion (as determined, for example, by HPLC). Heating is then stopped and the mixture is diluted with water. The resultant slurry is optionally stirred, filtered and dried.

Alternatively, the 2-(6-halo-3-alkyl-2,4-dioxo-3,4-dihydro-2H-pyrimidin-1-ylmethyl)-benzonitrile (C5) can be prepared as follows. To a cold (between −5 and 5° C., and optionally about 0° C.) solution of benzylated 6-halouracil (G1) in DMF-THF under nitrogen, is added NaH (60%) in portions, followed by adding LiBr. The mixture is stirred at a temperature between −5 and 5° C. and optionally about 0° C., for at least about 10 minutes and optionally at least 20 minutes. A haloalkane is added and the flask sealed. The mixture is maintained at this temperature for at least about 5 minutes and optionally at least about 10 minutes; RT for at least about 1 h and optionally at least about 2 h; and at a temperature between 25 and 45° C. and optionally between 30 and 40° C. overnight. The product can then be concentrated in vacuo. It will be understood that alkylation may be performed under standard conditions known in the art, including the use of a base such as NaH, LiH or the like in an organic solvent or mixture of solvents. The solvent may include DMSO, THF, DMF and the like, or mixtures thereof. In addition, additives may be used, including LiBr, LiI, NaI and the like. For example, the alkylation can be performed using iodomethane and $K_2CO_3$ in acetone.

The residue is dissolved (e.g., in $CHCl_3$), washed with water and brine, dried (e.g., $Na_2SO_4$), filtered, and then concentrated in vacuo. The crude product is crystallized from, for example, THF-Hexanes to give the title compound. It will also be understood by those skilled in the art that the benzonitrile may be purified in a variety of organic solvents or solvent mixtures. For example, the benzonitrile can be purified by adding a mixture of dichloromethane and heptane. Optionally, the benzonitrile may be further purified in an organic solvent or mixture of solvents such as dichloromethane, chloroform, acetonitrile, THF, ethyl acetate, isopropyl acetate and the like. In one particular embodiment, the product is purified and washed with ethyl acetate.

Compound E5. A 2-(6-Halo-3-alkyl-2,4-dioxo-3,4-dihydro-2-H-pyrimidin-1-ylmethyl)-benzonitrile (C5), a 3-substituted-piperidine dihydrochloride (D1) and sodium bicarbonate or $K_2CO_3$ are stirred in a sealed tube with an alcohol (e.g., MeOH or EtOH) at a temperature between 80 and 110° C., and optionally between 90 and 100° C., for at least about 1 h, and optionally at least about 2 h. The mixture is optionally dried by stirring the reactants with activated molecular sieves (4A). The reaction is filtered (e.g., through Celite), concentrated in vacuo, diluted with $CHCl_3$ or $CH_2Cl_2$, and then washed with water. The water phase is extracted with $CHCl_3$ or $CH_2Cl_2$, and the combined organic phases are washed with water, dried (e.g., $Na_2SO_4$), and filtered. TFA is added and the solution is then concentrated in vacuo. The residue is dissolved in a small amount of alcohol (e.g., MeOH), and $Et_2O$ or hexanes is added to force precipitation. The mixture can then be allowed to stand at RT overnight. Solvents are then decanted, and the solid washed with $Et_2O$ to give the TFA salt.

It will be understood by those skilled in the art that condensation with the amine or amine hydrochloride may be performed in a solvent or mixture of solvents with a base, such as potassium carbonate, sodium bicarbonate and the like, or mixtures thereof. The solvent may comprise both protic and aprotic solvents, or mixtures thereof. For example, the solvent may comprise a mixture of isopropyl alcohol and water.

The benzonitrile product may be isolated as the free base. The free base form can be isolated by washing the crude product with water, drying (e.g., over $Na_2SO_4$ or $MgSO_4$), filtering and concentrating the product. The free base product can then be dissolved in THF. Alternatively, the free base could be dissolved in other solvents, such as dioxane, acetonitrile, ethyl acetate, dichloromethane, etc., or mixtures thereof. It will also be understood that the product may be purified using any of a variety of techniques known in the art, including by column chromatography and washing with an organic solvent or mixture of solvents. Non-limiting examples of solvent or solvent mixtures that can be used include isopropyl acetate, ethyl acetate, dichloromethane, heptane, and the like.

The free base product can also be prepared as follows. A mixture of Compound C5, an alcohol (e.g., EPA), (R)-3-amino-piperidine dihydrochloride and a base (e.g., potassium carbonate) is heated at a temperature between 55 and 65° C. until completion (e.g., for >20 hours) as determined, for example, by HPLC. An organic solvent or mixture of solvents such as dichloromethane, chloroform, acetonitrile, THF, ethyl acetate, isopropyl acetate and the like is then added. The resultant slurry is optionally filtered, washed and concentrated.

Alternatively, the benzonitrile product can be converted to a variety of acid addition salts. For example, the benzonitrile product (e.g., about 10 mg) in an alcohol (e.g., MeOH, 1 mL) is treated with various acids (e.g., between 0.8 and 1.5 equivalents and optionally about 1.05 equivalents). The solutions are allowed to stand open to the air, optionally for at least about 2 days and optionally for at least about 3 days. If a precipitate forms, the mixture is filtered and the salt dried. If no solid forms, the mixture is concentrated in vacuo and the residue isolated. Using this approach, salts including, but not limited to, those produced from the following acids can be prepared: benzoic, p-toluenesulfonic, succinic, R-(-)-Mandelic and benzenesulfonic.

The benzoic acid salt can be formed by treating the benzonitrile product with benzoic acid using conventional methods for the formation of acid addition salts.

Likewise, the HCl salt can be obtained by suspending the TFA salt in DCM or CHCl$_3$, washing with saturated Na$_2$CO$_3$ or K$_2$CO$_3$, drying the organic layer in vacuo, dissolving the residue in a solvent (e.g., acetonitrile), adding between 1 and 2 equivalents, and optionally between 1.2 and 1.8 equivalents, of HCl in an organic solvent (e.g., dioxane) at a temperature between −5 and 5° C., and removing the solvent.

The HCl salt can also be prepared as follows. To a solution of free base in CH$_2$Cl$_2$ or CHCl$_3$ is added hydrochloric acid (e.g., 2 M HCl). The slurry is optionally stirred, filtered and washed (e.g., with CH$_2$Cl$_2$ or CHCl$_3$, and then THF). The material is then slurried in THF, filtered and optionally dried.

Further, the toluenesulfonate salt can be prepared as follows. A stock solution of free base (e.g., 200µ of a 0.03M solution) is dissolved in dichoromethane and concentrated under a slow stream of nitrogen. The resulting free base is dissolved in a solvent (e.g., 150 µL of acetic acid, acetone, ethanol, THF or dichloromethane) and the solution shaken for at least 5 minutes and optionally at least 10 minutes. The shaken solution is then charged with toluenesulfonic acid (about 1.05 equivalents; 50 µL of a 0.126M solution) in dioxane. The solution is shaken optionally for at least 2 hours and optionally at least 3 hours. The solvents are then removed under a stream of nitrogen to provide the toluenesulfonate salt.

The toluenesulfonate salt can also be prepared by dissolving the free base (e.g., about 2 g) in about 10 volumes of acetonitrile. The solution is heated to a temperature between 65 and 85° C., and optionally between 70 and 80° C., for at least about 5 minutes and optionally at least about 10 minutes. Then, p-toluenesulfonic acid (e.g., 1.05 equivalents) is added and the solution held at a temperature between 65 and 85° C., and optionally between 70 and 80° C., for at least about 5 minutes. The temperature is optionally ramped down (at about 25° C./hr) and the mixture stirred at room temperature overnight. The product can be dried in a vacuum oven at a temperature between 40 and 60° C., and optionally between 45 and 55° C., and pressure between 690 and 710 mm Hg, and optionally about 698.5 mm Hg, with a nitrogen sweep for at least about 15 hours and optionally at least about 18 hours.

In addition, the methanesulfonate salt can be prepared as follows. The benzonitrile product (e.g., a 10.5 g aliquot) is mixed with isopropylacetate (e.g., 400 mL). The slurry is heated to a temperature between 60 and 90° C., optionally between 70 and 80° C., and optionally about 75° C., and filtered (e.g., through #3 Whatman filter paper). The solution is reheated to a temperature between 60 and 90° C., optionally between 70 and 80° C., and optionally about 75° C., and methanesulfonic acid (e.g., 30.84 mL of a 1M solution) is added. The suspension is cooled to room temperature, optionally at a rate of about 20° C./hr. After at least about 30 minutes and optionally at least about 1 hr at room temperature, the solid is filtered and dried to obtain the methanesulfonate salt.

The succinate salt can be prepared as follows. To a mixture of the HCl salt of Compound E5 and CH$_2$Cl$_2$ or CHCl$_3$ is added a base (e.g., a 50% NaOH solution) until the pH of the mixture is >11, and optionally >12. The mixture optionally is stirred and the organic layer separated. The aqueous layer is extracted (e.g., with CH$_2$Cl$_2$ or CHCl$_3$) and the combined organic layers are washed with water. The organic layer optionally is filtered and concentrated to afford the free base. The free base is slurried (e.g., in THF and/or IPA) and heated (e.g., at a temperature between 55 and 65° C.) until complete dissolution of the free base is observed. A solution of succinic acid is added, optionally while maintaining the mixture temperature at >50° C. The material is optionally stirred, filtered, washed and dried.

Scheme 4:

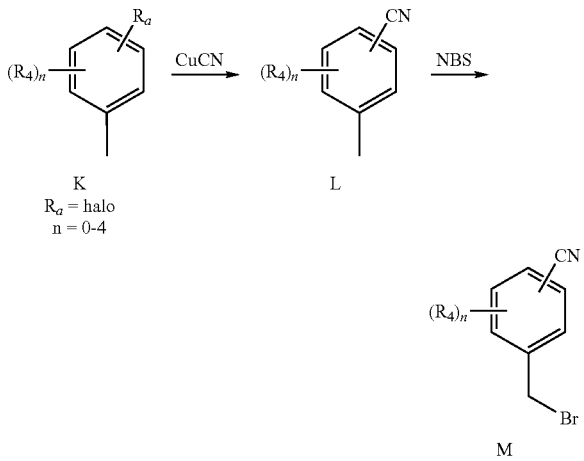

Compound L. A mixture of an optionally substituted halotoluene (K) and CuCN in DMF is refluxed, optionally for at least 24 hours. The reaction is diluted with water and extracted with an organic solvent (e.g., hexane, ethylacetate, etc.). The organics are optionally dried (e.g., over MgSO$_4$ or Na$_2$SO$_4$) and the solvent removed to give Compound L.

Compound M. A mixture of an optionally substituted methylbenzonitrile (L), N-bromosuccinimide (NBS) and azobisisobutylnitrile (AIBN) in CCl$_4$ is refluxed under nitrogen, optionally for at least 2 hours. The reaction is cooled to room temperature and the solid removed by filtration. The organic solution can be concentrated to give Compound M, which can be used in the next steps without further purification. Alternatively, the crude product can be purified using any of a variety of purification techniques known in the art, including washing with an aqueous/organic solvent or mixture of solvents, recrystallization and/or column chromatography.

Scheme 5:

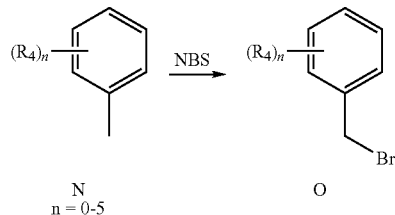

Compound O. A mixture of an optionally substituted methylbenzene (N), N-bromosuccinimide (NBS) and azobisisobutylnitrile (AIBN) in CCl$_4$ is refluxed under nitrogen, optionally for at least 2 hours. The reaction is cooled to room temperature and the solid removed by filtration. The organic solution can be concentrated to give compound O, which can be used in the next steps without further purification. Alternatively, the crude product can be purified using any of a variety of purification techniques known in the art, including washing with an aqueous/organic solvent or mixture of solvents, recrystallization and/or column chromatography.

In each of the above steps, the isolation and/or purification steps of the intermediate compounds may be avoided if the intermediates from the reaction mixture are obtained as relatively pure compounds and the by-products or impurities of the reaction mixture do not interfere with the subsequent reaction steps. Where feasible, one or more isolation steps may be eliminated to provide shorter processing times, and the elimination of further processing may also afford higher overall reaction yields.

By varying the substituent groups in the above schemes, a wide variety of different DPP-IV inhibitors may be synthesized. In the above reaction scheme, the various substituents may be selected from among the various substituents otherwise taught herein.

Descriptions of the syntheses of particular compounds based on the above reaction schemes are set forth herein.

EXAMPLES OF DPP-IV INHIBITORS

The present invention is further exemplified, but not limited by, the following examples that describe the synthesis of particular compounds.

Experimental Methods

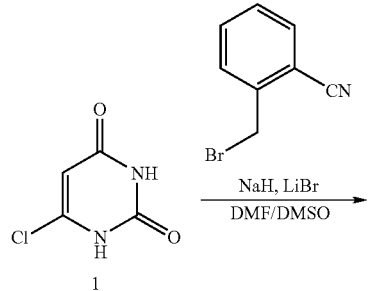

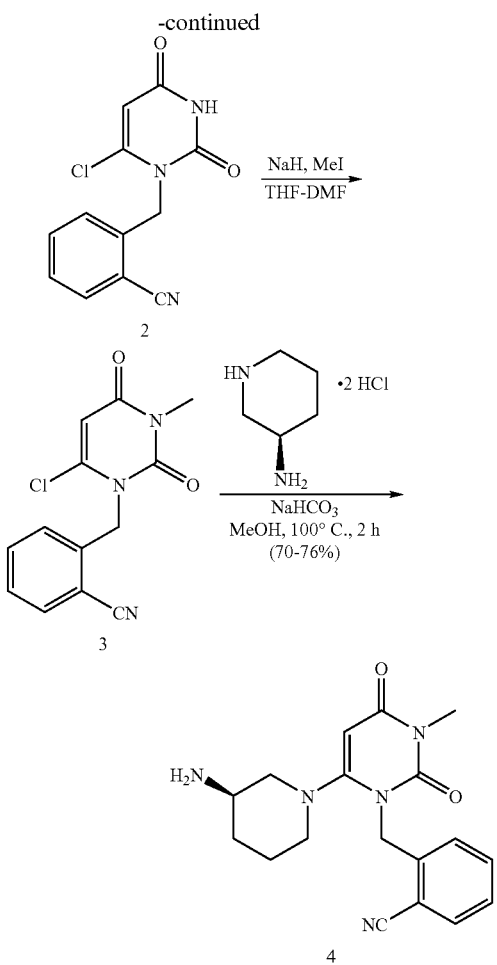

2-(6-Chloro-2,4-dioxo-3,4-dihydro-2H-pyrimidin-1-ylm-ethyl)-benzonitrile (2). To a solution of 6-chlorouracil (20 g, 122 mmol) in a mixture of DMF-DMSO (6:1, 600 mL) under nitrogen at 0° C., was added sodium hydride (60%, 5.5 g, 137 mmol) in portions. After 0.5 h, lithium bromide (8 g, 96 mmol) was added into the mixture and stirred for 15 min at 0° C. A solution of α-Bromo-o-tolunitrile (25.1 g, 128 mmol) in DMF (30 mL) was added dropwise, and stirred at this temperature for 1 h, and then RT overnight. The mixture was evaporated and co-evaporated with water in vacuo to remove most of the DMF, and then poured into ice water (1 L). The precipitate was collected by filtration. The crude product was suspended in hot AcOEt-CHCl$_3$ and sonicated for 5 min, allowed to stand at 0° C. for 1 h, and then filtered to give a white solid of the title compound (19 g) in 54% yield. $^1$H-NMR (400 MHz, DMSO): δ 11.82 (s, 1H), 7.87 (d, 1H, J=7.6 Hz), 7.71 (t, 1H, J=7.6 Hz), 7.51 (t, 1H, J=7.6 Hz), 7.37 (d, 1H, J=8 Hz), 6.06 (s, 1H), 5.31 (s, 2H). MS (ES) [m+H] calc'd for $C_{12}H_9ClN_3O_2$, 262.0; found 262.0.

2-(6-Chloro-3-methyl-2,4-dioxo-3,4-dihydro-2H-pyrimidin-1-ylmethyl)-benzonitrile (3). To a cold (0° C.) solution of benzylated 6-chlorouracil 2 (10 g, 38 mmol) in DMF-TH-F (1:1, 300 mL) under nitrogen, was added NaH (60%, 1.6 g, 39.9 mmol) in portions, followed by adding LiBr (2 g). The mixture was stirred at RT for 20 min. After adding iodomethane (5.4 mL, 76 mmol), the flask was sealed and stirred at this temperature for 10 min, RT for 2 h, and 35° C. overnight, and then concentrated in vacuo. The residue was dissolved in CHCl$_3$ and washed with water and brine, dried (Na₂SO₄), and filtered then concentrated in vacuo. The crude product was crystallized from THF-Hexanes to give 7.6 g (72%) of the title compound 3. ¹H NMR (400 MHz, DMSO): δ 7.87 (d, 1H, J=7.6 Hz), 7.70 (t, 1H, J=7.6 Hz), 7.51 (t, 1H, J=7.6 Hz), 7.40 (d, 1H, J=8 Hz), 6.21 (s, 1H), 5.38 (s, 2H), 3.28 (s, 3H). MS (ES) [m+H] calc'd for C₁₃H₁₁ClN₃O₂, 276.1; found 276.1.

2-{6-[3(R)-Amino-piperidin-1-yl]-3-methyl-2,4-dioxo-3,4-dihydro-2H-pyrimidin-1-ylmethyl}-benzonitrile (4). 2-(6-Chloro-3-methyl-2,4-dioxo-3,4-dihydro-2-H-pyrimidin-1-ylmethyl)-benzonitrile (330 mg, 1.08 mmol), (R)-3-amino-piperidine dihydrochloride (246 mg, 1.4 mmol) and sodium bicarbonate (500 mg, 5.4 mmol) were stirred with 200 mg activated molecular sieves (4A) in dry MeOH (5 mL) at 100° C. for 2 h. The reaction was filtered through Celite, concentrated in vacuo, and then diluted with CHCl₃, and washed with water. The water phase was extracted with CHCl₃ and the combined organic phases were washed with water, dried (Na₂SO₄), and filtered. TFA (1 mL) was added into the solution which was then concentrated in vacuo. The residue was dissolved in a small amount of MeOH, and Et₂O was added to force precipitation. The mixture was allowed to stand at RT overnight. Solvents were decanted, and the solid was washed with Et₂O two times to give 270 mg TFA salt of product 4 as an off-white powder. The TFA salt of 4 has ¹H-NMR (400 MHz, CDCl₃-CD₃OD 10:1): δ 7.82 (d, 1H, J=7.6 Hz), 7.65 (t, 1H, J=7.6 Hz), 7.46 (t, 1H, J=7.6 Hz), 7.23 (d, 1H, J=8.0 Hz), 5.42 (s, 1H), 5.50-5.00 (ABq, 2H, J=41.6, 15.2 Hz), 3.30 (m, 2H), 3.16 (s, 3H), 2.91 (m, 1H), 2.76 (m, 2H), 1.93 (m, 1H), 1.79 (m, 1H), 1.51 (m, 2H). MS (ES) [m+H] calc'd for C₁₈H₂₂N₅O₂, 340.2; found, 340.2.

The benzoic acid salt was formed by treating the benzonitrile product with benzoic acid to form 2-[6-(3-amino-piperidin-1-yl)-3-methyl-2,4-dioxo-3,4-dihydro-2H-pyrimidin-1-ylmethyl]-benzonitrile benzoate (4). Preparation and isolation of the benzoate salt was performed by conventional methods for the formation of acid addition salts. ¹H-NMR (400 MHz, CDCl₃-CD₃OD 10:1): δ 7.82 (d, 1H, J=7.6 Hz), 7.65 (t, 1H, J=7.6 Hz), 7.46 (t, 1H, J=7.6 Hz), 7.23 (d, 1H, J=8.0 Hz), 5.42 (s, 1H), 5.50-5.00 (ABq, 2H, J=41.6, 15.2 Hz), 3.30 (m, 2H), 3.16 (s, 3H), 2.91 (m, 1H), 2.76 (m, 2H), 1.93 (m, 1H), 1.79 (m, 1H), 1.51 (m, 2H). MS (ES) [m+H] calc'd for C₁₈H₂₂N₅O₂, 340.2; found, 340.2.

Following the same procedure described above, the HCl addition salt was prepared as follows. A free base form of 4 was isolated after the crude product was washed with water, dried over Na₂SO₄, filtered and concentrated. The free base product was then dissolved in THF. The solution was then stirred and 1.2 equivalents of 4M HCl in dioxane was added dropwise. After 10 min stirring, the suspended mixture was allowed to stand at RT for 1 h, and then filtered to give the solid HCl salt form of 4. ¹H-NMR (400 MHz, DMSO-D6): δ 7.82 (d, 1H, J=7.6 Hz), 7.65 (t, 1H, J=7.6 Hz), 7.46 (t, 1H, J=7.6 Hz), 7.23 (d, 1H, J=8.0 Hz), 5.42 (s, 1H), 5.20, 5.08 (ABq, 2H, J=41.6, 15.2 Hz), 3.30 (m, 2H), 3.16 (s, 3H), 2.91 (m, 1H), 2.76 (m, 2H), 2.50 (bs, 2 H), 1.93 (m, 1H), 1.79 (m, 1H), 1.51 (m, 2H). MS (ES) [m+H] calc'd for C₁₈H₂₂N₅O₂, 340.2; found, 340.2.

Further, the toluenesulfonate salt was prepared as follows. A 200 µL aliquot of a 0.03M stock solution of free base was dissolved in dichoromethane and concentrated under a slow stream of nitrogen. The resulting free base was dissolved in 150 µL of solvent (e.g., acetic acid, acetone, ethanol, THF or dicholormethane) and the solution shaken for 10 minutes. The shaken solution was then charged with 50 µL of a 0.126M solution of touenesulfonic acid (1.05 equivalents) in dioxane. The solution was shaken for 3 hours, followed by removal of the solvents under a stream of nitrogen to provide the toluenesulfonate salt.

The toluenesulfonate salt was also prepared by dissolving 2 g of the free base in 10 volumes of acetonitrile and heating the solution to 75° C. for 10 minutes. Then p-toluenesulfonic acid (1.05 equivalents) was added and the solution held at 75° C. for 5 minutes. The temperature was ramped down (at about 25° C./hr) and stirred at room temperature overnight. The product (2.64 g) was dried in a vacuum oven at 50° C. and 698.5 mm Hg with a nitrogen sweep for 18 hours.

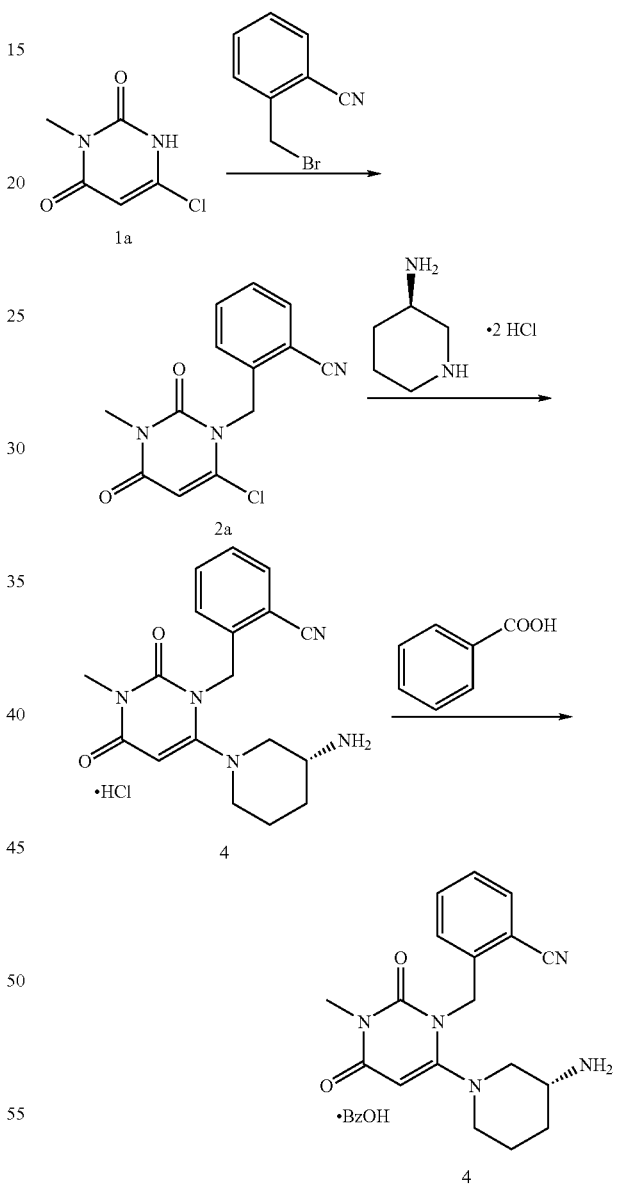

2-((6-chloro-3-methyl-2,4-dioxo-3,4-dihydropyrimidin-1 (2H)-yl)methyl)benzonitrile (2a). To a solution of 6-chloro-3-methyluracil (1 equiv., 1 wt.), N-methylpyrrolidone (NMP; 4 vol.) and diisopropylethylamine (Hünig's base, 1.5 equiv., 1.21 wt.), was added a solution of α-bromotoluoylnitrile (1.1 equiv., 1.35 wt.) and toluene (4 vol.). The mixture was heated at 60-70° C. and agitated for 2-3 hrs, or until completion. The solution was then cooled to 20-30° C., quenched with deionized water (5 vol.) at less than 35° C., agitated for 30 min, cooled to 0-5° C., and then agitated for at least one hour. The resultant slurry was filtered, reslurried in isopropanol, displacement washed with isopropanol, and dried under vacuum at 55-60° C.

(R)-2-((6-(3-aminopiperidin-1-yl)-3-methyl-2,4-dioxo-3,4-dihydropyrimidin-1(2H)-yl)methyl)benzonitrile (4). Compound 2a was reacted with 1.1 equivalents of (R)-3-aminopiperidine dihydrochloride in isopropanol and water at 60-65° C. until completion (e.g., 16 hrs). Potassium carbonate (4.4 equiv.) was added (over 1-1.5 hours) while maintaining the temperature between 60 and 65° C. After cooling to 40-45° C., the inorganic salts were removed by filtration and the filter cake was washed with heated (e.g., 40-45° C.) isopropanol. The filtrate was concentrated to approximately 5 volumes, diluted with THF at 0-5° C., and acidified with 6M hydrochloric acid while maintaining the temperature below 15° C. The resultant slurry was cooled to 0-5° C., agitated to allow crystals to grow (e.g., 12 hrs or more), and then filtered. The filter cake was displacement washed twice with isopropanol (2.5 vol. per wash) and dried to provide the HCl salt of compound 4 as a white crystalline solid.

The HCl salt of compound 4 was dissolved in water at 40-45° C. and washed with isopropyl acetate to remove the dimer. The resulting mixture was heated to 50° C. and free-based from the water layer into the organic layer by the addition of solid potassium carbonate, while maintaining the batch temperature at 50-55° C. The layers were separated and the aqueous layer was extracted once more at 50° C. with isopropyl acetate. The organic layers were then combined and washed with 23% sodium chloride in water to remove residual potassium salts. The organic solution was concentrated under reduced pressure to approximately 4 volumes. 2B alcohol (4 vol.) was added and the solution was concentrated under reduced pressure until 4 volumes remained. Another 4 volumes of 2B alcohol was added and the solution was again concentrated under reduced pressure until 4 volumes remained. The resulting solution was clarified through a Niagara filter, followed by a 1.2 micron in-line filter, to remove precipitated sodium chloride and particulates. A hot (65-70° C.) solution of benzoic acid in 2B ethanol was added while maintaining the solution at 65-70° C. The solution was then crystallized by cooling to 0-5° C. and stirring for 12 hrs. The solution was filtered, followed by slurry and displacement washes with 2B alcohol. The wet cake was then conditioned under nitrogen for 2 hours. The cake was dried for 8 hrs at 40-50° C., to provide the benzoic acid salt of compound 4 as a white crystalline solid.

Compound 5

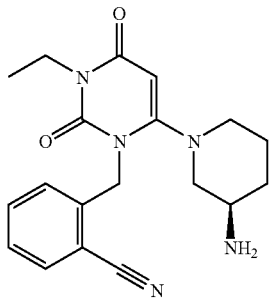

2-{6-[3(R)-Amino-piperidin-1-yl]-3-ethyl-2,4-dioxo-3,4-dihydro-2H-pyrimidin-1-ylmethyl}-benzonitrile TFA salt (5). The title compound, 5, was prepared from compound 2 using the procedures described in the preparation of compounds 3 and 4, except that ethyl bromide was used in place of iodomethane. $^1$H-NMR (400 MHz, CDCl$_3$-CD$_3$OD 10:1): δ 7.66 (d, J=7.8 Hz, 1 H), 7.59 (td, J=7.8, 1.4 Hz, 1 H), 7.40 (t, J=7.6 Hz, 1 H), 7.26 (d, J=7.6 Hz, 1 H), 5.41 (s, 1 H), 5.13-5.23 (ABq, 2H, J=41.6, 15.2 Hz), 3.91 (q, J=7.1 Hz, 2 H), 3.37 (m, 2 H), 2.87-2.98 (m, 2 H), 2.70 (m, 1 H), 2.12 (m, 1 H), 1.88 (m, 1 H), 1.67 (m, 2 H), 1.15 (t, J=6.9 Hz, 3 H). MS (ES) [m+H] calc'd for C$_{19}$H$_{24}$N$_5$O$_2$, 354.2; found, 354.2.

Compound 6

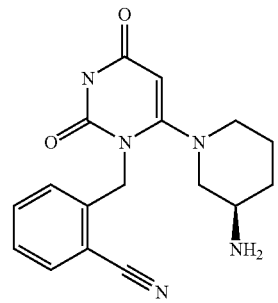

2-{6-[3(R)-Amino-piperidin-1-yl]-2,4-dioxo-3,4-dihydro-2H-pyrimidin-1-ylmethyl}-benzonitrile (6). The title compound 6 was prepared from compound 2 by the procedure used in the preparation of compound 4. $^1$H-NMR (400 MHz, CDCl$_3$-CD$_3$OD 10:1): δ 7.65 (d, J=7.5 Hz, 1 H), 7.58 (t, J=7.8 Hz, 1 H), 7.39 (t, J=7.5 Hz, 1 H), 7.27 (d, J=7.8 Hz, 1 H), 5.32 (s, 1 H), 5.13-5.13 (ABq, 2H, J=30.0, 15.0 Hz), 3.39 (m, 2 H), 2.95 (m, 2 H), 2.69 (m, 1 H), 2.12 (m, 1 H), 1.85 (m, 1 H), 1.64 (m, 2 H). MS (ES) [m+H] calc'd for C$_{17}$H$_{20}$N$_5$O$_2$, 326.2; found, 326.2.

Compound 7

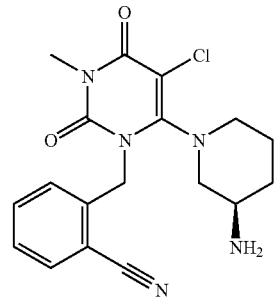

2-{6-[3(R)-Amino-piperidin-1-yl]-5-chloro-3-methyl-2,4-dioxo-3,4-dihydro-2H-pyrimidin-1-ylmethyl}-benzonitrile (7). Compound 4 (40 mg, 0.1 mmol) in CHCl$_3$ (2 mL) was treated with SOCl$_2$ (200 μL) at 100° C. for 30 min, concentrated, and then purified by LC-MS to give the title compound 7. $^1$H-NMR (400 MHz, CDCl$_3$-CD$_3$OD 10:1): δ 7.73 (d, J=7.6 Hz, 1 H), 7.64 (t, J=7.6 Hz, 1 H), 7.45 (t, J=7.6 Hz, 1 H), 7.14 (d, J=8.1 Hz, 1 H), 5.32-5.42 (m, 2 H), 3.43 (s, 3 H), 3.33-3.40 (m, 2 H), 3.17 (m, 2 H), 2.87 (s, 1 H), 2.08 (m, 1 H), 1.70 (m, 1 H), 1.32-1.43 (m, 2 H). MS (ES) [m+H] calc'd for $C_{18}H_{21}ClN_5O_2$, 374.1; found, 374.1.

Compound 8

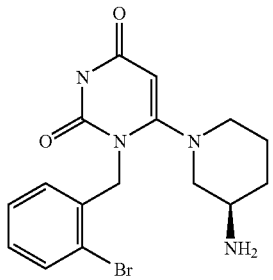

6-[3 (R)-Amino-piperidin-1-yl]-1-(2-bromo-benzyl)-1H-pyrimidine-2,4-dione (8). The title compound was prepared in two steps. The first step was accomplished using the procedure for the preparation of compound 2, except that 2-bromobenzylbromide was used in the place of α-Bromo-o-tolunitrile. The crude product was then converted to the title compound by the method used in the preparation of compound 4. $^1$H-NMR (400 MHz, $CDCl_3$-$CD_3OD$ 10:1): δ 7.52 (d, J=8.1 Hz, 1 H), 7.24 (t, J=7.8 Hz, 1 H), 7.10 (t, J=7.8 Hz, 1 H), 6.89 (d, J=7.579 Hz, 1 H), 5.27 (s, 1 H), 4.92-5.04 (ABq, J=34.1, 15.0 Hz, 2 H), 3.27 (bd, J=10.4 Hz, 1 H), 3.09-3.18 (m, 1 H), 2.89 (m, 1 H), 2.70 (t, J=10.9 Hz, 1 H), 2.48 (t, J=12.0 Hz, 1 H), 2.03 (m, 1 H), 1.60-1.71 (m, 1 H), 1.42-1.53 (m, 2 H). MS (ES) [m+H] calc'd for $C_{16}H_{20}BrN_4O_2$, 379.1; found, 379.1.

Compound 9

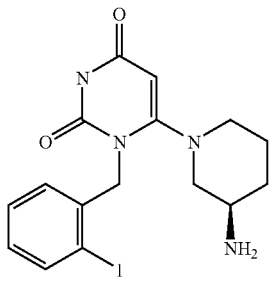

6-[3 (R)-Amino-piperidin-1-yl]-1-(2-iodo-benzyl)-1H-pyrimidine-2,4-dione (9). The title compound was prepared by the procedure described in the preparation of compound 8, except that 2-iodobenzyl chloride was used as the benzylating reagent. $^1$H-NMR (400 MHz, $CDCl_3$-$CD_3OD$ 10:1): δ 7.76 (d, J=7.6 Hz, 1 H), 7.21 (t, J=7.3 Hz, 1 H), 6.89 (t, J=7.2 Hz, 1 H), 6.79 (d, J=7.3 Hz, 1 H), 5.26 (s, 1 H), 4.79-4.92 (ABq, J=34.1, 6.7.0 Hz, 2H), 3.27 (m, 1 H), 3.13 (s, 1 H), 2.85 (d, J=11.6 Hz, 1 H), 2.70 (m, 1 H), 2.41 (m, 1 H), 2.02 (m, 1 H), 1.60 (m, 1 H), 1.45 (m, 2 H). MS (ES) [m+H] calc'd for $C_{16}H_{20}IN_4O_2$, 427.1; found, 427.1.

Compound 10

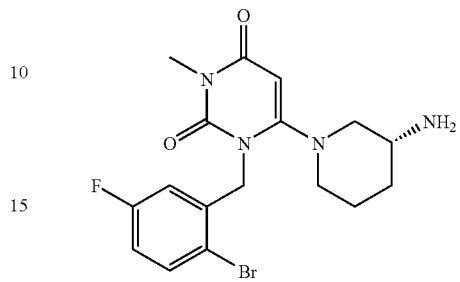

6-[3 (R)-Amino-piperidin-1-yl]-1-(2-bromo-5-fluoro-benzyl)-3-methyl-1H-pyrimidine-2,4-dione (10). To a solution of 6-chlorouracil (220 mg, 1.5 mmol) in a mixture of dry DMF-DMSO (6:1, 5 mL) under nitrogen at 0° C., was added sodium hydride (60%, 61 mg, 1.8 mmol) in portions. After 0.5 h, lithium bromide (83 mg, 1 mmol) was added and the mixture was stirred for 15 min at 0° C. A solution of 2-bromo-5-fluoro-benzyl bromide (497 mg, 1.8 mmol) in DMF (30 mL) was added dropwise, and stirred at this temperature for 1 h, and then RT overnight. The mixture was evaporated and co-evaporated with water in vacuo to remove most of the DMF, and then poured into ice-water. The precipitate was collected by filtration, and then suspended in cold MeOH and filtered. The solution was concentrated to give the crude monobenzylated product.

The crude product was treated with NaH and MeI using the procedure described in the preparation of compound 3, followed by the procedure used in the preparation of compound 4 to give the title compound. $^1$H-NMR (400 MHz, $CDCl_3$-$CD_3OD$ 10:1) δ 7.46 (dd, J=8.7, 5.2 Hz, 1 H), 6.82 (td, J=8.3, 2.9 Hz, 1 H), 6.59 (dd, J=9.1, 3.0 Hz, 1 H), 5.28 (s, 1H), 4.99-5.06 (ABq, J=41.7, 16.7 Hz, 2H), 3.28 (m, 1H), 3.23 (s, 3 H), 3.13-3.21 (m, 1 H), 2.86 (bd, J=12.6 Hz, 1 H), 2.71 (t, J=10.5 Hz, 1 H), 2.47 (t, J=11.0 Hz, 1 H), 2.00-2.08 (m, 1 H), 1.65-1.74 (m, 1 H), 1.42-1.53 (m, 2 H). MS (ES) [m+H] calc'd for $C_{17}H_{21}BrFN_4O_2$, 411.1; found, 411.1.

Compound 11

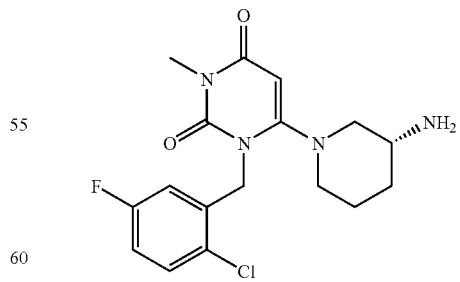

6-[3 (R)-Amino-piperidin-1-yl]-1-(2-chloro-5-fluoro-benzyl)-3-methyl-1H-pyrimidine-2,4-dione (11). The title compound was prepared from compound 1 using the same procedures as the preparation of compound 10, except that 2-chloro-5-fluoro-benzyl bromide was used in the place of 2-bromo-5-fluoro-benzyl bromide. $^1$H-NMR (400 MHz, CDCl$_3$-CD$_3$OD 10:1): δ 7.34-7.40 (dd, J=8.5, 5.1 Hz, 1 H), 6.97 (td, J=8.3, 2.9 Hz, 1 H), 6.72 (dd, J=9.0, 2.9 Hz, 1 H), 5.41 (s, 1 H), 5.11-5.19 (ABq, J=41.7, 16.7 Hz, 2H), 3.37 (s, 1 H), 3.32 (s, 3H), 3.23-3.30 (m, 1 H), 2.96 (d, J=12.1 Hz, 1 H), 2.81 (t, J=10.2 Hz, 1 H), 2.59 (t, J=11.1 Hz, 1 H), 2.13 (d, J=10.4 Hz, 1 H), 1.76-1.86 (m, 1 H), 1.52-1.63 (m, 2 H). MS (ES) [m+H] calc'd for C$_{17}$H$_{21}$ClFN$_4$O$_2$, 367.1; found 367.1.

Compound 12

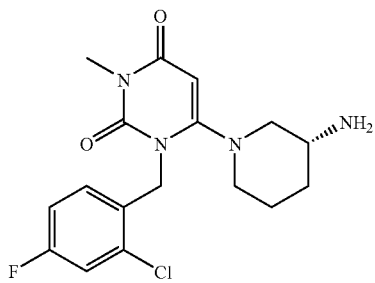

6-[3 (R)-Amino-piperidin-1-yl]-1-(2-chloro-4-fluoro-benzyl)-3-methyl-1H-pyrimidine-2,4-dione (12). The title compound was prepared from compound 1 using the same procedures as described the preparation of compound 10, except that 2-chloro-4-fluoro-benzyl bromide was used in the place of 2-bromo-5-fluoro-benzyl bromide. $^1$H-NMR (400 MHz, CDCl$_3$-CD$_3$OD 10:1) δ 7.15 (dd, J=8.211, 2.400 Hz, 1H), 6.95-7.06 (m, 2 H), 5.40 (s, 1 H), 5.09-5.18 (ABq, J=37.7, 15.9 Hz, 2H), 3.33-3.39 (m, 1 H), 3.30 (s, 3 H), 3.23-3.29 (m, 1 H), 2.98 (bd, J=12.9 Hz, 1 H), 2.79 (t, J=10.4 Hz, 1 H), 2.55-2.66 (t, J=11.2 Hz, 1 H), 2.13 (m, 1 H), 1.78-1.88 (m, 1 H), 1.55-1.65 (m, 2 H). MS (ES) [m+H] calc'd for C$_{17}$H$_{21}$ClFN$_4$O$_2$, 367.1; found 367.1.

Compound 13

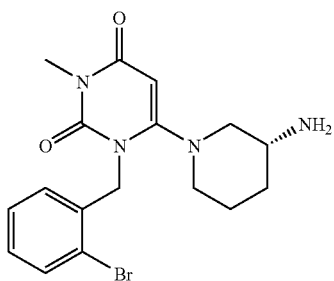

6-[3 (R)-Amino-piperidin-1-yl]-1-(2-bromo-benzyl)-3-methyl-1H-pyrimidine-2,4-dione (13). The title compound was prepared from compound 1 using the procedures described in the synthesis of compound 10, except that 2-bromo benzyl bromide was used in the place of 2-bromo-5-fluoro-benzyl bromide. $^1$H-NMR (400 MHz, CDCl$_3$-CD$_3$OD 10:1): δ 7.45 (d, J=7.8 Hz, 1 H), 7.16 (t, J=7.5 Hz, 1 H), 7.03 (t, J=7.2 Hz, 1 H), 6.80 (d, J=7.3 Hz, 1 H), 5.28 (s, 1 H), 4.93-5.05 (ABq, 2H, J=36.4, 16.4 Hz), 3.22 (m, 1H), 3.19 (m, 3 H), 3.09 (m, 1H), 2.84 (d, J=12.6 Hz, 1 H), 2.63 (t, J=10.5 Hz, 1 H), 2.42 (t, J=10.9 Hz, 1 H), 1.97 (d, J=11.1 Hz, 1 H), 1.58-1.69 (m, 1 H), 1.38-1.48 (m, 2 H). MS (ES) [m+H] calc'd for C$_{17}$H$_{22}$BrN$_4$O$_2$, 393.1; found, 393.1.

Compound 14 Compound 15

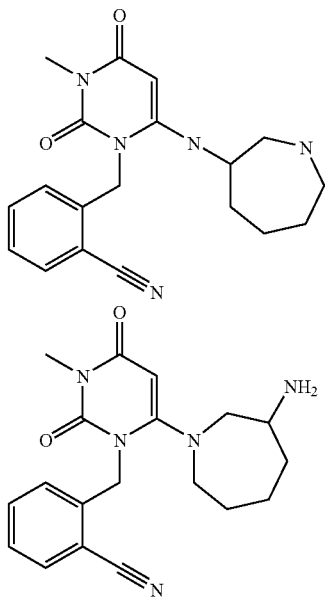

2-{6-[Azepan-3(±)-ylamino]-3-methyl-2,4-dioxo-3,4-dihydro-2H-pyrimidin-1-ylmethyl}-benzonitrile (14) and 2-{6-[3(±)-Amino-azepan-1-yl]-3-methyl-2,4-dioxo-3,4-dihydro-2H-pyrimidin-1-ylmethyl}-benzonitrile (15). Title compounds 14 and 15 were prepared from compound 3 (70 mg, 0.27 mmol) and azepan-3-ylamine (70 mg, 0.61 mg) using the procedure for the preparation of compound 4. Both compounds were purified by LC-MS.

Compound 14: $^1$H-NMR (400 MHz, CDCl$_3$-CD$_3$OD 10:1) δ 7.77 (d, J=7.8 Hz, 1 H), 7.66 (t, J=7.6 Hz, 1 H), 7.47 (t, J=8.0 Hz, 1 H), 7.36 (d, J=8.1 Hz, 1 H), 5.54 (s, 1 H), 5.49 (s, 1 H), 5.27-5.36 (ABq, J=26.0, 16.4 Hz, 2H), 3.50 (m, 2 H), 3.37 (s, 2 H), 3.26 (s, 3 H), 3.12 (m, 1H), 3.04 (m, 1H), 2.07 (m, 1H), 1.86 (m, 1H), 1.60-1.71 (m, 3H). MS (ES) [m+H] calc'd for C$_{19}$H$_{24}$N$_5$O$_2$, 354.2; found, 354.2.

Compound 15: $^1$H-NMR (400 MHz, CDCl$_3$-CD$_3$OD 10:1) δ 7.77 (d, J=8.1 Hz, 1 H), 7.63 (t, J=7.6 Hz, 1 H), 7.46 (t, J=8.0 Hz, 1 H), 7.19 (d, J=7.6 Hz, 1 H), 5.48 (s, 1H), 5.44-5.52 (ABq, J=61.9, 18.4 Hz, 2H), 3.80 (s, 1 H), 3.58-3.50 (m, 1 H), 3.39-3.39 (m, 1 H), 3.26 (s, 3H), 3.13 (m, 1 H), 2.89 (t, J=12.4 Hz, 1 H), 2.04 (m, 1 H), 1.93 (m, 1 H), 1.86 (m, 2 H), 1.59-1.70 (m, 2 H). MS (ES) [m+H] calc'd for C$_{19}$H$_{24}$N$_5$O$_2$, 354.2; found, 354.2.

Compound 16

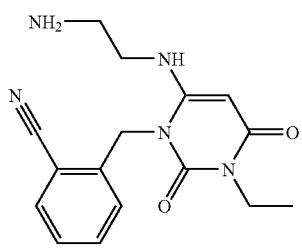

2-[6-(2-Amino-ethylamino)-3-ethyl-2,4-dioxo-3,4-dihydro-2H-pyrimidin-1-ylmethyl]-benzonitrile (16). Compound 2 (150 mg, 0.57 mmol) in THF-DMSO (6:1, 4 mL) was treated with 60% NaH (26 mg, 0.65 mmol), followed by adding ethyl bromide (300 uL). In a sealed tube, ~20% crude product in dry MeOH (3 mL) was treated with NaHCO$_3$ and ethane-1,2-diamine (200 µL) at 120° C. for 2 h, and purified by LC-MS to give the title compound 16. $^1$H-NMR (400 MHz, CDCl$_3$-CD$_3$OD 10:1) δ 7.70 (d, J=7.8 Hz, 1 H), 7.58 (t, J=7.7 Hz, 1 H), 7.40 (t, J=7.4 Hz, 1 H), 7.12 (d, J=8.1 Hz, 1 H), 5.37 (s, 2 H), 3.95 (q, J=6.8 Hz, 2 H), 3.45 (t, J=5.9 Hz, 2 H), 3.11 (t, J=6.1 Hz, 2 H), 1.19 (t, J=6.8 Hz, 3 H). MS (ES) [m+H] calc'd for C$_{16}$H$_{20}$N$_5$O$_2$, 314.2; found 314.2.

Compound 17

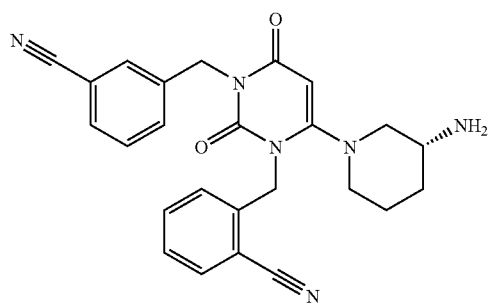

2-{6-[3(R)-Amino-piperidin-1-yl]-3-(3-cyano-benzyl)-2,4-dioxo-3,4-dihydro-2H-pyrimidin-1-ylmethyl}-benzonitrile (17). Compound 2 (65 mg, 0.25 mmol) in DME-DMF (2:1, 2.5 mL) was treated with 60% NaH (15 mg, 0.38 mmol) at 0° C. for 20 min, and then LiBr (25 mg) was added. 10 min later, m-cyano-benzyl bromide (55 mg, 0.28 mg) was added, and the mixture was stirred at RT for 5 h, and concentrated. The crude residue was dissolved in MeOH (3 mL). (R)-3-Amino-piperidine dihydrochloride (52 mg, 0.3 mmol) and sodium bicarbonate (100 mg) were added. The mixture was heated in a sealed tube at 120° C. for 2 h, and then filtered and concentrated. LC-MS purification gave the title compound 17 in 84% yield. $^1$H-NMR (400 MHz, CDCl$_3$-CD$_3$OD 10:1) δ 7.67 (d, J=7.8 Hz, 1 H), 7.52-7.62 (m, 4 H), 7.35-7.46 (m, 2 H), 7.27 (d, J=7.8 Hz, 1 H), 5.43 (s, 1 H), 5.15-5.31 (ABq, J=40.9, 13.7 Hz, 2 H), 5.04 (s, 2 H), 3.40 (s, 1 H), 3.40 (m, 1 H), 3.03 (m, 1 H), 2.91 (m, 1 H), 2.76 (s, 1H), 2.13 (s, 1 H), 1.92 (m, 1 H), 1.63-1.74 (m, 2 H). MS (ES) [m+H] calc'd for C$_{25}$H$_{25}$N$_6$O$_2$, 441.2; found 441.2.

Compound 18

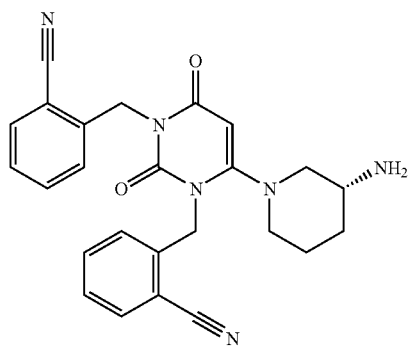

2-{6-[3(R)-Amino-piperidin-1-yl]-3-(2-cyano-benzyl)-2,4-dioxo-3,4-dihydro-2H-pyrimidin-1-ylmethyl}-benzonitrile (18). Title compound 18 was prepared by the methods used in the preparation of compound 17, except that α-bromo-o-tolunitrile was used in the place of m-cyano-benzyl bromide. $^1$H-NMR (400 MHz, CDCl$_3$-CD$_3$OD 10:1) δ 7.64 (d, J=6.8 Hz, 1H), 7.60 (d, J=7.8 Hz, 1H), 7.55 (t, J=7.8 Hz, 2H), 7.44 (t, J=7.6 Hz, 1 H), 7.38 (t, J=7.5 Hz, 1 H), 7.31 (t, J=7.6Hz, 1H), 7.27 (d, J=7.8 Hz, 1H), 7.12 (d, J=7.8 Hz, 1 H), 5.45 (s, 1 H), 5.15-5.32 (m, 4 H), 3.36-3.47 (m, 2 H), 2.98 (m, 2 H), 2.10 (m, 1 H), 1.91 (m, 1 H), 1.68 (m, 2 H). MS (ES) [m+H] calc'd for C$_{25}$H$_{25}$N$_6$O$_2$, 441.2; found 441.2.

Compound 19

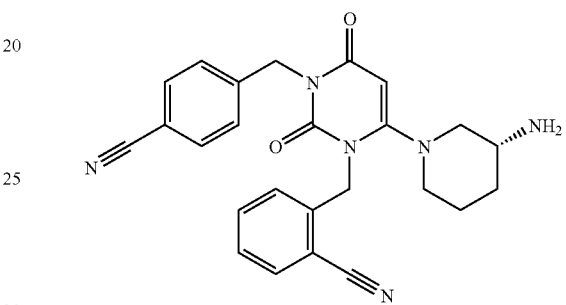

2-{6-[3(R)-Amino-piperidin-1-yl]-3-(4-cyano-benzyl)-2,4-dioxo-3,4-dihydro-2H-pyrimidin-1-ylmethyl}-benzonitrile (19). Title compound 19 was prepared by the methods used in the preparation of compound 17, except that p-cyano-benzyl bromide was used in the place of m-cyano benzyl bromide. $^1$H-NMR (400 MHz, CDCl$_3$-CD$_3$OD 10:1) δ 7.70 (d, J=7.8 Hz, 1 H), 7.56-7.63 (m, 3 H), 7.46 (m, 3 H), 7.29 (d, J=7.8 Hz, 1 H), 5.47 (s, 1 H), 5.16-5.36 (ABq, J=51.1, 14.7 Hz, 2 H), 5.11 (s, 2 H), 3.36-3.47 (m, 2 H), 2.90-3.07 (m, 2 H), 2.79 (s, 1 H), 2.15 (s, 1 H), 1.95 (s, 1 H), 1.73 (s, 2 H). MS (ES) [m+H] calc'd for C$_{25}$H$_{25}$N$_6$O$_2$, 441.2; found 441.2.

Compound 20

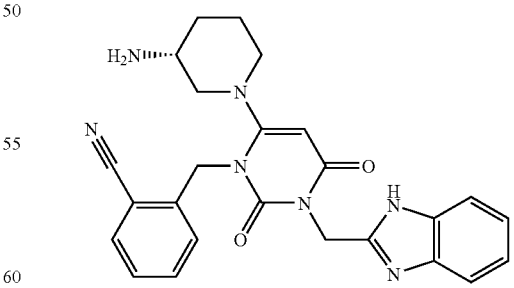

2-[6-(3-Amino-piperidin-1-yl)-3-(1H-benzoimidazol-2-ylmethyl)-2,4-dioxo-3,4-dihydro-2H-pyrimidin-1-ylmethyl]-benzonitrile (20). Title compound 20 was prepared by the methods used in the preparation of compound 17, except that 2-chloromethyl benzimidazole was used in the place of m-cyano-benzyl bromide. ¹H-NMR (400 MHz, CDCl₃-CD₃OD 10:1) δ 7.67 (d, J=3.0 Hz, 1H), 7.65-7.56 (m, 2 H), 7.47 (d, J=3.3 Hz, 2 H), 7.46 (d, J=3.3 Hz, 1 H), 7.37-7.40 (m, 2 H), 5.52 (s, 3 H), 5.23 (s, 2 H), 3.51 (d, J=9.6 Hz, 1 H), 3.36 (m, 1 H), 2.87-2.92 (m, 2 H), 2.64-2.72 (m, 1 H), 2.09 (m, 1 H), 1.76 (m, 1 H), 1.52-1.64 (m, 2 H). MS (ES) [m+H] calc'd for C₂₅H₂₆N₇O₂, 456.2; found 456.2.

Compound 21

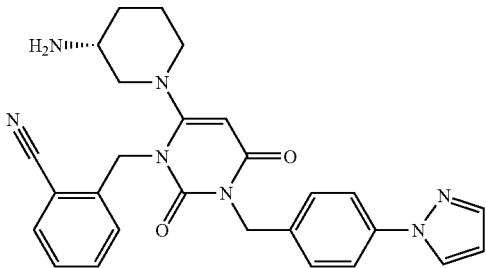

2-{6-[3(R)-Amino-piperidin-O-yl]-2,4-dioxo-3-(4-pyrazol-1-yl-benzyl)-3,4-dihydro-2H-pyrimidin-1-ylmethyl}-benzonitrile (21). Title compound 21 was prepared by the methods used in the preparation of compound 17, except that 1-(4-bromomethyl-phenyl)-1H-pyrazole was used in the place of m-cyano-benzyl bromide. ¹H-NMR (400 MHz, CDCl₃-CD₃OD 10:1) δ 7.90 (d, J=2.5 Hz, 1 H), 7.71 (d, J=1.8 Hz, 1 H), 7.65 (d, J=7.6 Hz, 1 H), 7.51-7.58 (m, 3 H), 7.43-7.37 (m, 3 H), 7.22 (d, J=7.8 Hz, 1 H), 6.47 (t, J=2.1 Hz, 1 H), 5.43 (s, 1H), 5.14-5.30 (ABq, J=41.2, 16.4 Hz, 2 H), 5.05 (s, 2 H), 3.32-3.40 (m, 2H), 2.96 (m, 1 H), 2.89 (m, 1 H), 2.70 (m, 1 H), 2.10 (m, 1 H), 1.88 (m, 1 H), 1.66 (s, 2 H). MS (ES) [m+H] calc'd for C₂₇H₂₈N₇O₂, 482.2; found 482.2.

Compound 22

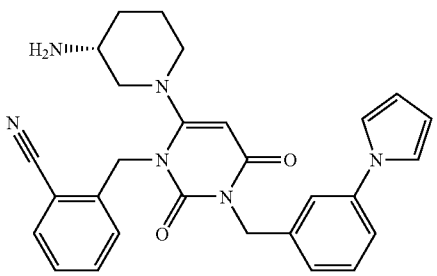

2-{6-[3(R)-Amino-piperidin-1-yl]-2,4-dioxo-3-(3-pyrrol-1-yl-benzyl)-3,4-dihydro-2H-pyrimidin-1-ylmethyl}-benzonitrile (22). Title compound 22 was prepared by the methods used in the preparation of compound 17, except that 1-(3-bromomethyl-phenyl)-1H-pyrrole was used in the place of m-cyano-benzyl bromide. ¹H-NMR (400 MHz, CDCl₃-CD₃OD 10:1) δ 7.59 (d, J=7.3 Hz, 1 H), 7.48 (t, J=7.7 Hz, 1 H), 7.24-7.36 (m, 4 H), 7.21 (t, J=7.6 Hz, 1 H), 7.02 (t, J=2.1 Hz, 2 H), 6.32 (t, J=2.0 Hz, 2 H), 5.42 (s, 1H), 5.11-5.20 (ABq, J=44.7, 15.9 Hz, 2 H), 5.06 (s, 2 H), 3.36 (m, 2 H), 2.98 (m, 1 H), 2.89 (m, 1 H), 2.70 (m, 1 H), 2.10 (m, 1 H), 1.88 (m, 1 H), 1.73-1.58 (m, 2H). MS (ES) [m+H] calc'd for C₂₈H₂₉N₆O₂, 481.2; found 481.2.

Compound 23

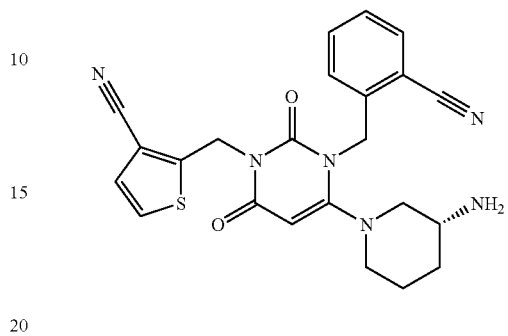

6-[3 (R)-Amino-piperidin-1-yl]-3-(2-cyano-benzyl)-2,6-dioxo-3,6-dihydro-2H-pyrimidin-1-ylmethyl]-thiophene-3-carbonitrile (23). Title compound 23 was prepared by the methods used in the preparation of compound 17, except that 2-bromomethyl-thiophene-3-carbonitrile was used in the place of m-cyano-benzyl bromide. ¹H-NMR (400 MHz, CDCl₃-CD₃OD 10:1) δ 7.65 (d, J=7.6 Hz, 1 H), 7.57 (t, J=7.8 Hz, 1 H), 7.40 (t, J=7.7 Hz, 1 H), 7.29 (d, J=7.8 Hz, 1 H), 7.25 (dd, J=5.3, 1.3 Hz, 1 H), 7.11 (dd, J=5.3, 1.0 Hz, 1 H), 5.45 (s, 1 H), 5.35 (s, 2 H), 5.15-5.33 (ABq, J=45.0, 15.5 Hz, 2 H), 3.38 (bd, J=10.1 Hz, 2 H), 2.98 (m, 2 H), 2.72 (s, 1 H), 2.12 (d, J=7.3 Hz, 1 H), 1.83-1.93 (m, 1 H), 1.61-1.72 (m, 2 H). MS (ES) [m+H] calc'd for C₂₃H₂₃N₆O₄, 447.1; found 447.1.

Compound 24

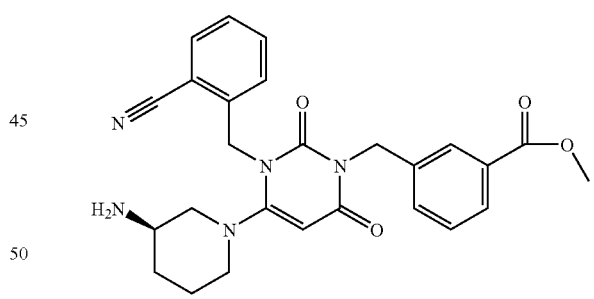

3-{4-[3(R)-Amino-piperidin-1-yl]-3-(2-cyano-benzyl)-2,6-dioxo-3,6-dihydro-2H-pyrimidin-1-ylmethyl}-benzoic acid methyl ester (24). Title compound 24 was prepared by the methods used in the preparation of compound 17, except that 3-bromomethyl-benzoic acid methyl ester was used in the place of m-cyano-benzyl bromide. ¹H-NMR (400 MHz, CDCl₃-CD₃OD 10:1) δ 7.99 (s, 1 H), 7.91 (d, J=7.8 Hz, 1H), 7.65 (d, J=7.6 Hz, 1 H), 7.56 (d, J=7.9 Hz, 1 H), 7.52 (d, J=7.6 Hz, 1 H), 7.39 (t, J=7.6 Hz, 1 H), 7.34 (t, J=7.6 Hz, 1 H), 7.23 (d, J=8.1 Hz, 1 H), 5.44 (s, 1H), 5.12-5.31 (ABq, J=43.7, 15.9 Hz, 2 H), 5.08 (s, 2 H), 3.90 (s, 3 H), 3.31-3.39 (m, 2 H), 2.98 (d, J=11.9 Hz, 1 H), 2.87 (m, 1 H), 2.71 (m, 1 H), 2.11 (m, 1

H), 1.89 (m, 1 H), 1.73-1.59 (m, 2 H). MS (ES) [m+H] calc'd for $C_{26}H_{28}N_5O_4$, 474.2; found 474.2.

Compound 25

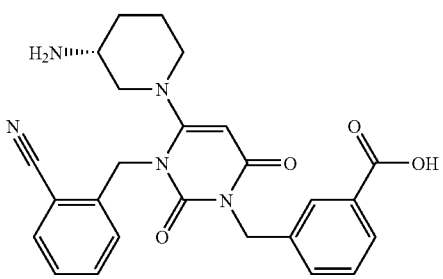

3-{4-[3(R)-Amino-piperidin-1-yl]-3-(2-cyano-benzyl)-2,6-dioxo-3,6-dihydro-2H-pyrimidin-1-ylmethyl}-benzoic acid (25). A crude mixture of compound 24 (~50 mg) was treated with LiOH in THF-water (10:1) to give the title compound 25. $^1$H-NMR (400 MHz, CDCl$_3$-CD$_3$OD 10:1) δ 7.90 (s, 1 H), 7.86 (d, J=7.6 Hz, 1 H), 7.60 (d, J=7.6 Hz, 1 H), 7.50 (t, J=8.2 Hz, 1 H), 7.45 (d, J=7.3 Hz, 1 H), 7.26-7.36 (m, 2H), 7.17 (d, J=8.1 Hz, 1 H), 5.39 (s, 1 H), 5.10-5.25 (ABq, J=36.9, 15.5 Hz, 2 H), 5.03 (s, 2H), 3.31 (m, 2H), 2.95 (m, 1 H), 2.81 (m, 1 H), 2.64 (m, 1 H), 2.07 (m, 1 H), 1.82 (m, 1H), 1.51-1.68 (m, 2 H). MS (ES) [m+H] calc'd for $C_{25}H_{26}N_5O_4$, 460.2; found 460.2.

Compound 26

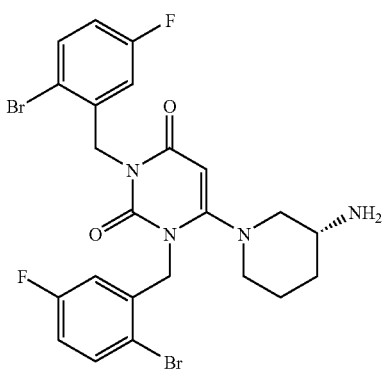

6-[3 (R)-Amino-piperidin-1-yl]-1,3-bis-(2-bromo-5-fluoro-benzyl)-1H-pyrimidine-2,4-dione (26). The title compound was prepared from 1 by di-benzylation, using the procedure for the preparation of 2, except that 2-bromo-5-fluoro-benzyl bromide was used in the place of α-bromo-o-tolunitrile, followed by treatment with 3-(R)-amino-piperidine under the conditions described in the preparation of compound 4. $^1$H-NMR (400 MHz, CDCl$_3$-CD$_3$OD 10:1) δ 7.42 (dd, J=8.6, 5.3 Hz, 2 H), 7.11-7.08 (dd, J=9.1, 2.2 Hz, 1 H), 7.06 (dd, J=9.3, 2.8 Hz, 1 H), 6.78-6.84 (m, 2 H), 5.71 (s, 1H), 5.29 (s, 4 H), 4.22 (d, J=11.1 Hz, 1 H), 3.82 (d, J=13.4 Hz, 1 H), 3.07-3.24 (m, 3H), 2.06 (m, 1 H), 1.75-1.83 (m, 1 H), 1.63-1.72 (m, 1 H), 1.50-1.59 (m, 1 H). MS (ES) [m+H] calc'd for $C_{23}H_{23}Br_2F_2N_3O_2$, 583.01; found 583.01.

Compound 27

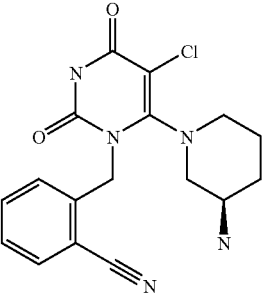

2-{6-[3(R)-Amino-piperidin-1-yl]-5-chloro-2,4-dioxo-3,4-dihydro-2H-pyrimidin-1-ylmethyl}-benzonitrile (27). Compound 4 (100 mg) in THF (2 mL) was treated with 4M HCl in dioxane (1 mL) at RT for 1 h, concentrated, and then purified by LC-MS to give the title compound. $^1$H-NMR (400 MHz, DMSO-D6): δ ppm 12.0 (s, 1H), 7.88 (d, J=7.6 Hz, 1 H), 7.68 (t, J=7.7 Hz, 1 H), 7.49 (t, J=7.7 Hz, 1 H), 7.36 (d, J=7.8 Hz, 1 H), 5.09-5.21 (m, 2 H), 3.17 (m, 2 H), 2.96 (t, J=11.1 Hz, 1 H), 2.86 (d, J=10.6 Hz, 1 H), 2.65 (m, 1 H), 1.90 (d, J=11.6 Hz, 1 H), 1.57 (d, J=13.1 Hz, 1 H), 1.19-1.31 (m, 1 H), 1.03-1.15 (m, 1 H). MS (ES) [m+H] calc'd for $C_{17}H_{19}ClN_5O_2$, 360.1; found, 360.1.

Compound 28

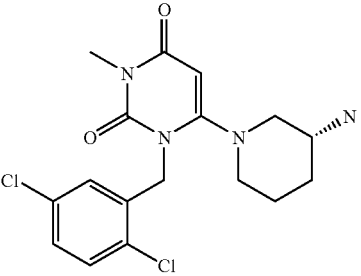

6-[3 (R)-Amino-piperidin-1-yl]-1-(2,5-di-chloro-benzyl)-3-methyl-1H-pyrimidine-2,4-dione (28). The title compound was prepared from compound 1 using the same procedures as in the preparation of compound 10, except that 2,5-di-chloro-benzyl bromide was used in the place of 2-bromo-5-fluoro-benzyl bromide. $^1$H-NMR (400 MHz, CDCl$_3$-CD$_3$OD 10:1): δ ppm 7.50 (d, J=8.6 Hz, 1 H), 7.39 (dd, J=8.3, 2.526 Hz, 1 H), 7.22 (d, J=2.5 Hz, 1 H), 5.41 (s, 1 H), 5.01-4.93 (ABq, J=41.9, 16.2 Hz, 2H), 3.25 (m, 2 H), 3.10 (s, 3H), 2.85 (m, 1 H), 2.76 (m, 1 H), 2.67 (m, 1 H), 1.91 (m, 1H), 1.75 (m, 1 H), 1.45 (m, 2 H). MS (ES) [m+H] calc'd for $C_{17}H_{21}Cl_2N_4O_2$, 383.1; found 383.1.

Compound 29

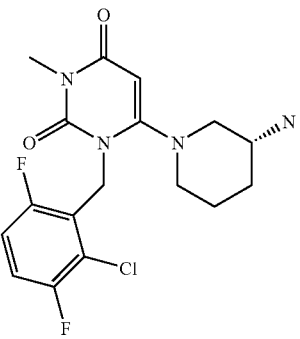

6-[3 (R)-Amino-piperidin-1-yl]-1-(2-chloro-3,6-di-fluoro-benzyl)-3-methyl-1H-pyrimidine-2,4-dione (29). The title compound was prepared from compound 1 using the same procedures as in the preparation of compound 10, except that 2-chloro-3,6-di-fluoro-benzyl bromide was used in the place of 2-bromo-5-fluoro-benzyl bromide. $^1$H NMR (400 MHz, CDCl$_3$-CD$_3$OD 10:1) δ ppm 6.98-7.06 (m, 2 H), 6.90 (m, 2 H), 5.31 (s, 1 H), 5.01-5.20 (ABq, J=24.2, 14.4 Hz, 2H), 3.28-3.37 (m, 2 H) 3.13 (s, 3H), 3.01-2.94 (m, 1 H), 2.6-2.9 (m, 2 H), 2.10 (m, 1 H), 1.92 (m, 2 H), 1.73 (s, 1 H), 1.6-1.75 (m, 2 H). MS (ES) [m+H] calc'd for C$_{17}$H$_{20}$ClF$_2$N$_4$O$_2$, 385.1; found 385.1.

Compound 30

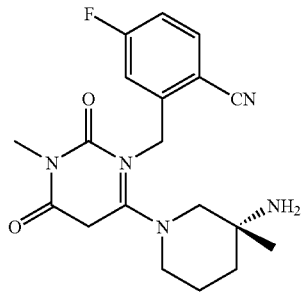

(R)-2-((6-(3-amino-3-methylpiperidin-1-yl)-3-methyl-2,4-dioxo-3,4-dihydropyrimidin-1(2H)-yl)methyl)-4-fluorobenzonitrile (30). 2-(6-Chloro-3-methyl-2,4-dioxo-3,4-dihydro-2H-pyrimidin-1-ylmethyl)-4-fluoro-benzonitrile (300 mg, 1.0 mmol), (R)-3-amino-3-methyl-piperidine dihydrochloride (266 mg, 1.4 mmol) and sodium bicarbonate (500 mg, 5.4 mmol) were stirred in a sealed tube in EtOH (3 mL) at 100° C. for 2 hrs. The final compound was obtained as TFA salt after HPLC purification. $^1$H-NMR (400 MHz, CD3OD): δ. 7.78-7.83 (m, 1H), 7.14-7.26 (m, 2H), 5.47 (s, 1H), 5.12-5.36 (ABq, 2H, J=105.2, 15.6 Hz), 3.21 (s, 1H), 2.72-3.15 (m, 4H), 1.75-1.95 (m, 4H), 1.39 (s, 3H). MS (ES) [m+H] calc'd for C$_{19}$H$_{22}$FN5O2, 372.41; found, 372.41.

Compound 34

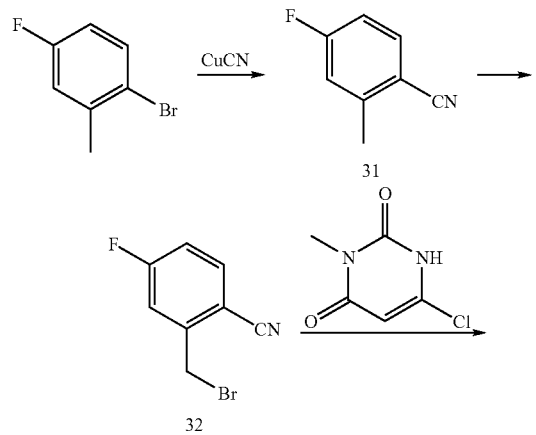

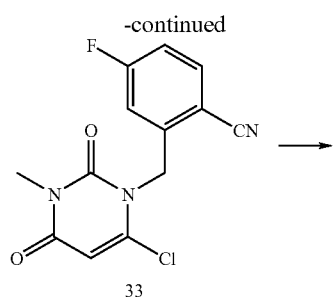

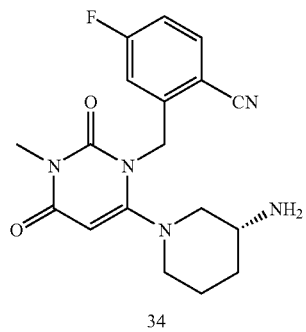

4-Fluoro-2-methylbenzonitrile (31). A mixture of 2-bromo-5-fluorotoluene (3.5 g, 18.5 mmol) and CuCN (2 g, 22 mmol) in DMF (100 mL) was refluxed for 24 hours. The reaction was diluted with water and extracted with hexane. The organics were dried over MgSO$_4$ and the solvent removed to give product 31 (yield 60%). 1H-NMR (400 MHz, CDCl$_3$): δ 7.60 (dd, J=5.6, 8.8 Hz, 1H), 6.93-7.06 (m, 2H), 2.55 (s, 3H).

2-Bromomethyl-4-fluorobenzonitrile (32). A mixture of 4-fluoro-2-methylbenzonitrile (2 g, 14.8 mmol), NBS (2.64 g, 15 mmol) and AIBN (100 mg) in CCl$_4$ was refluxed under nitrogen for 2 hours. The reaction was cooled to room temperature. The solid was removed by filtration. The organic solution was concentrated to give crude product as an oil, which was used in the next step without further purification. $^1$H-NMR (400 MHz, CDCl$_3$): δ 7.68 (dd, J=5.2, 8.4 Hz, 1H), 7.28 (dd, J=2.4, 8.8 Hz, 1H), 7.12 (m, 1H), 4.6 (s, 2H).

Alternatively, 32 was made as follows. 4-Fluoro-2-methylbenzonitrile (1 kg) in DCE (2 L) was treated with AIBN (122 g) and heated to 75° C. A suspension of DBH (353 g) in DCE (500 mL) was added at 75° C. portionwise over 20 minutes. This operation was repeated 5 more times over 2.5 hours. The mixture was then stirred for one additional hour and optionally monitored for completion by, for example, measuring the amount of residual benzonitrile using HPLC. Additional AIBN (e.g., 12.5 g) was optionally added to move the reaction toward completion. Heating was stopped and the mixture was allowed to cool overnight. N,N-diisopropylethylamine (1.3 L) was added (at <10° C. over 1.5 hours) and then diethyl phosphite (1.9 L) was added (at <20° C. over 30 min). The mixture was then stirred for 30 minutes or until completion. The mixture was then washed with 1% sodium metabisulfite solution (5 L) and purified with water (5 L). The organic phase was concentrated under vacuum to afford 32 as a dark brown oil (3328 g), which was used without further purification (purity was 97% (AUC)).

2-(6-Chloro-3-methyl-2,4-dioxo-3,4-dihydro-2H-pyrimidin-1-ylmethyl)-4-fluoro-benzonitrile (33). A mixture of crude 3-methyl-6-chlorouracil (0.6 g, 3.8 mmol), 2-bromomethyl-4-fluorobenzonitrile (0.86 g, 4 mmol) and K$_2$CO$_3$ (0.5 g, 4 mmol) in DMSO (10 mL) was stirred at 60° C. for 2 hours. The reaction was diluted with water and extracted with EtOAc. The organics were dried over MgSO₄ and the solvent removed. The residue was purified by column chromatography. 0.66 g of the product was obtained (yield: 60%). ¹H-NMR (400 MHz, CDCl₃): δ 7.73 (dd, J=7.2, 8.4 Hz, 1H), 7.26 (d, J=4.0 Hz, 1H), 7.11-7.17 (m, 1H), 6.94 (dd, J=2.0, 9.0 Hz, 1H), 6.034 (s, 2H), 3.39 (s, 3H). MS (ES) [m+H] calc'd for $C_{13}H_9ClFN_3O_2$, 293.68; found 293.68.

Alternatively, 33 was made as follows. To a solution of 6-chloro-3-methyluracil (750 g) and N,N-diisopropylethylamine (998 mL) in NMP (3 L) was added (at <30° C. over 25 min) a solution of 32 (2963 g crude material containing 1300 g of 32 in 3 L of toluene). The mixture was then heated at 60° C. for 2 hours or until completion (as determined, for example, by HPLC). Heating was then stopped and the mixture was allowed to cool overnight. Purified water (3.8 L) was added, and the resultant slurry was stirred at ambient temperature for 1 hour and at <5° C. for one hour. The mixture was then filtered under vacuum and the wet cake was washed with IPA (2×2.25 L). The material was then dried in a vacuum oven at 40±5° C. for 16 or more hours to afford 33 as a tan solid (>85% yield; purity was >99% (AUC)).

2-[6-(3-Amino-piperidin-1-yl)-3-methyl-2,4-dioxo-3,4-dihydro-2H-pyrimidin-1-ylmethyl]-4-fluoro-benzonitrile (34). 2-(6-Chloro-3-methyl-2,4-dioxo-3,4-dihydro-2H-pyrimidin-1-ylmethyl)-4-fluoro-benzonitrile (300 mg, 1.0 mmol), (R)-3-amino-piperidine dihydrochloride (266 mg, 1.5 mmol) and sodium bicarbonate (500 mg, 5.4 mmol) were stirred in a sealed tube in EtOH (3 mL) at 100° C. for 2 hrs. The final compound was obtained as TFA salt after HPLC purification. ¹H-NMR (400 MHz, CD₃OD): δ. 7.77-7.84 (m, 1H), 7.16-7.27 (m, 2H), 5.46 (s, 1H), 5.17-5.34 (ABq, 2H, J 35.2, 15.6 Hz), 3.33-3.47 (m, 2H), 3.22 (s, 3H), 2.98-3.08 (m, 1H), 2.67-2.92 (m, 2H), 2.07-2.17 (m, 1H), 1.82-1.92 (m, 1H), 1.51-1.79 (m, 2H). MS (ES) [m+H] calc'd for $C_{18}H_{20}FN_5O_2$, 357.38; found, 357.38.

Alternatively, the free base of 34 was prepared as follows. A mixture of 33 (1212 g), IPA (10.8 L), (R)-3-amino-piperidine dihydrochloride (785 g), purified water (78 mL) and potassium carbonate (2.5 kg, powder, 325 mesh) was heated at 60° C. until completion (e.g., for >20 hours) as determined, for example, by HPLC. Acetonitrile (3.6 L) was then added at 60° C. and the mixture was allowed to cool to <25° C. The resultant slurry was filtered under vacuum and the filter cake was washed with acetonitrile (2×3.6 L). The filtrate was concentrated at 45° C. under vacuum (for >3 hours) to afford 2.6 kg of the free base of 34.

The HCl salt of 34 was prepared from the TFA salt as follows. The TFA salt (34) was suspended in DCM, and then washed with saturated Na₂CO₃. The organic layer was dried and removed in vacuo. The residue was dissolved in acetonitrile and HCl in dioxane (1.5 eq.) was added at 0° C. The HCl salt was obtained after removing the solvent. ¹H-NMR (400 MHz, CD₃OD): δ. 7.77-7.84 (m, 1H), 7.12-7.26 (m, 2H), 5.47 (s, 1H), 5.21-5.32 (ABq, 2H, J=32.0, 16.0 Hz), 3.35-3.5 (m, 2H), 3.22 (s, 3H), 3.01-3.1 (m, 1H), 2.69-2.93 (m, 2H), 2.07-2.17 (m, 1H), 1.83-1.93 (m, 1H), 1.55-1.80 (m, 2H). MS (ES) [m+H] calc'd for $C_{18}H_{20}FN_5O_2$, 357.38; found, 357.38.

Alternatively, the HCl salt was prepared from the free base as follows. To a solution of free base in CH₂Cl₂ (12 L) was added (at <35° C. over 18 minutes) 2 M hydrochloric acid (3.1 L). The slurry was stirred for 1 hour and then filtered. The wet cake was washed with CH₂Cl₂ (3.6 L) and then THF (4.8 L). The wet cake was then slurried in THF (4.8 L) for one hour and then filtered. The filter cake was again washed with THF (4.8 L). The material was then dried in a vacuum oven at 50° C. (with a nitrogen bleed) until a constant weight (e.g., >26 hours) to afford 34 as the HCl salt as a white solid (1423 g, >85% yield).

The succinate salt of 34 was prepared from the HCl salt as follows. To a mixture of the HCl salt of 34 (1414 g), CH₂Cl₂ (7 L) and purified water (14 L) was added 50% NaOH solution (212 mL) until the pH of the mixture was >12. The biphasic mixture was stirred for 30 min and the organic layer was separated. The aqueous layer was extracted with CH₂Cl₂ (5.7 L) and the combined organic layers were washed with purified water (6 L). The organic layer was then passed through an in-line filter and concentrated under vacuum at 30° C. over three hours to afford the free base as an off-white solid. The free base was slurried in prefiltered THF (15 L) and prefiltered IPA (5.5 L). The mixture was then heated at 60° C. until complete dissolution of the free base was observed. A prefiltered solution of succinic acid (446 g) in THF (7 L) was added (over 23 min) while maintaining the mixture temperature at >57° C. After stirring at 60° C. for 15 min, the heat was turned off, the material was allowed to cool, and the slurry was stirred for 12 hours at 25±5° C. The material was filtered under vacuum and the wet cake was washed with prefiltered IPA (2×4.2 L). The material was then dried in a vacuum oven at 70±5° C. (with a nitrogen bleed) for >80 hours to afford the succinate salt of 34 as a white solid (1546 g, >90% yield).

The product was also converted to a variety of corresponding acid addition salts. Specifically, the benzonitrile product (approximately 10 mg) in a solution of MeOH (1 mL) was treated with various acids (1.05 equivalents). The solutions were allowed to stand for three days open to the air. If a precipitate formed, the mixture was filtered and the salt dried. If no solid formed, the mixture was concentrated in vacuo and the residue isolated. In this way, salts of 34 were prepared from the following acids: benzoic, p-toluenesulfonic, succinic, R-(-)-Mandelic and benzenesulfonic. The succinate was found to be crystalline as determined by x-ray powder diffraction analysis.

In addition, the methanesulfonate salt was prepared as follows. A 10.5 g aliquot of the benzonitrile product was mixed with 400 mL of isopropylacetate. The slurry was heated to 75° C. and filtered through #3 Whatman filter paper. The solution was heated back to 75° C. and a 1M solution of methanesulfonic acid (30.84 mL) was added slowly over 10 minutes while stirring. The suspension was cooled to room temperature at a rate of about 20° C./hr. After 1 hr at room temperature, the solid was filtered and dried in an oven overnight to obtain the methanesulfonate salt.

It will be apparent to those skilled in the art that various modifications and variations can be made to the methods of the present invention without departing from the spirit or scope of the invention. Thus, it is intended that the present invention cover the modifications and variations of this invention provided they come within the scope of the appended claims and their equivalents.

What is claimed is:
1. A process comprising:
reacting a compound comprising the formula

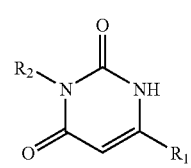

with a compound comprising the formula

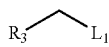

under conditions that form a reaction product comprising the formula

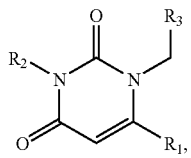

wherein
R₁ is selected from the group consisting of halo and OSO₂R' where R' is alkyl, haloalkyl, or aryl optionally substituted by halo, alkyl, alkoxy or amino;
R₂ is methyl;
R₃ is selected from the group consisting of 2-cyanophenyl and 2-cyano-5-fluorophenyl; and
L₁ is a leaving group.

2. The process of claim 1, further comprising reacting the reaction product with a piperidine comprising the formula

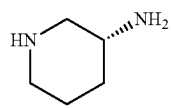

under conditions that form a second reaction product comprising the formula

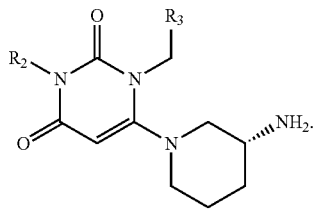

3. The process of any one of claim 1 or 2, wherein R₁ is halo.

4. A process comprising:
reacting a compound comprising the formula

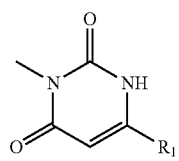

with a compound comprising the formula

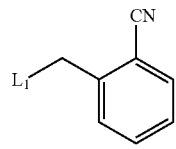

under conditions that form a reaction product comprising the formula

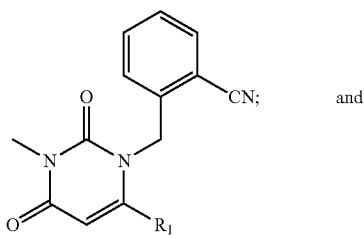

and reacting the reaction product with a piperidine comprising the formula

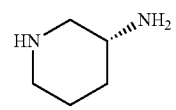

under conditions that form a second reaction product comprising the formula:

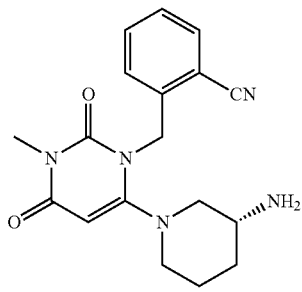

wherein
R₁ is halo, and
L₁ is halo.

5. A process comprising:
reacting a compound comprising the formula

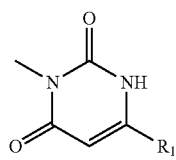

with a compound comprising the formula
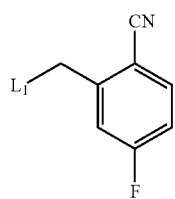
under conditions that form a reaction product comprising the formula
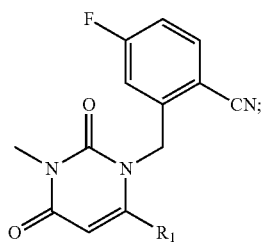
and
reacting the reaction product with a piperidine comprising the formula
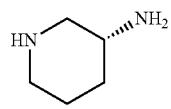
under conditions that form a second reaction product comprising the formula
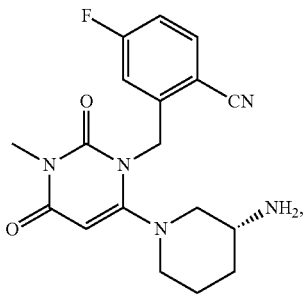
wherein
$R_1$ is halo, and
$L_1$ is halo.
* * * * *